United States Patent
Walsh et al.

(10) Patent No.: US 10,843,332 B2
(45) Date of Patent: Nov. 24, 2020

(54) SOFT EXOSUIT FOR ASSISTANCE WITH HUMAN MOTION

(71) Applicant: President and Fellows of Harvard College, Cambridge, MA (US)

(72) Inventors: Conor J. Walsh, Cambridge, MA (US); Alan Thomas Asbeck, Cambridge, MA (US); Ye Ding, Cambridge, MA (US); Ignacio Galiana Bujanda, Cambridge, MA (US); Stefano Marco Maria De Rossi, Cambridge, MA (US)

(73) Assignee: President and Fellow of Harvard College, Cambridge, MA (US)

( * ) Notice: Subject to any disclaimer, the term of this patent is extended or adjusted under 35 U.S.C. 154(b) by 1380 days.

(21) Appl. No.: 14/893,934

(22) PCT Filed: May 30, 2014

(86) PCT No.: PCT/US2014/040340
§ 371 (c)(1),
(2) Date: Nov. 24, 2015

(87) PCT Pub. No.: WO2014/194257
PCT Pub. Date: Dec. 4, 2014

(65) Prior Publication Data
US 2016/0107309 A1 Apr. 21, 2016

Related U.S. Application Data

(63) Continuation of application No. PCT/US2013/060225, filed on Sep. 17, 2013.
(Continued)

(51) Int. Cl.
*A61H 3/00* (2006.01)
*B25J 9/00* (2006.01)
(Continued)

(52) U.S. Cl.
CPC .............. *B25J 9/0006* (2013.01); *A61B 5/112* (2013.01); *A61B 5/6831* (2013.01); *A61H 1/024* (2013.01);
(Continued)

(58) Field of Classification Search
CPC . A61H 3/00; A61H 2201/1261; A25J 9/0015; A25J 9/006; G09B 19/0038; A61B 5/112; A61B 5/6831
See application file for complete search history.

(56) References Cited

U.S. PATENT DOCUMENTS 3,387,305 A 6/1968 Shafer
3,411,511 A 11/1968 Marino
(Continued)

FOREIGN PATENT DOCUMENTS

CN 1431084 A 7/2003
CN 1868434 B 11/2006
(Continued)

OTHER PUBLICATIONS

Ghodsi et al. "De novo Likelihood-based measures for comparing genome assemblies" in: BMC Research Notes 2013, Aug. 22, 2013—online retrieved on Oct. 25, 2016.
(Continued)

*Primary Examiner* — Timothy A Stanis
(74) *Attorney, Agent, or Firm* — Wolf, Greenfield & Sacks, P.C.

(57) ABSTRACT

A motion control system includes an actuator having an actuation member, the actuation member having a proximal end attached to the actuator on a first side of a joint and a distal end attached to an anchor element attachment point on a second side of the joint. A first sensor is configured to output signals defining a gait cycle and a second sensor is configured to output signals representing a tensile force in (Continued)

the at least one actuation member. A controller receives the output signals from the sensors and actuates the actuator, during a first portion of the gait cycle, to apply a force greater than a predetermined threshold tensile force to the anchor element attachment point via the actuation member to generate a beneficial moment about the joint and to automatically actuate the actuator.

19 Claims, 34 Drawing Sheets

Related U.S. Application Data

(60) Provisional application No. 61/829,686, filed on May 31, 2013, provisional application No. 61/873,433, filed on Sep. 4, 2013, provisional application No. 61/913,863, filed on Dec. 9, 2013, provisional application No. 61/928,281, filed on Jan. 16, 2014, provisional application No. 61/936,162, filed on Feb. 5, 2014, provisional application No. 61/977,880, filed on Apr. 10, 2014, provisional application No. 61/980,961, filed on Apr. 17, 2014.

(51) Int. Cl.
```
A63B 21/005      (2006.01)
A61H 1/02        (2006.01)
G09B 19/00       (2006.01)
A61B 5/11        (2006.01)
A61B 5/00        (2006.01)
B25J 9/10        (2006.01)
B25J 9/16        (2006.01)
A63B 24/00       (2006.01)
A63B 21/02       (2006.01)
A63B 21/00       (2006.01)
A63B 71/06       (2006.01)
F03G 7/00        (2006.01)
A63B 23/035      (2006.01)
A63B 23/04       (2006.01)
A63B 21/008      (2006.01)
```

(52) U.S. Cl.
CPC ......... *A61H 1/0244* (2013.01); *A61H 1/0266* (2013.01); *A61H 3/00* (2013.01); *A63B 21/0054* (2015.10); *B25J 9/104* (2013.01); *B25J 9/1694* (2013.01); *G09B 19/0038* (2013.01); *A61B 5/6812* (2013.01); *A61B 5/6828* (2013.01); *A61H 2003/001* (2013.01); *A61H 2003/007* (2013.01); *A61H 2201/123* (2013.01); *A61H 2201/1215* (2013.01); *A61H 2201/1238* (2013.01); *A61H 2201/1253* (2013.01); *A61H 2201/164* (2013.01); *A61H 2201/165* (2013.01); *A61H 2201/1628* (2013.01); *A61H 2201/1676* (2013.01); *A61H 2201/501* (2013.01); *A61H 2201/5046* (2013.01); *A61H 2201/5048* (2013.01); *A61H 2201/5061* (2013.01); *A61H 2201/5064* (2013.01); *A61H 2201/5084* (2013.01); *A61H 2201/5097* (2013.01); *A61H 2230/60* (2013.01); *A63B 21/008* (2013.01); *A63B 21/00178* (2013.01); *A63B 21/023* (2013.01); *A63B 21/152* (2013.01); *A63B 21/4009* (2015.10); *A63B 21/4013* (2015.10); *A63B 21/4015* (2015.10); *A63B 21/4025* (2015.10); *A63B 21/4047* (2015.10); *A63B 23/03541* (2013.01); *A63B 23/0405* (2013.01); *A63B 24/0087* (2013.01); *A63B 2071/068* (2013.01); *A63B 2071/0666* (2013.01); *A63B 2220/24* (2013.01); *A63B 2220/40* (2013.01); *A63B 2220/51* (2013.01); *A63B 2220/801* (2013.01); *A63B 2225/20* (2013.01); *A63B 2225/50* (2013.01); *A63B 2230/60* (2013.01); *F03G 7/005* (2013.01)

(56) References Cited

U.S. PATENT DOCUMENTS

| | | |
|---|---|---|
| 3,831,467 A | 8/1974 | Moore |
| 4,023,215 A | 5/1977 | Moore |
| 4,252,112 A | 2/1981 | Joyce |
| 4,370,977 A | 2/1983 | Mauldin et al. |
| 4,682,776 A | 7/1987 | Mitchell et al. |
| 4,697,808 A | 10/1987 | Larson et al. |
| 4,724,827 A | 2/1988 | Schenck |
| 4,760,850 A | 8/1988 | Phillips et al. |
| 5,020,790 A | 6/1991 | Beard et al. |
| 5,282,460 A | 2/1994 | Boldt |
| 5,485,402 A | 1/1996 | Smith et al. |
| 5,584,799 A | 12/1996 | Gray |
| 5,599,283 A | 2/1997 | Lindenmeyer et al. |
| 5,667,461 A | 9/1997 | Hall |
| 5,826,578 A | 10/1998 | Curchod |
| 5,865,714 A | 2/1999 | Marlowe |
| 5,865,770 A | 2/1999 | Schectman |
| 5,955,667 A | 9/1999 | Fyfe |
| 6,123,649 A | 9/2000 | Lee et al. |
| 6,129,691 A | 10/2000 | Ruppert |
| 6,168,634 B1 | 1/2001 | Schmitz |
| 6,213,922 B1 | 4/2001 | Afanasenko et al. |
| 6,500,138 B1 | 12/2002 | Irby et al. |
| 6,517,503 B1 | 2/2003 | Naft et al. |
| 6,633,783 B1 | 10/2003 | Dariush et al. |
| 6,635,024 B2 | 10/2003 | Hatton et al. |
| 6,666,831 B1 | 12/2003 | Edgerton et al. |
| 6,689,075 B2 | 2/2004 | West |
| 6,741,911 B2 | 5/2004 | Simmons |
| 6,783,555 B2 | 8/2004 | Kuhn et al. |
| 6,790,165 B2 | 9/2004 | Huang |
| 6,796,926 B2 | 9/2004 | Reinkensmeyer et al. |
| 6,812,624 B1 | 11/2004 | Pei et al. |
| 6,955,692 B2 | 10/2005 | Grundei |
| 6,989,669 B2 | 1/2006 | Low et al. |
| 7,034,432 B1 | 4/2006 | Pelrine et al. |
| 7,034,527 B2 | 4/2006 | Low et al. |
| 7,049,732 B2 | 5/2006 | Pei et al. |
| 7,056,297 B2 | 6/2006 | Dohnu et al. |
| 7,064,472 B2 | 6/2006 | Pelrine et al. |
| 7,090,650 B2 | 8/2006 | Ou et al. |
| 7,153,242 B2 | 12/2006 | Goffer |
| 7,153,246 B2 | 12/2006 | Koscielny et al. |
| 7,166,953 B2 | 1/2007 | Heim et al. |
| 7,190,141 B1 | 3/2007 | Ashrafiuon et al. |
| 7,199,501 B2 | 4/2007 | Pei et al. |
| 7,211,937 B2 | 5/2007 | Kornbluh et al. |
| 7,224,106 B2 | 5/2007 | Pei et al. |
| 7,229,390 B2 | 6/2007 | Fujii et al. |
| 7,233,097 B2 | 6/2007 | Rosenthal et al. |
| 7,252,644 B2 | 8/2007 | Dewald et al. |
| 7,259,503 B2 | 8/2007 | Pei et al. |
| 7,259,553 B2 | 8/2007 | Arns, Jr. et al. |
| 7,307,418 B2 | 12/2007 | Low et al. |
| 7,331,906 B2 | 2/2008 | He et al. |
| 7,341,295 B1 | 3/2008 | Veatch et al. |
| 7,355,519 B2 | 4/2008 | Grold et al. |
| 7,367,958 B2 | 5/2008 | McBean et al. |
| 7,368,862 B2 | 5/2008 | Pelrine et al. |
| 7,378,878 B2 | 5/2008 | Pelrine et al. |
| 7,390,309 B2 | 6/2008 | Dariush |
| 7,410,471 B1 | 8/2008 | Campbell et al. |
| 7,411,332 B2 | 8/2008 | Kornbluh et al. |
| 7,429,253 B2 | 9/2008 | Shimada et al. |
| 7,436,099 B2 | 10/2008 | Pei et al. |
| 7,445,606 B2 | 11/2008 | Rastegar et al. |
| 7,456,549 B2 | 11/2008 | Heim et al. |

(56) References Cited

U.S. PATENT DOCUMENTS

| | | |
|---|---|---|
| 7,476,185 B2 | 1/2009 | Drennan |
| 7,494,450 B2 | 2/2009 | Solomon |
| 7,521,840 B2 | 4/2009 | Heim |
| 7,521,847 B2 | 4/2009 | Heim |
| 7,537,573 B2 | 5/2009 | Horst |
| 7,549,969 B2 | 6/2009 | van den Bogert |
| 7,567,681 B2 | 7/2009 | Pelrine et al. |
| 7,578,799 B2 | 8/2009 | Thorsteinsson et al. |
| 7,595,580 B2 | 9/2009 | Heim |
| 7,598,651 B2 | 10/2009 | Kornbluh et al. |
| 7,598,652 B2 | 10/2009 | Kornbluh et al. |
| 7,626,319 B2 | 12/2009 | Heim |
| 7,650,204 B2 | 1/2010 | Dariush |
| 7,652,386 B2 | 1/2010 | Donelan et al. |
| 7,654,973 B2 | 2/2010 | Firsov |
| 7,679,267 B2 | 3/2010 | Heim |
| 7,684,896 B2 | 3/2010 | Dariush |
| 7,705,521 B2 | 4/2010 | Pelrine et al. |
| 7,737,685 B2 | 6/2010 | Low et al. |
| 7,750,532 B2 | 7/2010 | Heim |
| 7,758,481 B2 | 7/2010 | Drennan |
| 7,774,177 B2 | 8/2010 | Dariush |
| 7,775,999 B2 | 8/2010 | Brown |
| 7,785,279 B2 | 8/2010 | Sankai |
| 7,785,656 B2 | 8/2010 | Pei et al. |
| 7,787,646 B2 | 8/2010 | Pelrine et al. |
| 7,804,227 B2 | 9/2010 | Pelrine et al. |
| 7,857,774 B2 | 12/2010 | Sankai |
| 7,860,562 B2 | 12/2010 | Endo et al. |
| 7,883,546 B2 | 2/2011 | Kazerooni et al. |
| 7,887,471 B2 | 2/2011 | McSorley |
| 7,897,168 B2 | 3/2011 | Chen et al. |
| 7,911,761 B2 | 3/2011 | Biggs et al. |
| 7,915,790 B2 | 3/2011 | Heim et al. |
| 7,918,808 B2 | 4/2011 | Simmons |
| 7,921,541 B2 | 4/2011 | Pei et al. |
| 7,923,064 B2 | 4/2011 | Pelrien et al. |
| 7,923,902 B2 | 4/2011 | Heim |
| 7,947,004 B2 | 5/2011 | Kazerooni et al. |
| 7,952,261 B2 | 5/2011 | Lipton et al. |
| 7,985,193 B2 | 6/2011 | Thorsteinsson et al. |
| 7,977,923 B2 | 7/2011 | Pelrine et al. |
| 7,981,508 B1 | 7/2011 | Sharma et al. |
| 7,990,022 B2 | 8/2011 | Heim |
| 7,998,040 B2 | 8/2011 | Kram et al. |
| 8,048,007 B2 | 11/2011 | Roy |
| 8,057,410 B2 | 11/2011 | Angold et al. |
| 8,058,861 B2 | 11/2011 | Pelrine et al. |
| 8,060,337 B2 | 11/2011 | Kulach et al. |
| 8,075,633 B2 | 12/2011 | Herr et al. |
| 8,083,644 B2 | 12/2011 | Purdy et al. |
| 8,096,965 B2 | 1/2012 | Goffer et al. |
| 8,114,034 B2 | 2/2012 | Ikeuchi et al. |
| 8,125,755 B2 | 2/2012 | Garcia et al. |
| 8,127,437 B2 | 3/2012 | Lipton et al. |
| 8,142,370 B2 | 3/2012 | Weinberg et al. |
| 8,147,436 B2 | 4/2012 | Agrawal et al. |
| 8,164,232 B2 | 4/2012 | Kornbluh et al. |
| 8,183,739 B2 | 5/2012 | Heim |
| 8,222,799 B2 | 7/2012 | Polyakov et al. |
| 8,231,687 B2 | 7/2012 | Bedard et al. |
| 8,235,869 B2 | 8/2012 | Rastegar et al. |
| 8,246,559 B2 | 8/2012 | Hoffman et al. |
| 8,248,750 B2 | 8/2012 | Biggs et al. |
| 8,274,244 B2 | 9/2012 | Bhugra et al. |
| 8,283,839 B2 | 10/2012 | Heim |
| 8,287,477 B1 | 10/2012 | Herr et al. |
| 8,292,836 B2 | 10/2012 | Matsuoka et al. |
| 8,299,634 B2 | 10/2012 | Donelan et al. |
| 8,311,623 B2 | 11/2012 | Sanger |
| 8,316,526 B2 | 11/2012 | Pei et al. |
| 8,316,719 B2 | 11/2012 | Majidi et al. |
| 8,323,355 B2 | 12/2012 | Latour |
| 8,325,458 B2 | 12/2012 | Prahlad et al. |
| 8,348,875 B2 | 1/2013 | Goffer et al. |
| 8,376,971 B1 | 2/2013 | Herr et al. |
| 8,409,117 B2 | 4/2013 | Cheng et al. |
| 8,436,508 B2 | 5/2013 | Kornbluh et al. |
| 8,438,757 B2 | 5/2013 | Roser |
| 8,460,001 B1 | 6/2013 | Chuang |
| 8,467,904 B2 | 6/2013 | Dariush |
| 8,488,295 B2 | 7/2013 | Garcia et al. |
| 8,508,109 B2 | 8/2013 | Pelrine et al. |
| 8,551,029 B1 | 10/2013 | Herr et al. |
| 8,551,184 B1 | 10/2013 | Herr |
| 8,562,691 B2 | 10/2013 | Endo et al. |
| 8,564,926 B2 | 10/2013 | Prahlad et al. |
| 8,573,982 B1 | 11/2013 | Chuang |
| 8,585,620 B2 | 11/2013 | McBean et al. |
| 8,597,369 B2 | 12/2013 | Hansen et al. |
| 8,608,479 B2 | 12/2013 | Liu |
| 8,608,674 B2 | 12/2013 | Krebs et al. |
| 8,622,938 B2 | 1/2014 | Sankai |
| 8,663,133 B2 | 3/2014 | Johnson et al. |
| 8,665,578 B2 | 3/2014 | Pelrine et al. |
| 8,679,575 B2 | 3/2014 | Biggs et al. |
| 8,715,208 B2 | 5/2014 | Hodgins et al. |
| 8,766,925 B2 | 6/2014 | Perlin et al. |
| 8,764,850 B2 | 7/2014 | Hansen et al. |
| 8,773,148 B2 | 7/2014 | Sankai et al. |
| 8,847,611 B2 | 9/2014 | Ulmen et al. |
| 8,905,955 B2 | 12/2014 | Goffer et al. |
| 8,920,517 B2 | 12/2014 | Smith et al. |
| 8,926,534 B2 | 1/2015 | McBean et al. |
| 8,938,289 B2 | 1/2015 | Einav et al. |
| 8,961,439 B2 | 2/2015 | Yang et al. |
| 8,975,888 B2 | 3/2015 | Pelrine et al. |
| 8,981,621 B2 | 3/2015 | Pelrine et al. |
| 8,986,233 B2 | 3/2015 | Aoki et al. |
| 9,044,346 B2 | 6/2015 | Langlois et al. |
| 9,072,941 B2 | 7/2015 | Duda et al. |
| 9,101,323 B2 | 8/2015 | Einarsson et al. |
| 9,144,528 B2 | 9/2015 | Agrawal et al. |
| 9,149,370 B2 | 10/2015 | Herr et al. |
| 9,195,794 B2 | 11/2015 | Dariush |
| 9,198,821 B2 | 12/2015 | Unluhisarcikli et al. |
| 9,221,177 B2 | 12/2015 | Herr et al. |
| 9,227,108 B1 | 1/2016 | Chuang |
| 9,228,822 B2 | 1/2016 | Majidi et al. |
| 9,231,186 B2 | 1/2016 | Busgen et al. |
| 9,266,233 B2 | 2/2016 | Kornbluh et al. |
| 9,333,097 B2 | 5/2016 | Herr et al. |
| 9,351,900 B2 | 5/2016 | Walsh et al. |
| 9,387,096 B2 | 6/2016 | Sverrisson et al. |
| 9,403,272 B2 | 8/2016 | Kornbluh et al. |
| 9,427,864 B2 | 8/2016 | Kornbluh et al. |
| 10,028,881 B2 | 7/2018 | Yamamoto et al. |
| 10,115,319 B2 | 10/2018 | Asbeck et al. |
| 10,278,883 B2 | 5/2019 | Walsh et al. |
| 10,427,293 B2 | 10/2019 | Asbeck et al. |
| 10,434,030 B2 | 10/2019 | Asbeck et al. |
| 2001/0007845 A1 | 7/2001 | Afanasenko et al. |
| 2003/0009120 A1 | 1/2003 | MacAllister |
| 2003/0030397 A1 | 2/2003 | Simmons |
| 2003/0064869 A1 | 4/2003 | Reinkensmeyer et al. |
| 2003/0092545 A1 | 5/2003 | Koscielny et al. |
| 2003/0096310 A1 | 5/2003 | Hansen et al. |
| 2003/0120183 A1 | 6/2003 | Simmons |
| 2003/0125781 A1 | 7/2003 | Dohno et al. |
| 2004/0043879 A1 | 3/2004 | Huang |
| 2004/0064195 A1 | 4/2004 | Herr |
| 2004/0087418 A1 | 5/2004 | Eldridge |
| 2004/0106881 A1* | 6/2004 | McBean et al. ... A61B 5/04888 601/5 |
| 2004/0116260 A1 | 7/2004 | Drennan |
| 2004/0147378 A1 | 7/2004 | Conklin et al. |
| 2004/0191321 A1 | 9/2004 | Guan et al. |
| 2004/0204294 A2 | 10/2004 | Wilkinson et al. |
| 2005/0010150 A1 | 1/2005 | Firsov |
| 2005/0049865 A1 | 3/2005 | Yaxin et al. |
| 2005/0070834 A1 | 3/2005 | Herr et al. |
| 2005/0101448 A1 | 5/2005 | He et al. |
| 2005/0107725 A1 | 5/2005 | Wild |
| 2005/0157893 A1 | 7/2005 | Pelrine et al. |

(56) References Cited

U.S. PATENT DOCUMENTS

| | | |
|---|---|---|
| 2005/0184878 A1 | 8/2005 | Grold et al. |
| 2005/0288157 A1 | 12/2005 | Santos-Munne et al. |
| 2006/0079817 A1 | 4/2006 | Dewald et al. |
| 2006/0108755 A1 | 5/2006 | Smyler et al. |
| 2006/0136206 A1 | 6/2006 | Ariu et al. |
| 2006/0192465 A1 | 8/2006 | Kornbluh et al. |
| 2006/0249315 A1 | 11/2006 | Herr et al. |
| 2007/0004570 A1 | 1/2007 | Afanasenko et al. |
| 2007/0004571 A1 | 1/2007 | Gonzalez |
| 2007/0066918 A1 | 3/2007 | Dewald et al. |
| 2007/0111868 A1 | 5/2007 | Fujii et al. |
| 2007/0123997 A1 | 5/2007 | Herr et al. |
| 2007/0135279 A1 | 6/2007 | Purdy et al. |
| 2007/0276270 A1 | 11/2007 | Tran |
| 2008/0000317 A1* | 1/2008 | Patton .................. A61F 5/0102 74/500.5 |
| 2008/0039756 A1 | 2/2008 | Thorsteinsson et al. |
| 2008/0062589 A1 | 3/2008 | Drabing |
| 2008/0071386 A1 | 3/2008 | McBean et al. |
| 2008/0075930 A1 | 3/2008 | Kornbluh et al. |
| 2008/0097269 A1 | 4/2008 | Weinberg et al. |
| 2008/0156363 A1 | 7/2008 | Ikeuchi et al. |
| 2008/0173365 A1 | 7/2008 | Unger et al. |
| 2008/0218132 A1 | 9/2008 | Pelrine et al. |
| 2008/0224564 A1 | 9/2008 | Pelrine et al. |
| 2008/0255488 A1 | 10/2008 | Agrawal et al. |
| 2008/0289952 A1 | 11/2008 | Pelrine et al. |
| 2008/0294019 A1 | 11/2008 | Tran |
| 2008/0300118 A1 | 12/2008 | Wehrell |
| 2009/0042702 A1 | 2/2009 | Toronto et al. |
| 2009/0221928 A1 | 9/2009 | Einav et al. |
| 2009/0255531 A1 | 10/2009 | Johnson et al. |
| 2009/0256817 A1 | 10/2009 | Perlin et al. |
| 2009/0306548 A1 | 12/2009 | Bhugra et al. |
| 2009/0319054 A1 | 12/2009 | Sankai |
| 2010/0000547 A1 | 1/2010 | Johnson et al. |
| 2010/0007240 A1 | 1/2010 | Kornbluh et al. |
| 2010/0024180 A1 | 2/2010 | Pei et al. |
| 2010/0026143 A1 | 2/2010 | Pelrine et al. |
| 2010/0030343 A1 | 2/2010 | Hansen et al. |
| 2010/0038983 A1 | 2/2010 | Bhugra et al. |
| 2010/0056966 A1 | 3/2010 | Toth |
| 2010/0144490 A1 | 6/2010 | Purdy et al. |
| 2010/0152630 A1 | 6/2010 | Matsuoka et al. |
| 2010/0185259 A1 | 7/2010 | Shiba et al. |
| 2010/0185301 A1 | 7/2010 | Hansen et al. |
| 2010/0204804 A1 | 8/2010 | Garrec |
| 2010/0271051 A1 | 10/2010 | Sankai et al. |
| 2010/0274364 A1 | 10/2010 | Pacanowsky |
| 2010/0280628 A1 | 11/2010 | Sankai |
| 2010/0286796 A1 | 11/2010 | Clausen |
| 2010/0298834 A1 | 11/2010 | Hildebrandt |
| 2010/0319215 A1 | 12/2010 | Roser |
| 2010/0324698 A1 | 12/2010 | Sverrisson et al. |
| 2011/0004322 A1 | 1/2011 | Sankai |
| 2011/0009793 A1 | 1/2011 | Lucero |
| 2011/0022349 A1 | 1/2011 | Kulach et al. |
| 2011/0033835 A1 | 1/2011 | Endo et al. |
| 2011/0025170 A1 | 2/2011 | Rosenthal et al. |
| 2011/0040216 A1 | 2/2011 | Herr et al. |
| 2011/0062948 A1 | 3/2011 | Arns, Jr. et al. |
| 2011/0071647 A1 | 3/2011 | Mahon |
| 2011/0093089 A1 | 4/2011 | Martin |
| 2011/0105966 A1 | 5/2011 | Kazerooni et al. |
| 2011/0150966 A1 | 5/2011 | Kazerooni et al. |
| 2011/0152696 A1 | 6/2011 | Ryan |
| 2011/0154641 A1 | 6/2011 | Pelrine et al. |
| 2011/0155307 A1 | 6/2011 | Pelrine et al. |
| 2011/0174524 A1 | 7/2011 | Sharma et al. |
| 2011/0193362 A1 | 8/2011 | Prahlad et al. |
| 2011/0201978 A1 | 8/2011 | Jeon et al. |
| 2011/0209337 A1 | 9/2011 | Pei et al. |
| 2011/0245738 A1 | 10/2011 | Agrawal et al. |
| 2011/0282255 A1 | 11/2011 | Nace |
| 2011/0295384 A1 | 12/2011 | Herr et al. |
| 2011/0295385 A1 | 12/2011 | Herr et al. |
| 2011/0313331 A1 | 12/2011 | Dehez et al. |
| 2012/0019223 A1 | 1/2012 | Pelrine et al. |
| 2012/0023638 A1 | 2/2012 | Leicester |
| 2012/0056903 A1 | 3/2012 | Shinohara et al. |
| 2012/0071797 A1 | 3/2012 | Aoki et al. |
| 2012/0100286 A1 | 4/2012 | Sharma et al. |
| 2012/0109031 A1 | 5/2012 | Vollbrecht |
| 2012/0120544 A1 | 5/2012 | Pelrine et al. |
| 2012/0128960 A1 | 5/2012 | Busgen et al. |
| 2012/0165709 A1 | 6/2012 | Goffer et al. |
| 2012/0169184 A1 | 7/2012 | Pelrine et al. |
| 2012/0177934 A1 | 7/2012 | Vogel et al. |
| 2012/0179075 A1 | 7/2012 | Perry et al. |
| 2012/0181896 A1 | 7/2012 | Kronbluh et al. |
| 2012/0185052 A1 | 7/2012 | Lefeber |
| 2012/0209152 A1 | 8/2012 | Cordo |
| 2012/0238914 A1 | 9/2012 | Goldfield et al. |
| 2012/0248942 A1 | 10/2012 | Biggs et al. |
| 2012/0253234 A1 | 10/2012 | Yang et al. |
| 2012/0271207 A1 | 10/2012 | Schoen et al. |
| 2012/0279175 A1 | 11/2012 | Biggs et al. |
| 2012/0289870 A1 | 11/2012 | Hsiao-Wecksler et al. |
| 2012/0330198 A1 | 12/2012 | Patoglu |
| 2013/0013085 A1 | 1/2013 | Smith et al. |
| 2013/0019749 A1 | 1/2013 | Hufton et al. |
| 2013/0040783 A1 | 2/2013 | Duda et al. |
| 2013/0041617 A1 | 2/2013 | Pease et al. |
| 2013/0045530 A1 | 2/2013 | Gracias et al. |
| 2013/0058001 A1 | 3/2013 | Prahlad et al. |
| 2013/0079686 A1 | 3/2013 | Sessions |
| 2013/0093439 A1 | 4/2013 | Ulmen et al. |
| 2013/0102935 A1 | 4/2013 | Kazerooni et al. |
| 2013/0123672 A1 | 5/2013 | Goffer et al. |
| 2013/0130866 A1 | 5/2013 | Ivehrell |
| 2013/0131555 A1 | 5/2013 | Hook |
| 2013/0158444 A1 | 6/2013 | Herr et al. |
| 2013/0165817 A1 | 6/2013 | Horst et al. |
| 2013/0179154 A1 | 7/2013 | Okuno |
| 2013/0186699 A1 | 7/2013 | Prahald et al. |
| 2013/0211295 A1 | 8/2013 | Johnson et al. |
| 2013/0225371 A1 | 8/2013 | Harrer et al. |
| 2013/0226048 A1* | 8/2013 | Unluhisarcikli ......... A61H 3/00 601/34 |
| 2013/0230667 A1 | 9/2013 | Sharma et al. |
| 2013/0237884 A1 | 9/2013 | Kazerooni et al. |
| 2013/0245512 A1 | 9/2013 | Goffer et al. |
| 2013/0253385 A1 | 9/2013 | Goffer et al. |
| 2013/0261513 A1 | 10/2013 | Goffer et al. |
| 2013/0261766 A1 | 10/2013 | Langlois et al. |
| 2013/0268256 A1 | 10/2013 | Dariush |
| 2013/0274640 A1 | 10/2013 | Butters et al. |
| 2013/0288863 A1 | 10/2013 | Yamamoto et al. |
| 2013/0289452 A1 | 10/2013 | Smith et al. |
| 2013/0296746 A1 | 11/2013 | Herr et al. |
| 2013/0307370 A1 | 11/2013 | Jenninger et al. |
| 2013/0310979 A1 | 11/2013 | Herr et al. |
| 2013/0312541 A1 | 11/2013 | Majidi et al. |
| 2013/0328440 A1 | 12/2013 | Kornbluh et al. |
| 2014/0046455 A1 | 2/2014 | Herr et al. |
| 2014/0194781 A1 | 7/2014 | Einarsson et al. |
| 2014/0213951 A1 | 7/2014 | Pietrusisnki et al. |
| 2014/0277739 A1* | 9/2014 | Kornbluh ............... B25J 9/0006 700/260 |
| 2014/0358040 A1 | 12/2014 | Kim et al. |
| 2015/0099945 A1 | 4/2015 | Hawkins, III et al. |
| 2015/0142130 A1 | 5/2015 | Goldfarb et al. |
| 2015/0173993 A1 | 6/2015 | Walsh et al. |
| 2015/0266180 A1 | 9/2015 | Kornbluh et al. |
| 2015/0266181 A1 | 9/2015 | Kornbluh et al. |
| 2015/0297934 A1 | 10/2015 | Agrawal et al. |
| 2015/0298765 A1 | 10/2015 | Golden, Jr. |
| 2015/0321339 A1 | 11/2015 | Asbeck et al. |
| 2015/0321399 A1 | 11/2015 | Hong et al. |
| 2016/0346156 A1 | 1/2016 | Walsh et al. |
| 2016/0101516 A1 | 4/2016 | Kornbluh et al. |
| 2016/0101517 A1 | 4/2016 | Kornbluh et al. |
| 2016/0107309 A1 | 4/2016 | Walsh et al. |
| 2016/0220438 A1 | 8/2016 | Walsh et al. |

(56) References Cited

U.S. PATENT DOCUMENTS

| | | |
|---|---|---|
| 2016/0278948 A1 | 9/2016 | Piercy et al. |
| 2016/0284231 A1 | 9/2016 | Walsh et al. |
| 2017/0027735 A1 | 2/2017 | Walsh et al. |
| 2017/0163435 A1 | 6/2017 | Ehsani et al. |
| 2017/0176167 A1 | 6/2017 | Keller et al. |
| 2017/0202724 A1 | 7/2017 | Walsh et al. |
| 2018/0008502 A1 | 1/2018 | Asbeck et al. |
| 2018/0056104 A1 | 3/2018 | Cromie et al. |
| 2018/0370020 A1 | 12/2018 | Murakami et al. |
| 2019/0008714 A1 | 1/2019 | Murakami et al. |
| 2019/0021933 A1 | 1/2019 | Murakami et al. |
| 2019/0029912 A1 | 1/2019 | Murakami et al. |
| 2019/0060156 A1 | 2/2019 | Swift et al. |
| 2019/0060157 A1 | 2/2019 | Lamb et al. |
| 2019/0070062 A1 | 3/2019 | O'Donnell et al. |

FOREIGN PATENT DOCUMENTS

| | | |
|---|---|---|
| CN | 202342034 | 7/2012 |
| CN | 101175456 | 3/2013 |
| CN | 102327173 | 5/2013 |
| DE | 19944139 | 4/2001 |
| EP | 0016268 | 10/1980 |
| EP | 0141640 | 10/1984 |
| EP | 0302148 | 2/1989 |
| EP | 0509723 A1 | 10/1992 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |
| JP | H07163607 A | 6/1995 |
| JP | 2002301124 A | 10/2002 |
| JP | 2005000500 A | 1/2005 |
| JP | 2007000391 A | 1/2007 |
| JP | 2008067762 | 3/2008 |
| JP | 4345025 | 10/2009 |
| JP | 2010042069 A | 2/2010 |
| JP | 2010-051416 | 3/2010 |
| JP | 4424269 | 3/2010 |
| JP | 2010075656 A | 4/2010 |
| JP | 4582523 | 11/2010 |
| JP | 2011/036375 | 2/2011 |
| JP | 4848260 | 12/2011 |
| JP | 2012/192013 | 10/2012 |
| JP | 2013146328 A | 8/2013 |
| JP | 2013-208397 A | 10/2013 |
| JP | 2014018536 A | 2/2014 |
| JP | 2014034145 A1 | 3/2014 |
| WO | WO 00/12041 A2 | 3/2000 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011/008934 | 1/2011 |
| WO | WO2011/026086 | 3/2011 |
| WO | WO2011/030641 | 3/2011 |
| WO | 2011126985 A2 | 10/2011 |
| WO | 2012014164 A2 | 2/2012 |
| WO | WO2012/050938 | 4/2012 |
| WO | WO2012/103073 | 8/2012 |
| WO | WO2012/124328 | 9/2012 |
| WO | WO2012/178171 | 12/2012 |
| WO | WO2013/019749 | 2/2013 |
| WO | WO 2013/019749 | 2/2013 |
| WO | 2013033669 A2 | 3/2013 |
| WO | WO2013/033669 | 3/2013 |
| WO | WO2013/044226 | 3/2013 |
| WO | 2013049658 A1 | 4/2013 |
| WO | WO 2013/146231 A1 | 10/2013 |
| WO | WO2014/109799 | 7/2014 |
| WO | WO2014/194257 | 12/2014 |
| WO | WO 2015/074070 A1 | 5/2015 |
| WO | WO2015/120186 | 8/2015 |
| WO | WO2015/157731 | 10/2015 |
| WO | WO2015/088863 | 12/2015 |
| WO | WO 2016/044251 A1 | 3/2016 |
| WO | WO2016/089466 | 6/2016 |
| WO | 2017040669 | 3/2017 |
| WO | 2017160751 A1 | 9/2017 |
| WO | 2018017436 A1 | 1/2018 |

OTHER PUBLICATIONS

Malcolm, Philippe et al., "Fast Exoskeleton Optimization" Science, vol. 356, Issue 6344, pp. 1230-1231, Jun. 23, 2017.

Polonen et al. "Automatic Intensity Quantification of Fluorescence Targets from microscope Images with Maximum Likelihood Estimation" 17th European Signal Processing Conference, Aug. 24-28, 2009—retrieved online Oct. 25, 2016.

Zhang, Juanjuan et al., "Human-in-the-Loop Optimization of Exoskeleton Assistance During Walking", Science, vol. 356, pp. 1280-1284, Jun. 23, 2017.

PCT International Search Report and Written Opinion in International Application No. PCT/US2015/051107, dated Aug. 5, 2016.

PCT International Search Report and Written Opinion in International Application No. PCT/US2016/049706, dated Nov. 29, 2016.

Extended European Search Report issued in European Application No. 14803880.5 dated May 19, 2017.

PCT International Search Report and Written Opinion in International Application No. PCT/US2017/022150, dated Jun. 9, 2017.

PCT International Search Report and Written Opinion, issued in International Application No. PCT/US2017/042286, dated Sep. 28, 2017.

Supplementary European Search Report issued in European Application No. 15 77 6544 dated Oct. 20, 2017.

USPTO Office Action in U.S. Appl. No. 14/660,704 dated Feb. 7, 2018.

Extended European Search Report issued in European Application No. 13871010.8 dated Sep. 2, 2016.

Extended European Search Report issued in European Application No. 15746146.8 dated Feb. 27, 2018.

PCT International Search Report issued in International Application No. PCT/US2014/040340 dated Oct. 31, 2014.

PCT International Written Opinion issued is International Application No. PCT/US2014/040340 dated Oct. 31, 2014.

Banala, S. K. et al., "Active leg exoskeleton (alex) for gait rehabilitation of motor-impaired patients," in Proc. 2007 IEEE 10th Int. Cnf. Rehabil robotics, pp. 401-407, Jun. 2007.

Browning, R. C. et al., "The effects of adding mass to the legs on the energetics and biomechanics of walking," Medicine and science in sports and exercise, col. 39, p. 515, 2007.

Chu, A. et al, On the biomimetric design of the Berkeley lower extremity exoskeleton (BLEEX), Proc 2005 in IEEE Int. Conf. Robotics and Automation (ICRA) (IEEE Press, Barcelona, Spain, Apr. 2006), pp. 4356-4363.

Clevertex,: Development of strategic Master Plan for the transformation of the traditional textile and clothing into a knowledge driven industrial sector by 2015, 160 pages, dated prior to Jul. 2014.

Collins, S., et al., Efficient Bipedal Robots Based on Passive-Dynamic Walkers. Science, 307(5712): p. 1082-1085, 2005.

Cool, J.C. Biomechanics of orthoses for the subluxed shoulder. Prosthetics & Orthotics International; 13:90-6, 1989.

Da Silva, A. F. et al., "FBG Sensing Glove for Monitoring Hand Posture," IEEE Sensors Journal, . . . , vol. 11, No. 10, pp. 2442-2448, Oct. 2011. [Online]. Available: http://ieeexplore.ieee.org/xpls/absall.jsp?arnumber=5742669.

De Rossi, D. et al., "Wearable technology for biomechanics: e-textile or micromechanical sensors?" IEEE engineering in medicine and biology magazine, vol. 29, No. 3, pp. 37-43, May/Jun. 2010. [Online]. Available: http://www.ncbi.nlm.nih.gov/pubmed/20659856.

(56) References Cited

OTHER PUBLICATIONS

Delp, S. L. et al., "OpenSim: open-source software to create and analyze dynamic simulations of movement." IEEE transactions on bio-medical engineering, vol. 54, No. 11, pp. 1940-50, Nov. 2007. [Online]. Available: http://www.ncbi.nlm.nih.gov/pubmed/18018689.
Dollar, A. M. et al., "Lower extremity exoskeletons and active orthoses: Challenges and state-of-the-art,", IEEE Transactions on Robotics, vol. 24, No. 1, pp. 144-158, Feb. 2008.
Erk, K. A. et al., "Strain stiffening in synthetic and biopolymer networks," Biomacromolecules, vol. 11, No. 5, pp. 1358-1363, May 2010.
Farris D.J., et al., Human medial gastrocnemius force-velocity behavior shifts with locomotion speed and Proc Natl Acad Sci USA. Jan. 2012; 109:977-982.
Ferris, D. P. et al., "Robotic lower limb exoskeletons using proportional myoelectric control," in EMBC 2009, Annual International Conference of the IEEE Engineering in Medicine and Biology Society, 2009.
Ferris, D.P. et al., A Physiologist's Perspective on Robotic Exoskeletons for Human Locomotion. Int. J HR, 4(3): p. 507-528, 2007.
Gibbs, P. et al.: Wearable Conductive Fiber Sensors for Multi-Axis Human Joint Angle Measurements. Journal of NeuroEngineering and Rehabilitation, Mar. 2, 2005.
Goodvin, C.I.: Development of a Real-time Spinal Motion Inertial Measurement System for Vestibular Disorder Application, University of Victoria, 155 pages, date 2003.
Gregorczyk, K. N., et al., The effects of a lower body exoskeleton load carriage assistive device on oxygen consumption and kinematics during walking with loads, in 25th Army Sci. Conf., Florida, USA, 2006.
Hallemans, A. et al.: 3D joint dynamics of walking in toddlers. A cross-sectional study spanning the first rapid development phase of walking. Gait & Posture, 22:107-118, 2005.
Kadaba, M. P., et al., "Measurement of lower extremity kinematics during level walking." Journal of orthopaedic research: official publication of the Orthopaedic Research Society, vol. 8, No. 3, pp. 383-392, May 1990. [Online]. Available: http://www.ncbi.nlm.nih.gov/pubmed/2324857.
Kawamoto, H., et al., Power assist method for HAL-3 using EMG-based feedback controller. in Systems, Man and Cybernetics, 2003. IEEE International Conference on. 2003.
Kim, D.-H. et al., "Epidermal electronics." Science, vol. 333, No. 6044, pp. 838-843, Aug. 2011. [Online] Available: http://www.sciencemag.org/cgi/doi/10.1126/science.1206157.
Kramer, R. K. et al., "Soft curvature sensors for joint angle proprioception," in 2011 IEEE/RSJ International Conference on Intelligent Robots and Systems. IEEE, pp. 1919-1926, Sep. 2011. [Online]. Available: http://ieeexplore.ieee.org/lpdocs/epic03/wrapper.htm?arnumber=6094701.
Kramer, R. K. et al., "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.
Kulyukin, V. A.: Advances in Human-Robot Interaction, 354 pages, Dec. 2009.
Lee, S. W. et al.: Biomimetic Approach Enables Functional Movements of Hand Post Stroke: A Pilot Study, 2 pages, dated 2012.
Lipomi, D. J. et al., "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.
Majidi, C. et al., "A non-differential elastomer curvature sensor for softer-than-skin electronics," Smart Materials and Structures, vol. 20, No. 10, p. 105017, Oct 2011. [Online]. Available: http://stacks.iop.org/0964-1726/20/i=10/a=105017?key=cro ssref. 0cca7e97d6ad7110bcdcaf45f30f3b60.
Mattila, H. R., Intelligent textiles and clothing, Woodhead Publishing Limited, 525 pages, © 2006.
McGeer, T., Passive Bipedal Running. Proceedings of the Royal Society of London. Series B, Biological Sciences, 240(1297): p. 107-134, May 1990.
Newman, D. J. et al., Astronaut Bio-Suit System to Enable Planetary Exploration. In International Astronautical Conference, Vancouver, Canada, Oct. 2004.
Park, Y. L. et al., Active Modular Elastomer Sleeve for Soft Wearable Assistance Robots, 2012 IEEE/RSJ International Con. On Intelligent Robots and Systems Vilamoura, Algarve, Portugal, 8 pages, Oct. 7-12, 2012.
Park, Y.-L., et al., "Design and Fabrication of Soft Artificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber=6203551.
Park, Y.-L., "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=125029?key=crossref. 84cffc44789ba7bde0bdfd169e25af91.
Park, Y.-L., et al.: Bio-inspired Active Soft Orthotic Device for Ankle Foot Pathologies, 2011 IEEE/RSJ International Conference on Intelligent Robots and Systems, San Francisco, CA, USA, 8 pages, Sep. 25-30, 2011.
Pereira da Fonseca, P. F.: Validation of two types of textile electrodes for electrocardiography and electromyography measurement applications, 126 pages, dated Jul. 2012.
Pratt, J. et al., The RoboKnee: An exoskeleton for enhancing strength and endurance during walking, in IEEE Int. Conf. Robotics and Automation (ICRA), New Orleans, USA (IEEE Press), pp. 2430-2435, Apr. 2004.
Quintero, H. A. et al., "Control and Implementation of a Powered Lower Limb Orthosis to Aid Walking in Paraplegic Individuals," in IEEE International Conference on Rehabilitation Robotics, Switzerland, pp. 1-6, Jun. 29-Jul. 1, 2011.
Ramuz, M. et al., "Transparent, Optical, Pressure-Sensitive Artificial Skin for Large-Area Stretchable Electronics," Advanced Materials, May 2012. [Online]. Available: http://doi.wiley.com/10.1002/adma.201200523.
Reid, S. A. et al., "Biomechanical assessment of rucksack shoulder strap attachment location: effect on load distribution to the torso," presented at the RTO HFM specialists' Meeting on "Soldier Mobility: Innovations in Load Carriage System Design and Evaluation," NATO-RTO Meeting Proceedings: MP-056 (Neuilly-sur-Seine: NATO). Jun. 1-6, 2000.
Royer, T.D. et al., (2005) Manipulations of Leg Mass and Moment of Inertia: Effects on Energy Cost of Walking, Medicine & Science in Sports & Exercise. vol. 37. No. 4: p. 649-p. 656, 2005.
Salvendy, G.: Smart Clothing Technology and Applications, Human Factors and Ergonomics, by Taylor and Francis Group, LLC, 290 pages, © 2010.
Schiele, A. "Ergonomics of Exoskeletons: Objective Performance Metrics" in Euro Haptics conference and symposium on Haptic Interfaces for Virtual Environmental Teleoperator Systems, Salt Lake City, UT, USA, Mar. 2009.
Scilingo, E. P. et al., "Strain-sensing fabrics for wearable kinaesthetic-like systems," IEEE Sensors Journal, vol. 3, No. 4, pp. 460-467, Aug. 2003. [Online]. Available: http://ieeexplore.ieee. org/lpdocs/epic03/wrapper.htm?arnumber=1226639.
Silva, H. R., et al.: Wireless Hydrotherapy Smart-Suit Network for Posture Monitoring, 5 pages, dated 2007.
Strauser, K. A. et al., The development and testing of a human machine interface for a mobile medical exoskeleton? in IEEE Int Conf, Intelligent Robots and Systems, San Francisco, CA. USA, Sep. 2011.
Tesconi, M., et al., "Wearable sensorized system for analyzing the lower limb movement during rowing activity," 2007 IEEE International Symposium on Industrial Electronics, pp. 2793-2796, Jun. 2007. [Online]. Available: http://ieeexplore.ieee.org/lpdocs/epic03/wrapper.htm?arnumber=4375052.

(56) References Cited

OTHER PUBLICATIONS

Tiwana, M. I., et al., "A review of tactile sensing technologies with applications in biomedical engineering," Sensors and Actuators A: Physical, vol. 179, pp. 17-31, Jun. 2012. [Online]. Available: http://linkinghub.elsevier.com/retrieve/pii/S0924424712001641.
Vogt, D. M., et al., Design and Characterization of a Soft Multi-Axis Force Sensor Using Embedded Microfludic Channels, IEEE Sensors Journal, vol. 13. No. 10, 9 pages, Oct. 2013.
Walsh, C. J., et al., A Quasi-Passive Leg Exoskeleton for Load Carrying Augmentation. International Journal of Humanoid Robotics, Special Issue: Active Exoskeletons, 4(3): 487-506, 2007.
Wehner, M., 2012 "Man to Machine, Applications in Electromyography," EMG Methods for Evaluation Muscle and Nerve Functions. Intech Publishing, Sep. 13, 2012 http://intechopen.com/articles/show/title/man-to-machine-applications-in-electromyography.
Wehner, M., et al., "Experimental characterization of components for active soft orthotics," in Proc. IEEE Int. Conf. Biomed. Rob. Biomechatron., Roma, Italy, Jun. 2012.
Wehner, M., et al., "Lower Extremity Exoskeleton Reduces Back Forces in Lifting" ASME Dynamic Systems and Control Conference, Hollywood, California, USA pp. 49-56, Oct.12-14, 2009.
Woodman, O.J. "An introduction to inertial navigation," Technical Report UCAM-CL-TR-696, Aug. 2007.
Yamada, T. et al., "A stretchable carbon nanotube strain sensor for human-motion detection." Nature Nanotechnology, vol. 6, No. 5 pp. 296-301, May 2011. [Online]. Available: http://ncbi.nlm.nih.gov/pubmed/21441912.
Zhang, R. et al., "Carbon nanotube polymer coatings for textile yarns with good strain sensing capability," Sensors and Actuators A: Physical, vol. 179, pp. 83-91, Jun. 2012. [Online]. Available: http://linkinghub.elsevier.com/retrieve/pii/S0924424712001938.
Zoss, A.B., et al., Biomechanical design of the Berkeley lower extremity exoskeleton (BLEEX), IEE/ASME Transactions on Mechatronics, 11(2): p. 128-138, Apr. 2006.
PCT International Search Report, issued in International Application No. PCT/EP2003/012123, dated Jun. 22, 2004.
PCT International Search Report, issued in International Application No. PCT/US2013/060225, dated May 27, 2014.
PCT International Written Opinion, in International Application No. PCT/US2013/060225, dated May 27, 2014.
PCT International Written Opinion, in International Application No. PCT/US2014/040340, dated Oct. 31, 2014.
PCT International Search Report, issued in International Application No. PCT/US2014/068462, dated May 22, 2015.
PCT International Written Opinion, in International Application No. PCT/US2014/068462, dated May 22, 2015.
PCT International Search Report, issued in International Application No. PCT/US2015/014672, dated Jul. 6, 2015.
PCT International Written Opinion, in International Application No. PCT/US2015/014672, dated Jul. 6, 2015.
PCT International Search Report, issued in International Application No. PCT/US2015/025472, dated Sep. 4, 2015.
PCT International Written Opinion, in International Application No. PCT/US2015/025472, dated Sep. 4, 2015.
PCT International Search Report and Written Opinion issued in International Application PCT/US2015/014672 dated Aug. 5, 2016.
USPTO Office Action in U.S. Appl. No. 14/660,704 dated Jun. 28, 2018.
USPTO Office Action in U.S. Appl. No. 15/117,034 dated Oct. 5, 2018.
USPTO Office Action in U.S. Appl. No. 14/660,704 dated Nov. 8, 2018.
International Search Report and Written Opinion for International Application No. PCT/US2019/033143, dated Oct. 9, 2019.
International Search Report and Written Opinion for International Application No. PCT/US2018/022494, dated Jun. 8, 2018.
Bae et al, A Soft Exosuit for Patients with Stroke: Feasibility study with a mobile off-board actuation unit. 2015 IEEE International Conference on Rehabilitation Robotics (ICORR). Aug. 11, 2015; 131-8.
Laughton et al., Effect of Strike Pattern and Orthotic Intervention on Tibial Shock During Running. Journal of Applied Biomechanics. May 1, 2003; 19(2): 153-68.
Lenhart et al., Increasing Running Step Rate Reduces Patellofemoral Joint Forces. Medicine & Science in Sports & Exercise. Mar. 2014, 46(3): 557-64.
Lieberman et al., Effects of stride frequency and foot position in landing on braking force, hip torque, impact peak force and metabolic cost of running in humans. Journal of Experimental Biology. Nov. 1, 2015; 218(21):3406-14.
Sinclair et al., Determination of Gait Events Using an Externally Mounted Shank Accelerometer. Journal of Applied Biomechanics. Feb. 1, 2013; 29(1): 118-22.
Royer et al., Manipulations of Leg Mass and Moment of Inertia: Effects on Energy Cost of Walking. Medicine & Science in Sports & Exercise. Apr. 1, 2005; 37(4): 649-56.

\* cited by examiner

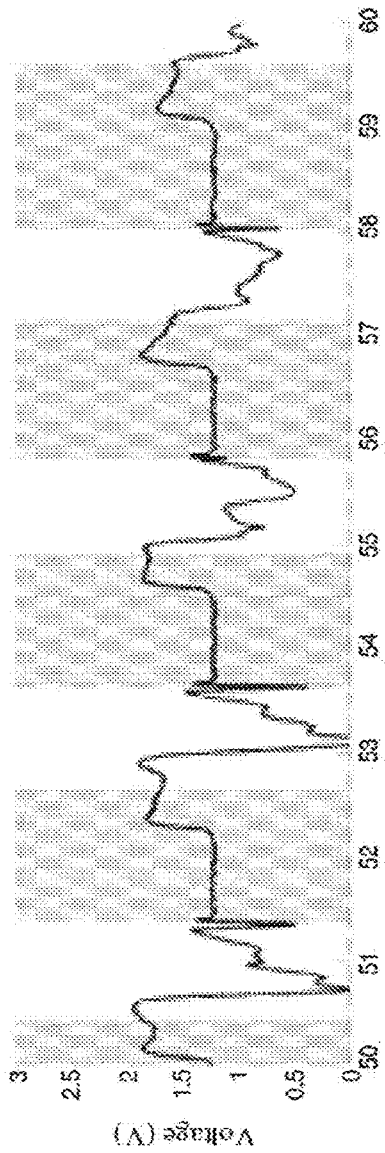
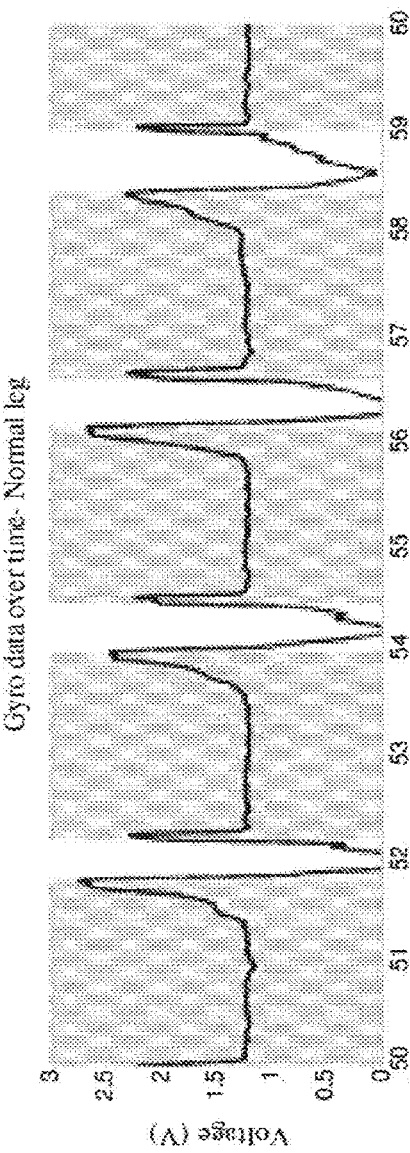
FIG. 29A
FIG. 29B

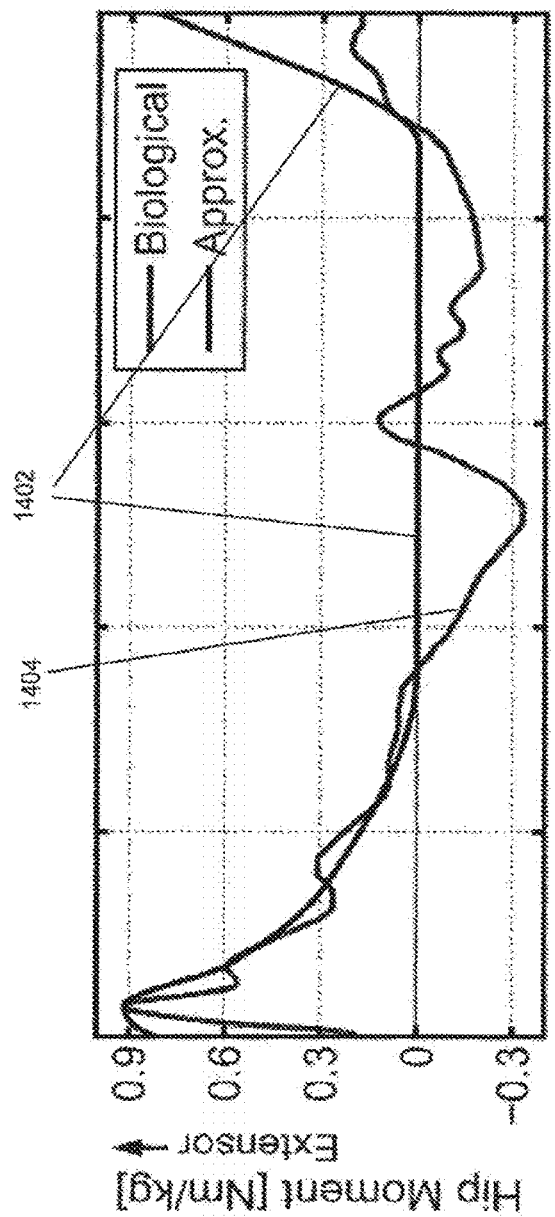
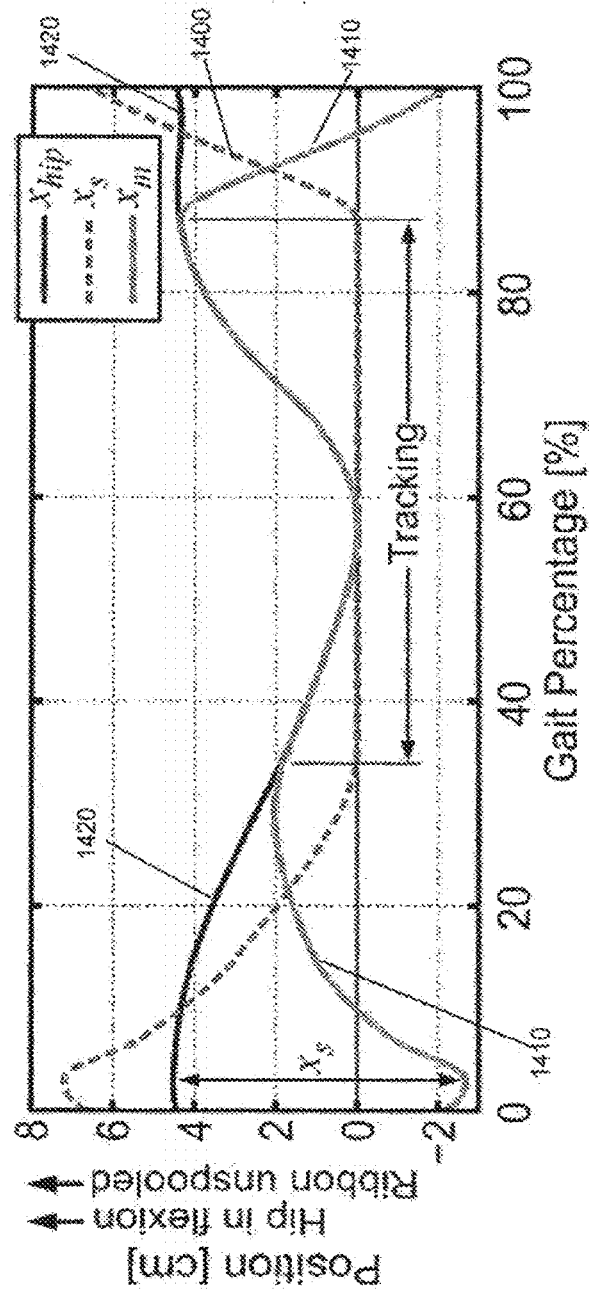
FIG. 34A
FIG. 34B

SOFT EXOSUIT FOR ASSISTANCE WITH HUMAN MOTION

RELATED APPLICATIONS

The present application is a U.S. 371 national phase patent application of International Patent Application No. PCT/US2014/040340, titled "Soft Exosuit for Assistance with Human Motion," filed May 30, 2014, which claims priority to and the benefit of U.S. Provisional Patent Application Ser. No. 61/829,686, titled "Method and System for Assisted Motion," filed on May 31, 2013; U.S. Provisional Patent Application No. 61/873,433, titled "Soft Exosuit for Assistance with Human Motion," filed on Sep. 4, 2013; U.S. Provisional Patent Application Ser. No. 61/936,162, titled "Multi-robot Cyberphysical System for Assisting Walking in Developmentally-Delayed Toddlers Application," filed Feb. 5, 2014; U.S. Provisional Patent Application No. 61/913,863, titled "Soft, Wearable Exosuits, Assistive Devices and Related Systems," filed Dec. 9, 2013; U.S. Provisional Patent Application No. 61/928,281, titled "Soft, Wearable Exosuits, Assistive Devices and Related Systems," filed Jan. 16, 2014; U.S. Provisional Patent Application Ser. No. 61/977,880, titled "Knee Exoskeleton and Downhill Walking Device," filed Apr. 10, 2014; and U.S. 61/980,961, titled "Soft Exosuit for Assisting the Lower Body," filed on Apr. 17, 2014; and is a continuation of and claims priority to PCT Patent Application No. PCT/US13/60225, titled "Soft Exosuit for Assistance with Human Motion," filed Sep. 17, 2013, each of the preceding applications being incorporated herein by reference in its entirety.

STATEMENT REGARDING FEDERALLY SPONSORED RESEARCH

This invention was made with government support under W911QX-12-C-0084 awarded by the Department of Defense/Defense Advanced Research Projects Agency. The government has certain rights in the invention.

TECHNICAL FIELD OF THE INVENTION

The present concepts are generally directed to methods and systems for assisted motion in humans and, more particularly, to methods and systems for providing assistance with motion and reducing the energy expending during motion (e.g., walking) by passively and/or actively adding assistive energy to one or more movements.

BACKGROUND OF THE INVENTION

Prior art systems for assisted motion utilize exoskeletons, comprising rigid components (e.g., linkages) and joints (e.g., pin joint), attached to the user's body with the exoskeleton joint(s) being disposed to have an axis of rotation ideally collinear with a natural axis of rotation for adjacent joint(s). Exemplary prior art exoskeletons are shown in US Published Patent Application Nos. 2007/0123997 and 2011/0040216, both to Herr et al., and both of which are incorporated by reference herein in their entirety. Such rigid exoskeletons provide the ability to replace human movements that have been lost or severely compromised and are accordingly designed to enhance the user's stability, balance and safety. Other rigid exoskeletons serve as a platform to provide physical therapy sessions in a clinical environment, such as in a physical therapy clinic, or serve to assist able-bodied users to perform tasks more easily or for longer duration.

However, these rigid exoskeletons rely on rigid frameworks of linkages, coupled to the body at select locations via pads, straps, or other interface techniques. As the user flexes or extends their limbs, these rigid links move in parallel with the limb, adding considerable inertia to movement which must be overcome by motors or by the user. Though great effort has been made to reduce the weight and profile of these devices, they still cause considerable restriction to the user's motion and, in particular, add considerable impedance to the natural dynamics and kinematics of gait. This change to the normal kinematics of walking is one reason why these exoskeleton systems do not reduce the metabolic power required for locomotion. The rigid links also cause difficulty, particularly at the extremes of motion, because the pin joints of the exoskeleton do not precisely match with the axes of the human joints, which move through intricate three dimensional paths. This causes misalignment of up to 10 cm during normal movement, causing pain and even injury to users. One solution has been to include redundant, passive degrees of freedom to allow the exoskeleton to travel and deform in key areas for wearer motion, however, this adds further weight to the systems.

SUMMARY OF THE INVENTION

The present concepts are directed to methods, systems, and devices configured to assist movements of a user, and more particularly to methods, systems, and devices relating to a soft exosuit comprising a plurality of non-extensible or semi-extensible elements flexible connection elements (e.g., webbing, straps, cords, functional textile, wires, cables, composites or combinations thereof, etc.), disposed between a plurality of anchor points or anchor areas (e.g., iliac crests, shoulders, thigh, ankle, calf, etc.), and one or more actuators adapted to selectively create tension in selected flexible members at times at which the transmitted forces to specific limbs or body parts would be beneficial to movement of the specific limbs or body parts.

The soft exosuit, as described herein, generally refers to and includes a wearable device utilizing flexible connection elements to provide assistive forces to at least one limb (e.g., a leg) or portion of a limb (e.g., a foot). In some aspects, the soft exosuit utilizes flexible connection elements to provide assistive forces to a plurality of limbs (e.g., two legs) or a plurality of portions of one or more limbs (e.g., two feet). It at least some aspects, apart from actuating one or more joints in opposite legs or opposite arms to facilitate motions wherein the limbs move in different directions at different times (e.g., walking), the present concepts also include actuating more than one limb at one time and includes, for example, coupling legs to each other, coupling leg and arm movement (same side or opposite side), coupling arm movement, or coupling other body movements to exploit potentially synergetic movements.

As compared to the prior art rigid exoskeletons, the soft exosuit is lighter, more comfortable to wear and permits a more complete, and more natural, range of joint(s) motion(s), while still being able to transfer forces or torques able to beneficially assist motion. In accord with the present concepts, the flexible connection elements can optionally be used in combination with rigid or semi-rigid connection elements and it is not necessary that all connection elements be flexible.

In at least some aspects of the present concepts, a motion control system includes at least one actuator comprising at least one actuation member, the at least one actuation member having a proximal end attached to the at least one actuator on a first side of a joint and having a distal end attached to an anchor element attachment point on a second side of the joint. In terms of the actuation member(s) having a proximal end attached to the actuator(s) on a first side of a joint and having a distal end attached to an anchor element attachment point on a second side of the joint, the proximal end attachment(s) to the actuator(s) may themselves be adjacent or proximal to the joint or may be disposed remotely from the joint (e.g., in a backpack, removed from the joint by one or more additional joints, etc.). Further, the actuation member itself may comprise a multi joint cable that spans multiple joints. The motion control system also includes a first sensor configured to output signals defining a gait cycle and a second sensor configured to output signals representing a tensile force in the at least one actuation member. The motion control system also includes at least one controller configured to receive the signals output from the first sensor and the second sensor and, responsive thereto, automatically actuate the at least one actuator, during a first portion of the gait cycle, to apply a force greater than a predetermined threshold tensile force to the anchor element attachment point via the at least one actuation member to generate a beneficial moment about the joint and to automatically actuate the at least one actuator, during at least a second portion of the gait cycle, to reduce a tensile force at the anchor element attachment point to a level at or below the predetermined threshold tensile force to avoid generating a detrimental moment about the joint.

Although the joint referred to with respect to the motion control system above pertains to a biological joint (e.g., human joint, animal joint) in accord with soft exosuit embodiments, described herein, the control system applies equally to a non-biological joint (e.g., an exoskeleton joint, a robotic joint, a joint in a prosthesis, etc.). As to application of a control system to impart beneficial moments to a joint in a prosthesis, a prosthesis is advantageously adaptable to provide a more natural and fluid motion, which can further assist balance and gait.

In at least some other aspects of the present concepts, a motion control system includes at least one actuator comprising at least one actuation member, the at least one actuation member having a proximal end attached to the at least one actuator on a first side of a joint and having a distal end attached to an anchor element attachment point disposed on a second side of the joint. The motion control system also includes a first sensor configured to measure tension in the at least one actuation member and output signals relating to the measured tension, a second sensor configured to detect a heel strike and a memory device configured to store average gait percentage data and an average step time. The motion control system also includes at least one controller configured to monitor the signals output by the first and second sensors and, following detection of a heel strike, wait for the measured tension in the at least one actuation member to rise to a threshold level, following both of which events the at least one controller calculates gait percentage within the step using the relation $$\text{Gait Percentage} = \frac{(t - t_{0\%}) \times 36}{(t_{36\%} - t_{0\%})}$$

and triggers the at least one actuator to output to the anchor element attachment point via the at least one actuation member a position assistive force profile based on the gait percentage, the application of the position assistive force profile generating a beneficial moment about the joint. In this motion control system, the at least one controller is further configured to calculate a new average gate percentage, to update the average gait percentage stored in the memory device using the heel strike and an average step time, to monitor the measured tension in the at least one actuation member at an average gait percentage of about 36% and peak force for the step, and to initiate a corrective assistive position profile to adapt subsequent actuator output.

In at least some aspects, a method of controlling motion in a robotic system, applicable to a robot or a wearable robotic system, comprises the acts of using a controller, detecting a heel strike using a first sensor of the wearable robotic system and, responsive to the detecting of the heel strike, using the controller to start monitoring a second sensor of the wearable robotic system to determine when a passively generated force in the second sensor rises to a predetermined threshold level. The method also includes using the controller to calculate gait percentage in accord with the following relation $$\text{Gait Percentage} = \frac{(t - t_{0\%}) \times 36}{(t_{36\%} - t_{0\%})}$$

and, responsive to the detecting of the heel strike, the rise of the passively generated force in the second sensor to the predetermined threshold level, and a calculated gait percentage of 36%, using the controller to trigger at least one actuator to deliver a position assistive profile to a joint based on the calculated gait percentage.

In at least some aspects, the motion control system is configured to monitor one or more parameters (e.g., a resultant stiffness of the wearable robotic, joint angles, heel strikes, etc.), and preferably a plurality of parameters, to guide the application of forces from one or more actuators to selected flexible connection elements. The applied forces can be applied intermittently as appropriate to the movement to be assisted, the level of force required, comfort and/or performance.

In at least some aspects, the stiffness of the soft exosuit, and therefore the ability of the soft exosuit to produce resulting tension changes, is a variable that is influenced by many different factors such as, but not limited to, degree of adaptation of the soft exosuit to a user's anatomy (e.g., placement of nodes relative to joints, etc.), the soft exosuit material(s), the soft exosuit element configuration stiffness (e.g., disposition of nodes and anchor points), and the user's body stiffness (e.g., a user's body stiffness is higher if the user's muscles are tensed, rather than relaxed). By way of example, a stiffness of the soft exosuit can be selectively enhanced through the use of non-extensible or semi-extensible element(s) across a joint. As a further example, in at least one aspect, such enhancement of stiffness through the use of non-extensible or semi-extensible element(s) across a joint is preferentially on only one side of the joint rather than both sides of the joint so that, when the joint is at its point of maximum flexion or extension, as a result, the soft exosuit becomes tenser as a result of the body's configuration but slack during other configurations, when the joint is not at its position of maximum flexion or extension. In yet other aspects, the soft exosuit is tensioned using a multi-articular system configured to create tension across multiple joints due to the combined motion of those joints. Soft exosuit pre-tension can be used to increase the resulting tension force in the overall system and may be achieved by, for example, tensioning (e.g., passively or actively changing the length of prior to use and/or during use) soft exosuit connection elements between nodes and/or anchor points (e.g., between the hip/ground and the thigh conical section) or by reducing the overall length of the connection elements between nodes and/or anchor points.

In accord with at least some aspects of the present concepts, the actuator(s) can provide a position or force profile which, in conjunction with the soft exosuit and body position at a time of actuation(s), provides a desired tension, stiffness and moment about a selected joint or joints. The control system is configured to use the actuator(s) to selectively tension the constituent parts of the soft exosuit, such as nodes and connection members. In one aspect, this tensioning is used to dynamically and instantly change a tension of the system across one or more joints. In one aspect, this tensioning may be applied (e.g., an auto tension function) to adjust the soft exosuit performance, comfort and fit by measuring the force and displacement of the actuator unit(s) to identify the most effective exosuit stiffness at a particular moment and/or at a particular point in gait (e.g., while walking or running) or stance (e.g., standing).

In general, the disclosed soft exosuit is configured to provide assistance to motion of a user. This motion-based assistance is not limited to walking or running, as are featured predominantly in the embodiments described herein. Rather, the motion-based assistance disclosed herein broadly relates to any movement-based assistance, which may include, for example, assistance with motion of any one or more body parts relative to another body part including, for example, movement of only one limb (e.g., one arm relative to the torso, one leg relative to the hip, or one foot relative to the corresponding leg), a plurality of limbs (e.g., two arms relative to the torso, two legs relative to the hip, one arm relative to the torso and one leg relative to the hip, etc.), the head and/or the torso. By way of example, an upper-body embodiment of the soft exosuit can be advantageously utilized by a wheel-chair bound individual to assist with locomotion.

In one implementation, the soft exosuit can be used to assist the motion of a person walking with or without a load, with such assistance providing a beneficial reduction in the metabolic consumption of energy by the user and reducing the loading on the soft tissue across the joints (e.g., ligaments, muscles and tendons), thus also reducing the risk of injury and/or exacerbation of existing injuries or preexisting conditions. This can be particularly advantageous to a soldier walking with a load. In yet other implementations, the soft exosuit disclosed herein can be used by injured, disabled and elderly people to increase mobility and/or reduce fatigue (e.g., walking, upper body mobility, rotational movements, pivoting movements, etc.).

In at least some aspects of the present concepts, the soft exosuit is passive and is configured to generate forces about one or more joints (e.g., the hip, etc.) without the use of an actuator. In such a passive soft exosuit, the soft exosuit includes an upper anchor element and a plurality of lower anchor elements and a plurality of at least substantially inextensible connection elements disposed between the upper anchor element and the plurality of lower anchor elements and disposed along paths that transmit force, wherein the connection elements are configured to provide a restorative torque to the hip to bias the thighs toward a neutral position. The suit acts in parallel with the muscles to reduce the extension torques required by the body.

In addition to motion-based assistance, the soft exosuit may be further utilized for motion assessment, rehabilitation or gait assistance activities, and movement training such as by providing resistance instead of assistance (e.g., to strengthen muscles, to provide negative feedback for improper movement, etc.) or by providing corrective assistance where needed to assist with training (e.g. golf-swing training, tennis training, etc.).

Yet further, the soft exosuit can be used by healthy people engaged in activities for which motion-based assistance is desired, inclusive of personal activities (e g, hiking, climbing, biking, walking, kayaking, canoeing, skiing, etc.) or work activities (e.g., construction work, refuse collection, freight handling, lawn care, first responders, etc.). Moreover, depending on the activity, the weight of and positioning of the actuators and/or power supply, and type of power supply, may also be varied in accord with the changing design envelope.

These and other capabilities of the soft exosuit are more fully described below.

BRIEF DESCRIPTION OF THE FIGURES

FIGS. 29A-29B show a method and control architecture for a soft exosuit in accord with at least some aspects of the present concepts wherein sensor data from a normal leg is used to as a control input for assistance provided to an impaired leg.

FIGS. 34A-34B show plots showing, in accord with at least some aspects of the present concepts, the hip moment and the position of the actuators during the walking cycle.

Figure 1:
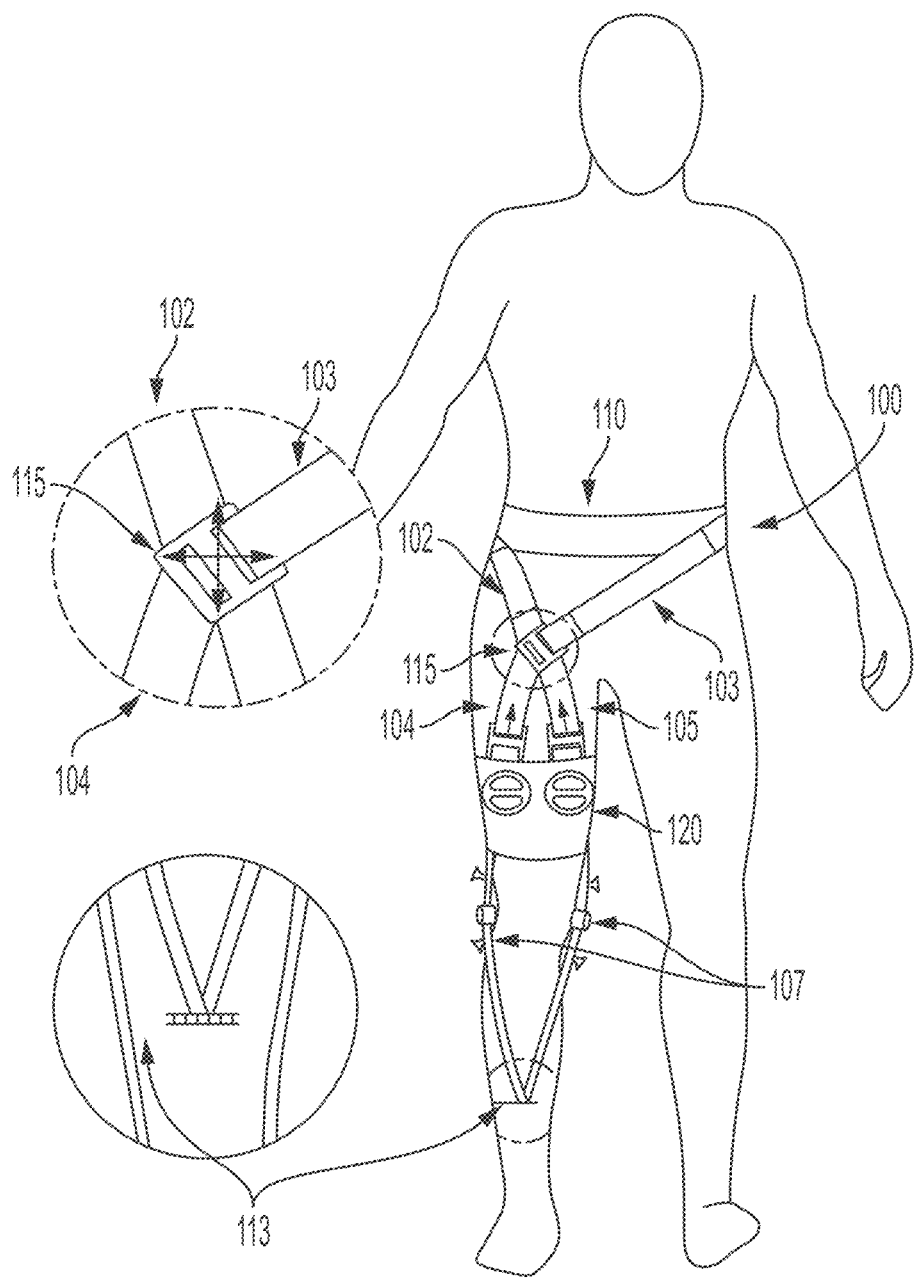
FIG. 1 is a diagram showing a front view of a second example of a soft exosuit in accord with at least some aspects of the present concepts.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the disclosure and the appended claims, without limitation.

DETAILED DESCRIPTION OF PREFERRED EMBODIMENTS

The present invention is directed to a soft exosuit system that can be used in combination with an actuator system to provide active assistance with natural motions, such as walking, running, stepping up, stepping down, etcetera.

In contrast with prior art rigid exoskeletons, the soft exosuit in accord with the present concepts utilizes flexible materials and actuators to specifically address the human factors challenges associated with exoskeleton devices and does not have a load bearing exoskeleton, but rather relies on the user's biological skeleton to assist with the application of forces and transfer of load.

The soft exosuit greatly reduces the mechanical impedance and kinematic restrictions compared to traditional exoskeletons with rigid components and does not significantly constrain or restrict the user's degrees of freedom. With such a system, it is possible to add controlled impulses of energy (e.g., during key portions of the gait cycle), rather than direct control of limb position(s), to provide assistance to locomotion and reduce the metabolic cost of movement (e.g., walking/load carrying) without significantly constraint of movement.

FIG. 1 shows an embodiment of a soft exosuit 100 in accord with at least some aspects of the present concepts. As discussed above, the soft exosuit 100 is configured to apply a moment to one or more joints (e.g., a hip joint and ankle joint as shown in FIG. 1) using one or more connection elements (e.g., 102-105, 107). These connection elements can be pre-tensioned across the joint, such that the tension imposes an assistive moment on the joint. In accord with at least some embodiments, the user can selectively increase or decrease a pre-tension in the soft exosuit. This feature of user-selective pre-tensioning modification can comprise one or more independent channels (e.g., whole suit and/or independent controls for left/right and/or front/back), controlled by a mechanical or an electro-mechanical tensioning device configured to adjust a tension along the channel (e.g., by adjusting a functional length of one or more connection elements). Pre-tensioning may also optionally be adjusted by and/or optimized by the soft exosuit controller, with or without user-inputs providing feedback to the controller as to acceptable pre-tension comfort. In yet other aspects, the user may advantageously adjust tension in one or more connection elements or anchor elements by adjusting lengths of one or more connection elements or anchor elements (e.g., by looping webbing through buckle and using a Velcro region for attachment).

FIG. 1 shows a soft exosuit 100 comprising a waist belt 110, a node 115, a thigh brace 120 and connection elements 102, 103 connecting the waist belt and the thigh brace. The waist belt 110 encircles the waist and engages the iliac crest as a support member. One or more additional support elements (e.g., shoulder straps (not shown)) could also be utilized in addition to, or alternatively to, the waist belt 110. By allowing the waist belt 110 to tightly conform to the body at a narrow portion of the waist, the natural body features help to maintain the waist belt in position. The thigh brace 120 provides a support point or node on the thigh to guide and align the connection elements 102, 103 over the hip joint and along the thigh and, owing to the tapered shape of the thigh, the thigh can be used as a support point that resists upward tension applied to the thigh brace. Tensioning between the waist belt 110 and thigh brace 120 enables creation of an initial tension higher than would be achieved with the waist belt 110 alone.

By way of example, the connection elements 102, 103 can be tensioned such that, during walking, the tension in connection elements 102, 103 applies a moment that encourages flexion of the hip joint at the time when the hip is extended. During the portion of the gait cycle just before pushoff (30-50%), the hip absorbs power. The soft exosuit could aid the absorption of energy during this time by resisting hip extension. Immediately after this, from 50-70% of the gait cycle, the hip provides positive power. The soft exosuit can aid this power generation as well by applying a complementary moment to the hip. Further, the connection elements 102, 103 can be connected (e.g., directly or indirectly via thigh brace 120) to calf connection elements 107 that extend down around the knee and meet at the back of the leg below the calf.

In at least some aspects of the present concepts, the calf connection elements 107 are connected to a heel attachment or anchor element that directly (e.g., inside footwear of the user, between a sock or liner and inner surfaces of a user's footwear) or indirectly (through footwear) engages the foot (e.g., an anchor point that resists upward tension). The connection element 107 can also be attached, or alternatively be attached, directly or indirectly (e.g., via an intermediary anchor element) to a point located on the outside of footwear (e.g., a boot). Thus, in some aspects of the present concepts, the soft exosuit terminates at the user's foot (or feet) where the inferior (lower) anchor points comprise anchor members engaging the user's foot (or feet) or the user's footwear.

In each of the above configurations of anchoring the soft exosuit at or near the foot or feet of a user, the connection elements are secured and tensioned to promote stiffness of the soft exosuit as well as to effectively apply forces at the heel to generate the moments needed for plantar flexion (or to assist plantar flexion, which may vary on a case-to-case basis).

In an embodiment wherein forces from the connection elements 107 are applied to a user's foot or footwear, the force may be applied at the calcaneus (heel) via, for example, fabric which encompasses the heel, via an insole insert secured under or to the user's foot, or via a sock-like webbing structure. The forces may be applied to the heel itself (or to a heel portion of footwear), to assist with dorsiflexion, or may be redirected from the heel to the superior surfaces of the foot (or to superior portions of footwear) via connecting elements, fabric, webbing, or the like (e.g., wires, cables, gears, gear trains, levers, etc. appropriate to the application) to apply a downward force thereon to assist with plantar flexion.

An insole insert may, for example, comprise a rigid or semi-rigid element enabling forces to be applied at the back of the rigid or semi-rigid element via a heel connection element. Tension from connection elements 102-105 can then be applied to the calf connection elements 107 to a heel connection element attached to the insole insert (or alternatively to a heel or rear portion of footwear or to heel or rear portion of a sock-like structure or webbing structure disposed over the foot). The heel connection element can extend under the heel along the bottom of the foot and couple to one or more connection element(s) that encircle the superior surfaces of the foot, such that a tension applied to the heel connection element causes plantar flexion of ankle joint (e.g., a foot pushing off motion).

In accord with some embodiments of the invention, the soft exosuit is constructed, designed and optimized for a specific biomechanical activity (e.g., walking, etc.). When the body executes a normal, unassisted motion such as walking, the musculature expends metabolic energy to move the bones of the body and transfer the weight from one foot to another and provide energy for forward propulsion and resisting gravity. The muscles apply moments to a specific set of joints causing them to extend and flex in a timed and coordinated manner to take each step.

In accord with some embodiments of the invention, the soft exosuit can be configured to apply a moment or torque at a joint to assist or inhibit the bodily movement with respect to that joint. Whether the moment is beneficial, and assists the motion, or is harmful, and opposes, the motion can be a function of timing of applied motion and the configuration of the connection elements of the exosuit. Motion usually involves reciprocating movement of the body parts around the joint and the application of an external moment, in a specific direction, at the proper time can supplement the forces exerted by the muscles to assist the motion. The same moment applied at a time when the joint is articulating in the opposite direction can oppose the forces exerted by the muscles and present resistance to the motion.

The connection members of the soft exosuit are naturally offset from the center of rotation of the joints by natural body structures (e.g., larger diameter legs displace the soft exosuit farther from center of rotation). In at least some aspects of the present concepts, this distance could be increased through the use of passive elements, such as spacers (e.g., fabric, foam elements, pads, etc.), or active elements, such as actuators, to increase a distance between the soft exosuit and the body of the wearer or to dynamically increase a distance between the soft exosuit and the body of the wearer in the case of such active elements. Further, as the joints move with respect to one other, the line of action of one or more soft exosuit connection members can change with respect to the joint, thus changing the moment were a force to be applied along that connection member. Yet further, the nodes and/or anchor elements may be caused to move during operation of the soft exosuit, responsive to applied forces, which can also change the line of action of one or more soft exosuit connection members. For example, a connection member 107 (see, e.g., FIG. 1) extending between the thigh brace 120 and a footwear connection element 130 (see, e.g., FIG. 2A) can change position relative to the knee axis of rotation "A" as the leg moves through 30-70% of the gait cycle. The relative change in position of the connection member 107 changes the moment that the soft exosuit can apply to or across the knee joint during those phases of movement. Thus, were tension to be applied to the connection member 107 between 30-70% of the gait cycle, the connection member 107 provides a small moment extending the knee at 30-40% of the gait cycle, provides almost no moment at the knee at 50% of the gait cycle, and provides a larger moment at 60-70% of the gait cycle.

In at least some aspects of the present concepts, the calf connection elements 107 are disposed to be slightly asymmetrically disposed relative to one another, with the lateral (outer) calf connection element 107 being disposed slightly behind the knee axis of rotation A and the medial calf connection element 107 being placed slightly forward of the lateral (outer) calf connection element or slightly forward of the knee axis of rotation. This configuration facilitates directing of tensile forces exactly through the knee center of rotation at all times. Dynamically, in the early stages of the gait, the medial calf connection element 107 is slightly in front of the knee center of rotation, and the later calf connection element 107 is through it or slightly behind it and, in the later stages of the gait, this reduces the effective moment arm (and moment) around the knee.

In at least some aspects of the present concepts, a soft exosuit 100 is configured to extend across multiple joints, while being anchored at the shoulders and/or hip (e.g., via a waist belt 100 or equivalent waist-positioned connection member) at one end and at the heel (e.g., via a footwear connection element 130) at another end. The footwear connection element 130 may comprise any connection element(s) attached to an outside of worn footwear, attached to a user's foot and/or disposed within worn footwear. The soft exosuit 100 structure, in this example, comprises a first connector element 104 having a length (S1) between the waist belt 110 and the thigh brace 110, which itself has a length (S2). A second connector element 107 having a length (S3) is attached to the bottom of the thigh brace 110, runs along the lateral gastrocnemius, and is connected to the footwear connection element 130. The first connector element 104 (S1) will change in accord with changes in the hip angle during movement. The length of the thigh brace 110 (S2) is generally fixed, as it extends over a segment of the body that does not traverse any joint. The length of the second connector element 107 (S3) will change based on relative changes between the knee and ankle angles. As a whole, the distance between the two anchor points (the hip and the heel) is a combination of lengths S1, S2, and S3 and the selective tensioning of the soft exosuit desirably takes into account the combined effects of multiple joints.

In accord with the invention, by understanding timing of the moments applied to that set joints, a soft exosuit can be configured to apply moments to some or all of the set of joints in timed and coordinated manner to supplement the moments created by natural muscle movements and enable the body to move at the same rate while expending less metabolic energy or restoring mobility for those with reduced muscle function. These moments can be created in a passive or an active manner. In a passive configuration, the natural motion can create tensions in the soft exosuit between the support features and the connected elements of the soft exosuit to create moments at specific joints at specific times during the motion cycle. In an active configuration, one or more actuator(s), however powered, can be employed to create tensions in the soft exosuit that generate moments at specific joints at specific times during the motion cycle. In accord with some embodiments of the invention, the soft exosuit can be configured to actively as well as passively generate forces on the body that supplement the forces generated by the musculature, to enable the body can to do less work and reduce the metabolic cost of a given motion as compared to the unassisted execution of that motion. This can be accomplished using a soft exosuit configuration that can passively create tensions using the natural body movement in combination with one or more actuators that actively applies tension to the soft exosuit in a coordinated manner.

In at least some aspects of the present concepts, the soft exosuit is configured to absorb energy from the user's motions, similar to the manner in which the user's muscles absorb energy from the user's motions. At various times in the walking cycle, for example, the muscles absorb power, such as to arrest the motion of the torso as it falls forward under the influence of gravity, or to slow down the leg in preparation for stance. To absorb power during these and other times, the muscles may contract eccentrically, extending under the applied external force while applying force. To reduce the amount of force the muscles must apply in these situations (or in a situation where power is absorbed by muscles/tendons when the muscles are isometrically contracting) and/or to reduce the probability of soft tissue damage, the soft exosuit can apply force parallel to active muscles at any time to absorbing power from the body that might otherwise prove potentially detrimental or minimally beneficial. This absorbed power could then be harvested via an energy storage device (e.g., a spring system, a resilient member, etc.), and returned to the body at some point later in time (e.g., at a subsequent point in the gait cycle). By way of example, the absorbed power could be harvested by compressing a spring, which then will then expand responsive to decreases in the applied compressive force. A compressed spring could optionally be temporarily held or locked using a latch or some other mechanism to retain the spring in the compressed state until a time which the energy is to be returned into the soft exosuit system. In another example, the absorbed power could be harvested by converting it to electrical energy and storing the energy in a battery. Potentially, energy could be stored through other means such as, but not limited to, hydraulic, pneumatic, or chemical energy storage appropriate to a given design envelope. Energy storage from power absorption could occur in both passive and active modes of the suit. In passive modes, energy storage could use passive mechanisms (e.g., a clutched spring, etc.), while in active mode the soft exosuit could either use these schemes or additionally use schemes which directly pull on an actuator to generate stored energy, for example back-driving the same electrical motor used to actuate the soft exosuit at other times.

Figure 2A:
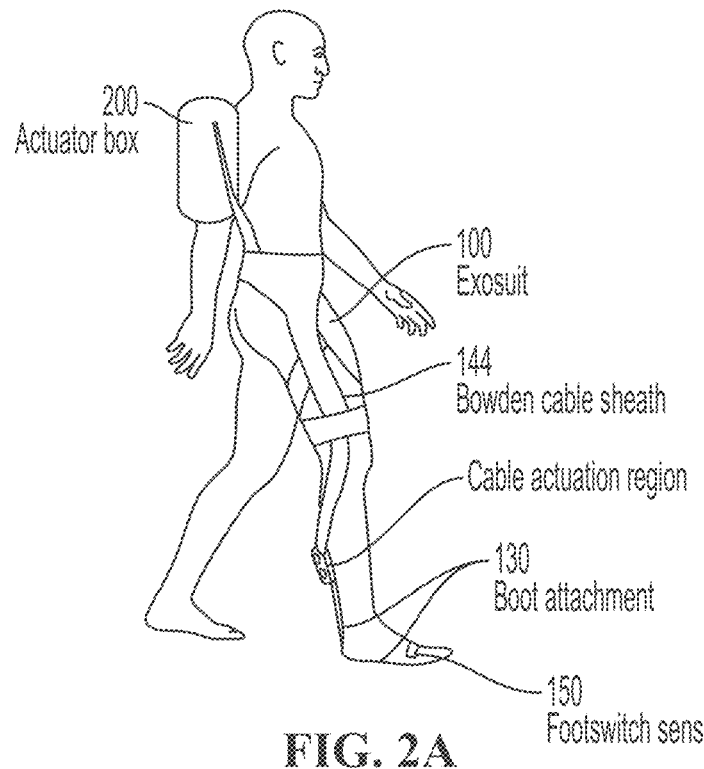
FIGS. 2A-2B are diagrams showing, respectively a representation of a side view of a soft exosuit according to at least some aspects of the present concepts, and representations of perspective views of a soft exosuit according to at least some aspects of the present concepts.

As shown in FIG. 2A, for example, the calf connection elements 107 apply a tension on a footwear connection element 130 that engages the foot. Depending on the position of the calf connection elements 107 with respect to the knee joint, tension in the calf connection elements 107 can apply a moment on the knee joint. By positioning the calf connection elements 107 forward of the axis of the knee joint, the tension in the calf connection elements 107 can encourage extension of the knee joint and by positioning the calf connection elements 107 behind the axis of the knee joint, the tension in the calf connection elements 107 can encourage flexion of the knee joint. Aligning the calf connection elements 107 through the axis of the knee joint can be used to transfer the tension without creating a moment (beneficial or harmful) on the knee joint.

In accord with a passive configuration embodiment of the invention, the calf connection elements 107 can be connected by an inelastic member (e.g., cable, strap, etc.) or elastic member to the heel connection element, such that during normal walking, the tensions created in the soft exosuit cause beneficial moments to applied on one or more of the leg joints (e.g., the hip, the knee and/or the ankle) of at the appropriate time to supplement the natural muscle movements. For example, a normal walking gait results in a backwardly extending leg at about half way (50%) through the gait cycle. As a result, a tension is created in the soft exosuit that extends from waist belt 110 down the connection elements 102-105 on the front of the thigh, along the calf connection elements 107, around the knee and down the back of the leg to the heel strap. The tension can create a beneficial moment in the hip joint causing assisting with hip extension and then subsequently assisting it to flex and propel the leg forward when the energy stored due to this tension is released potentially in addition to an active force from one or more actuators. The tension can also create a beneficial moment in the ankle joint where it assists with dorsiflexion and subsequently assists with plantar flexion of the ankle in addition to an active force applied by one or more actuators, causing the foot to push off in a forward direction.

In accord with an active configuration embodiment of the invention, a user's motion can be further assisted by adding one or more active components that actively pull on the heel connection element at the appropriate time to increase the push-off energy of the foot. In this embodiment, the heel connection element can be connected to an actuated cable or other actuation member that pulls on the heel connection element at a predetermined time to apply a beneficial moment about the heel. The actuated cable or other actuation member is connected, directly or through an intermediary power train, to a motor or other actuator controlled by a controller to apply the force to cause a specified moment at a predefined time. In one example, a cable (e.g., a Bowden cable comprising a substantially incompressible sheath) is provided to connect the calf connection elements 107 to one or more footwear connection elements 130 at the back of the leg. Such a force applied to assist with push off at the ankle can also assist with flexion at the hip.

It is to be noted that the one or more footwear connection elements 130 may be displaced laterally and/or vertically from a surface of the footwear. For example, a footwear connection element 130 may be disposed on a rigid spur, rigid beam member, or adjustable beam member, attached to or integrated with a footwear rear portion, top portion, or bottom portion. In this manner, the location of the applied forces may be altered relative to the footwear (e.g., to increase a moment arm).

In accord with some embodiments of the invention, the soft exosuit is configured to provide a plurality of anchor elements disposed at anchor points to permit engagement of the soft exosuit with natural features of the body that well serve as anchor points. However, in accord with other aspects of the present concepts, it may be desirable to establish anchor points or support point at a location where there is no such natural feature of the body, where application of a load would normally have undesirable consequences. In accord with these embodiments, one or more connection elements or struts can be used to transfer the forces from the support point disposed at a desired location to a different location on the body, such as one or more anchor points corresponding to natural features on the body (e.g., shoulders, iliac crest, etc.).

For example, in the Bowden cable embodiment noted above and shown in FIG. 2A, the Bowden cable sheath can extend from a point on a backpack of the user down along the side of the leg to a location behind the calf. Thus, the Bowden cable (or other type of cable, such as a Nokon® brand cable) can be fastened to the calf connection elements 107 at the point where they meet below the calf in the back of the leg and the proximal end of the cable sheath is coupled to the housing of the actuator (e.g., a shoulder-borne backpack comprising a drive motor and pulley system) to help maintain tension in the exosuit. Similarly, as noted elsewhere herein, other cable types or actuation elements (e.g., ribbons, fabric, etc.) can be used and routed (e.g., though fabric of or channels in the soft exosuit) from the actuator(s) to specific locations at which a force is desired to be applied.

Forces then can be created between the point where the Bowden cable sheath 144 attaches to the soft exosuit and where the central cable 142 attaches to the soft exosuit 100. As a result, a tension can be created in the soft exosuit 100 between the waist belt 110 and the support point at the end of the Bowden cable sheath 144 that joins to the ankle connector element 113 at the back of the leg. This tension can be dynamic in the sense that, as the user walks the backpack moves, as does the lower leg, changing the distance between the proximal end of the Bowden cable sheath 144 and the distal end of the Bowden cable sheath that provides the connection point 113 for the lower connection members of the soft exosuit. In addition, the hip also moves, changing the distance between the anchor point on the hip and the anchor point at the lower leg which can affect the tension in the soft exosuit during use.

Thus, the beneficial moments of the soft exosuit can be enhanced by passive and/or active components that apply forces that can create beneficial moments to supplement muscle action. By analyzing the biomechanics of the natural motion to be assisted and the power expended by each joint in the execution of motion, supplemental moments can be identified to receive a desired level of assistance.

For example, during normal walking, power is expended by the body as it transitions support from one leg to the other in course of propelling the body forward. A significant portion of this power is provided by the hip and the ankle, with the ankle having a large positive moment at about 50% or mid-way through the gait cycle. According to some embodiments of the invention, walking assistance can be provided by applying a positive moment to the ankle from approximately 35% to 60% of the gait cycle.

In accord with some embodiments of the invention, the soft exosuit 100 can be designed to take advantage of the natural motion of the various parts of the body, by identifying support points that are or become further apart at a time when a positive moment applied to one or more joints (e.g., the ankle) can be beneficial. The soft exosuit 100 can be configured with connection elements that extend around the joint to establish a tension using one or more nodes or anchor points to create a beneficial moment about the axis of the joint. In the example of FIG. 2A, for example, the soft exosuit 100 can be tensioned between the hip (via waist belt 110) and footwear connection element 130 to create a beneficial plantar flexion moment at the ankle at an appropriate time during the gait cycle. In addition, tension in the soft exosuit can be guided over the hip joint, applying a beneficial moment that encourages hip flexion and/or over the knee joint, applying a beneficial moment that encourage knee extension, each or both at point(s) in the gait cycle when the moments would be beneficial to the hip and/or knee motion.

Additional metabolic energy can be saved by providing one or more actuators that can create increased or additional tensions in the soft exosuit 100 to provide increased and/or additional beneficial moments. For example, in the soft exosuit 100 shown in FIG. 2A, an actuator cable 142 can be used to apply a positive moment on the ankle joint by pulling on the heel which is several centimeters displaced from the axis of the ankle joint. As noted above, in one embodiment of the present concepts, the cable is a Bowden cable comprising a substantially incompressible sheath. In another embodiment, the sheath itself is configured to provide dynamic properties, such as by having a resilient sheath that stores and releases energy, or by incorporating a spring element into the sheath.

As noted above, a distal end of the actuator cable 142 is attached, directly or indirectly (e.g., via a connection element) to an anchor element which, as shown in the example of FIG. 2A, extends from the heel under the foot and then wraps around the top of the foot. A drive motor and pulley system can be coupled to the proximal end of the actuator cable 142 and the drive motor controlled by an on-board controller (e.g., computer) to actuate the actuator cable during the desired time period (e.g., 35% to 60% of the gait cycle) to provide motion assistance. Sensors (e.g., foot strike sensors, joint angle sensors, etc.) are advantageously used to synchronize the actuator cable 142 cable actuation with the gait cycle of the user. As one example, tensile forces are sensed by force sensors in one or more connector elements, nodes or anchor elements and these forces are monitored and evaluated by the controller (e.g., could for several cycles of movement) to estimate the gait cycle, following which the controller progressively engages the actuator(s) over a few or more cycles of movement or after instruction by the user to enable actuation). Alternatively, the controller may infer the gait of the user by other feedback, such as manual inputs from the user or from tensile forces sensed by force sensors in the straps (e.g., the controller could monitor forces in the straps for several cycles of movement, following which actuation can progressively ramp up over a few more cycles of movement or after instruction by the user to enable actuation.

As previously noted, the soft exosuit concepts herein are deployable to reduce the metabolic cost of various activities, such as walking, by providing assistance at specific points of the activity and to reduce the loading on the soft tissue (muscles, tendons and ligaments) across the joint. Where a user expends less energy in the activity (e.g., walking), the user will be less fatigued than the user would be without assistance. Fatigue ultimately leads to a deterioration of performance (e.g., a breakdown of the gait), which can increase the risk of injury. Reduction in metabolic costs can decrease the risk of fatigue-related injury. In accord with at least some aspects of the present concepts, the soft exosuit system is able to decrease the user's metabolism below the level experienced by the user when conducting the activity (e.g., walking) without the soft exosuit. The soft exosuit can also reduce the stresses on the soft tissue by having some portion of the forces at each joint born by the soft exosuit.

The soft exosuit 100, shown in FIG. 2A, includes a plurality of connection elements comprising, by way of example, a cloth, textile, or webbing (e.g., synthetic and/or natural fibers, poly-paraphenylene terephthalamide, etc.), worn underneath or on top of the clothing. An actuator unit 200 can be worn on the back (e.g., in a shoulder-borne backpack, attached to a shoulder-borne frame, etc.), on the waist (e.g., attached to a waist belt, etc.), or in or on a device used by the user (e.g., a bike, a wheelchair, a kayak or canoe, a walker, etc.). In FIG. 2A, a Bowden cable unit extends from the actuator unit 200 and connects the soft exosuit 100 to the footwear connection element 130. In a configuration where the actuator unit 200 is borne in or borne by a device used by the user, the Bowden cable sheath 144 may be advantageously attached to a fixed anchor point (e.g., on waist belt 110) and then the sheath and the Bowden cable 142 passed down for attachment to the footwear connection element 130. As noted, the soft exosuit 100 comprises one or more connecting elements (e.g., 102-105, 107), nodes (e.g., 113) and anchor points to control the transmission of forces along, to and from the user's body. The soft exosuit system 100 also optionally includes a foot sensor 150 or actuatable switch to sense the forces applied to the foot during walking or otherwise to actuate (switch on or off) at a point of substantially maximum force corresponding to a heel strike. Sensors able to be used to assist in the determination of gait, for example, include, but are not limited to foot switches, Inertial Measurement Units (IMUs), accelerometers, Electromyogram (EMG) sensors, strain sensors to detect strain in user's skin in selected locations, sensors built into the soft exosuit to detect tensile and/or shear forces in the suit, sensors in a motor or other actuator to detect the actuator position, sensors in series with a Bowden cable or part of the Bowden cable sheath to detect the force in the cable, or other sensors.

In accord with some embodiments of the invention, the soft exosuit 100 can include one or more actuator units 200 (see, e.g., FIGS. 2A-2B) that causes the distal end of the cable 142 of the Bowden cable unit to retract into the sheath 144. The distal end of the cable 142 can be connected to the footwear connection element 130, and the distal end of the Bowden cable sheath 144 can be connected to the soft exosuit 100 at the back of the calf. When the cable 142 is retracted, the cable 142 pulls upwardly on the footwear connection element 130 and the sheath 144 pushes the soft exosuit 100 downward from the attachment point at the back of the calf. The soft exosuit 100 then transfers the forces through the connection elements (see, e.g., FIG. 1) up to the pelvis of the user via the waist belt 110. The user's bone structure then transfers the force back down to the ankle joint and to the ground through the foot.

The forces generated by the soft exosuit 100 are advantageously configured to complement the user's musculature by acting parallel to the user's musculature. This is accomplished by configuring the connecting elements (e.g., 102-105 in FIG. 1) and nodes (e.g., node 1, FIG. 1) to extend along predefined locations along the body. So configured, the user's muscles can be activated less during certain portions of the gait cycle, because the soft exosuit provides the remaining forces necessary for locomotion. This reduction in muscle activation can be used to lower the user's metabolic rate and reduce the level of fatigue experienced over time.

In accord with some embodiments of the invention, metabolic reduction is achieved by applying power to the body at the same times that the muscles generate power and by absorbing power from the body during the times that the muscles absorb power. The ankle generates a large pulse of power between about 40-60% in the gait cycle, which extends from one heel-strike to the next. This power input at the ankle, occurring when the leg is pushing the body off the ground, is the largest power burst of any joint throughout the walking cycle. In accord with some embodiments of the invention, assistive forces or moments can be applied to the joint that experiences the largest power spikes at the point during the motion cycle that the musculature generates those power spikes to achieve metabolic reduction in an effective manner. For example, based on the evaluation of joint power, in accord with the invention, the soft exosuit 100 can be configured to apply assistive forces to the ankle joint during this point in time, between about 40-60% of the gait cycle.

In accord with some embodiments of the present concepts, the soft exosuit 100 can extend from the ankle up to the pelvis and can additionally, or alternatively, create moments at the knee and hip as well as the ankle. In a multi joint system, the forces applied can affect each of the joints beneficially, and thereby provide more effective assistance. In accord with these aspects, the soft exosuit 100 is able to create moments at the knee and/or at the hip at times during the gait cycle when such moments would beneficially affect these joints. Natural movements and/or actuators that generate tension or displacement of the soft exosuit at one location/joint can, accordingly, benefit more than one location/joint.

In accord with some embodiments of the invention, the soft exosuit 100 can provide a number of functions. The soft exosuit (e.g., 100) can create precisely-controlled beneficial moments through, for example, the hip and/or ankle joints. As previously noted, a moment is considered beneficial if it assists the natural musculature. The disclosed soft exosuit's architecture and the topology of the connection elements desirably are configured to mimic, as best possible, the force vectors approximating the forces provided by the user's muscles.

In accord with at some embodiments of the present concepts, the soft exosuit is optimized to maximize stiffness (e.g., strapping it securely to anchor elements at anchor parts of the body). For a low series spring stiffness in an ankle exoskeleton, required power increases as 1/k. It is accordingly desirable to make the soft exosuit as stiff as possible to provide for higher power efficiency when applying assistive forces to the wearer. Furthermore, high exosuit stiffness will reduce the displacement of the soft exosuit relative to the user's body during movement and/or during actuation, thus reducing the risk misalignment of nodes and connection elements and reducing chafing. It is contemplated, however, that various applications could favor a minimized stiffness and/or a variable stiffness (e.g., automatically varied by a controller or manually controlled) that enables the stiffness to vary based on the user's activity (e.g., to minimize stiffness and enhance transparency when assistance is not required and to maximize stiffness and when assistance is required).

Both the fit of the soft exosuit 100 and its stiffness can be influenced by the exosuit's tension and alignment. If the soft exosuit is improperly aligned, whether by initial set up or by movement of the soft exosuit 100 during use, the moments created will not be optimal and, more significantly, the moments may prove distracting or even deleterious over time, as they cease to occur where necessary. It is desirable that the soft exosuit 100 remain in the correct location on the body even as the user moves and as the soft exosuit is actuated, lest the soft exosuit functionality or efficiency be adversely affected. To facilitate retention of the soft exosuit 100 in the proper placement during use, it is advantageous to pre-tension the soft exosuit (e.g., actuator cable(s), connection elements, etc.) following donning of the soft exosuit. The initial tension in the soft exosuit can be adjusted manually (e.g., by adjusting strap, buckles, fittings, cables, controls that adjust a tension in a plurality of components at the same time, etc.) or automatically using one or more actuators (e.g. a motor-driven mechanism).

In at least some aspects of the present concepts, the soft exosuit 100 comprises one or more adjustment members, which may be manual and/or automated, to facilitate donning and doffing of the soft exosuit 100 and to enable a user to tighten and/or loosen one or more connection elements to make the soft exosuit comfortably snug. For example, a manual or automatic adjustment member is advantageously utilized to retract and/or tension cable 142, attached to connector 113 (which in turn is attached to anchor member 130), within sheath 144, which pulls the soft exosuit 100 down and the anchor member 130 up, taking any slack out of the cable 142 and creating a small amount of tension in the system. In accord with some embodiments of the present concepts, the user can set the tension so to barely detect the exosuit's presence during movement (e.g., walking) Actuation can then be applied to the soft exosuit 100 from that point of system tension.

In accord with some embodiments of the present concepts, actuator actuation member(s), such as Bowden cables, are used to position the mass of the actuation system 200 (FIGS. 2A, 2B) away from the foot and the ankle joint being actuated. Using such actuation member(s), the actuation system 200 can be attached to a user's waist or carried in a backpack. In accord with at least some aspects, an actuation system 200 utilizing Bowden cables permits routing of the cable sheath along a path that does not adversely impact the user's motion. There are many ways that the sheath 144 of the Bowden cable can be attached to the soft exosuit. By way of example, one attachment scheme for the sheath includes a male/female connector disposed on one or more points of the soft exosuit, with corresponding male/female connector(s) disposed along appropriate sections of the cable sheath. In another configuration, the cable sheath 144 can be fixedly attached to the soft exosuit (e.g., sewing, bonding agents, adhesives, etc.), routed through a formed channel in the soft exosuit, attached to the soft exosuit using Velcro attachment members, or attached to the soft exosuit using with one or more tying members.

Where the actuation system 200 utilizes Bowden cables, for example, a small, geared motor is provided to drive a pulley or, alternatively, a larger motor directly driving a pulley can be used to pull on the cable 142 to apply an assistive force on the heel, as shown in the example of FIG. 2A. Other drive mechanisms can be used, of course, such as, but not limited to, linear motors and hydraulic/pneumatic actuators. The manner of actuation system 200 utilized depends, in part, on the motion that is to be assisted and the specific weight and performance requirements for such assisted motion. In accord with some aspects directed to assistance with walking, the actuator system 200 utilizes a battery 118, or a plurality of batteries, configured to provide an average power output of less than 100 W, which minimizes the weight of the soft exosuit 100 actuation system 200, while retaining metabolic benefits. For example, additional mass carried by the user causes a corresponding and predictable increase in the user's metabolism (e.g., at the rate of about 0.9% per added kilogram on the back), so minimizing weight of the actuation system 200, when borne by the user, is generally beneficial.

Figure 3:
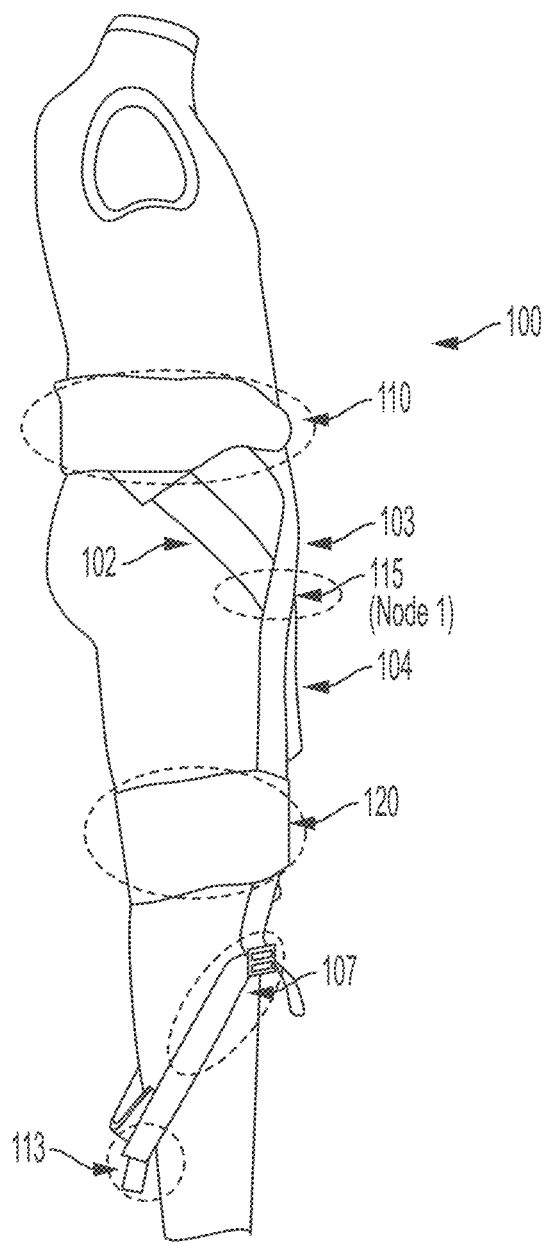
FIG. 3 shows a side view of a soft exosuit (V5), according to at least some aspects of the present concepts, depicting major components of the soft exosuit.

FIG. 3 shows an example of a soft exosuit 100 according to at least some aspects of the present concepts. The soft exosuit 100, as illustrated, includes a waist belt 110 connected by connection elements 102, 103 through a node 1 to connection elements 104, 105, which are in turn connected to thigh brace 120. The thigh brace 120 is connected to a T-connector 113 by calf straps 107. The soft exosuit 100 can be made adjustable to accommodate the natural motion of the user and to coordinate the forces generated by actuation system 200 and the cable 142 (see, e.g., FIG. 2A) with that of the forces of natural motion. As the user walks, the forces generated by the actuation system and transmitted to the cable are applied to heel of the user to reduce work the user's musculature while walking.

During walking and running, the muscles in the leg generate moments (moment forces) at the hip, knee and ankle joints during the gait cycle in order to propel the person's center of mass forward and resist gravity to maintain an upright posture. These moments change in magnitude and direction over time as they are generated by the muscles around these joints in order to guide the person from heel strike and weight acceptance through stance to push off and into swing. As noted, the soft exosuit system 100 in accord with aspects of the present concepts, desirably times forces generated by the actuation system 200 and the cable 142 to supplement the natural moments at the ankle joint, reducing the metabolic burden and improving mobility. In some aspects, the soft exosuit 100 structure extends as well around the hip joint and the knee joint to provide a beneficial moment at the hip and knee during gait cycle. When the actuation system 200 retracts the cable 142 and applies a force on the foot of the user, the sheath 144 also applies a downward force on the T-connector 113 and the soft exosuit 100, which can then apply beneficial moments to the hip or knee during the gait cycle.

In accord with some aspects, forces applied to the T-connector 113 of the soft exosuit 100 results in a tension in the soft exosuit between the T-connector 113 and the waist belt 110. Node 1 and the thigh brace 120 help to align the tension over the knee and hip to provide a beneficial moment at each joint. For a healthy adult, walking at a self-selected speed on level ground power is, for the most part, generated at the hip and ankle and dissipated at the knee. In turn, muscles consume metabolic energy to generate these moments. As noted, one of the benefits of aspects of the soft exosuit disclosed herein is to reduce the metabolic cost of walking by adding energy at the ankle to assist with plantar flexion during push-off and to assist with absorbing energy at the hip during late stance and add energy during an even later portion of stance. Adding energy at the ankle can reduce the muscle activation needed to generate the large ankle moment and power required at push-off and thereby reduce the necessary metabolic cost. To reduce the metabolic cost of walking, the soft exosuit disclosed herein advantageously permits natural gait dynamics. In some aspects of the soft exosuit, the energy applied at the ankle is provided by a cable, which pulls up on the heel and promotes and/or causes plantar extension. The force from the cable sheath 144 is distributed up through the connection elements of the soft exosuit 100 (see, e.g., FIG. 2A).

The soft exosuit 100 architecture as seen in FIG. 3 connects the waist belt 110 to a thigh brace 120 (secured to the user's lower thigh), which is connect to footwear (e.g., boot, shoe, etc.) connection elements 130. The waist belt 110 and thigh brace 120 are connected by connection elements 102, 103 that interact with node 1 on the front, middle part of the user's thigh. The thigh brace 120 and footwear connection elements 130 are connected by connection elements 107 and the cable 142, which applies the actuator force at the ankle. The connection elements 102, 103 between the waist belt and node 1 and the connection elements 104, 105 between node 1 and the thigh brace 120 can be pre-tensioned, for example, by pulling the two sides together and connecting them with Velcro at desired position or by pulling on one side which passes through a slide or buckle on the other side, in order to remove any slack in the system that would inhibit efficient operation. Pre-tension in connection elements 104, 105 can be performed, for example, after node 1 has been secured in place and the thigh brace has been positioned and tightened about the user's thigh. Accordingly, the soft exosuit 100 is pre-tensioned between the thigh (thigh brace 120) and pelvis (waist belt 110) which are both conical in shape and thus provide resistance to the applied pre-tension.

Figure 2B:
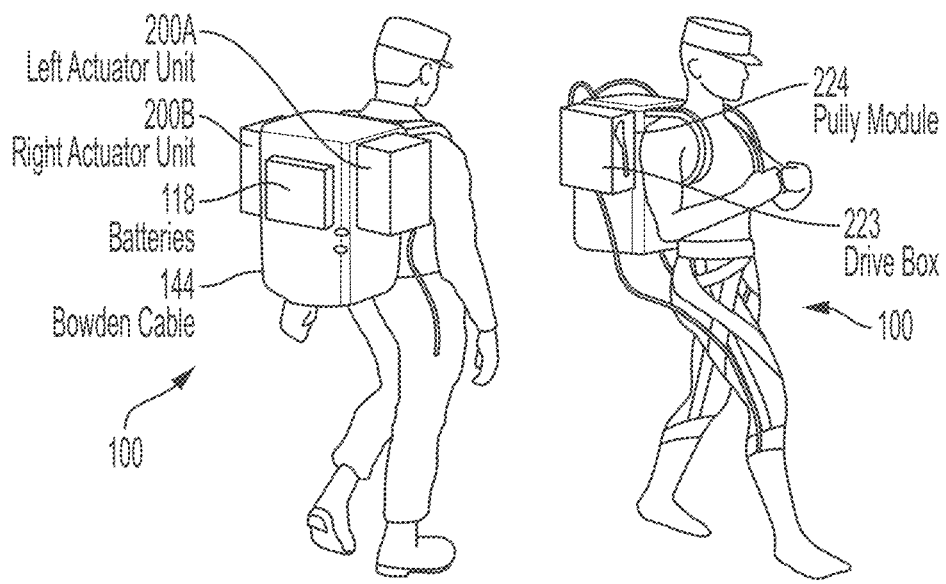

When the force is applied at the ankle, such as by the soft exosuit 100 depicted in FIGS. 2A-2B and 3, tension is also redirected across the knee and hip joints up the soft exosuit to the pelvis. As the connection elements are (further) tensioned, they create moments around the hip, knee and ankle as well as normal forces on the user at the various points of soft exosuit-to-user contact. In accord with some aspects, the soft exosuit 100 is advantageously fitted and aligned to the user to ensure that these moments and forces do not adversely affect the user's natural gait, which would cause the user to expend additional metabolic energy. The arrangement of and orientation of the connection elements, nodes and anchor points are selected to create beneficial moments around the joint or joints of interest (e.g., hip, knee and/or ankle) when tension is placed on various elements of the exosuit.

As a stiffness of the soft exosuit 100 increases, the soft exosuit is better able to transfer the actuation forces to the user in a manner that provides both the desired level of assistance and minimal dislocation of the constituent components of the soft exosuit (e.g., nodes, connection elements, etc.). As noted, the soft exosuit 100 is able to advantageously rely on one or more anchor points (e.g., pelvis, shoulders, etc.) to enhance exosuit stiffness, such as by permitting forces to be borne by the pelvis by placing the waist belt 110 on top of the iliac crest, which provides an anatomical ledge for distributing inferior and medial/lateral forces. As shown in the example of FIG. 1, the soft exosuit 100 transfers the forces generated in a leg to each side of the pelvis through connection elements 102, 103, which both originate from node 1. Providing connection elements 102, 103 to distribute forces from node 1 (e.g., of each leg) to both sides of the pelvis, the force from the actuation can be distributed over both sides of the pelvis, as opposed to the entire actuation force being anchored on the same side pelvis bone, reducing the peak point force on each respective iliac crest, enhancing comfort of the soft exosuit during use. Further, using a connecting element (e.g., 103 in FIG. 1) connecting node 1 to the opposite side hip, the soft exosuit can create horizontal forces as well as vertical forces on the opposite iliac crest due to the angle at which it attaches to the opposite side hip. This horizontal force helps to keep the waist belt 110 from slipping down as it helps bias the waist belt against the top of the iliac crest.

Figure 7:
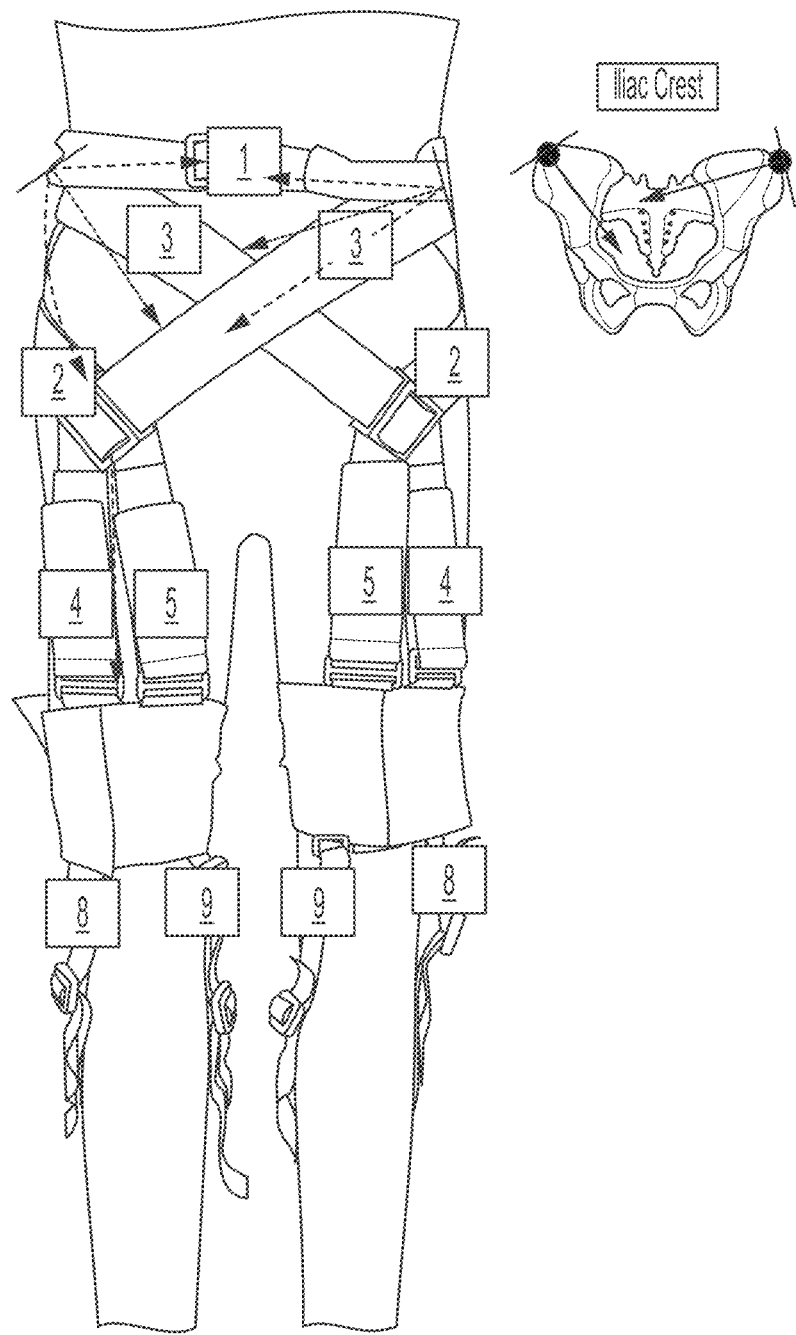
FIG. 7 shows a diagram of a soft exosuit (V5) according to the invention and the forces transmitted over the individual elements.

As shown in FIG. 7, the forces on the connection element 1 (waistband) go approximately horizontally around the body, while the forces on connection element 3 are angled downwardly. The resultant force vector from these two connection elements acting together lies between those two vectors and is approximately normal to the pelvis, which is rounded in this area as observed in the sagittal plane of the body. Pulling normally to the body enables the connection elements to remain in place while applying large loads, and avoids motion in the tangential direction which can cause discomfort.

The position of node 1 in FIG. 7 allows the forces coming up from the ankle to be routed into one point on each respective leg, which is then redirected to each side of the pelvis. In accord with some aspects of the present concepts, node 1 allows control over the moments that the soft exosuit 100 generates on the various joints by allowing adjustment of the connecting elements that connect node 1 to the waist belt 110 to adjust the direction of the forces to the waist belt.

The thigh brace 120 can be configured to maintain tension in the soft exosuit 100 by allowing the calf connecting elements 107 (see, e.g., FIG. 1) to be slightly angled in order to accommodate their position with respect to the knee's center of rotation. The calf connecting elements 107 can be connected to the footwear connection element 130 via the actuator cable 142. The footwear connection element 130 can comprise one or more elements (e.g., strap(s), etc.) which can act as a harness around the heel of the footwear (e.g., boot, shoe, etc.). The footwear connection element 130 can provide a stiff connection with the user's foot and distribute forces over the footwear. For example, when an actuator cable 142 exerts an upward force at the footwear connection element 130, the force is transferred through a system of connecting elements or materials to the bottom of the foot and the front of the foot, where an upward force is exerted at the back of the heel and a downward force is exerted on top of the forefoot. The footwear connection element 130 provides an actuator cable 142 with a stiff attachment point at the heel to effectively apply force at the ankle. The footwear connection element 130 also assists the plantar flexion moment at push off by transferring the upward actuation force to back of the heel and also to the front of the foot where it applies a downward force on top of the foot, thus applying forces which assist plantar flexion on both sides of the ankle.

Figure 4:
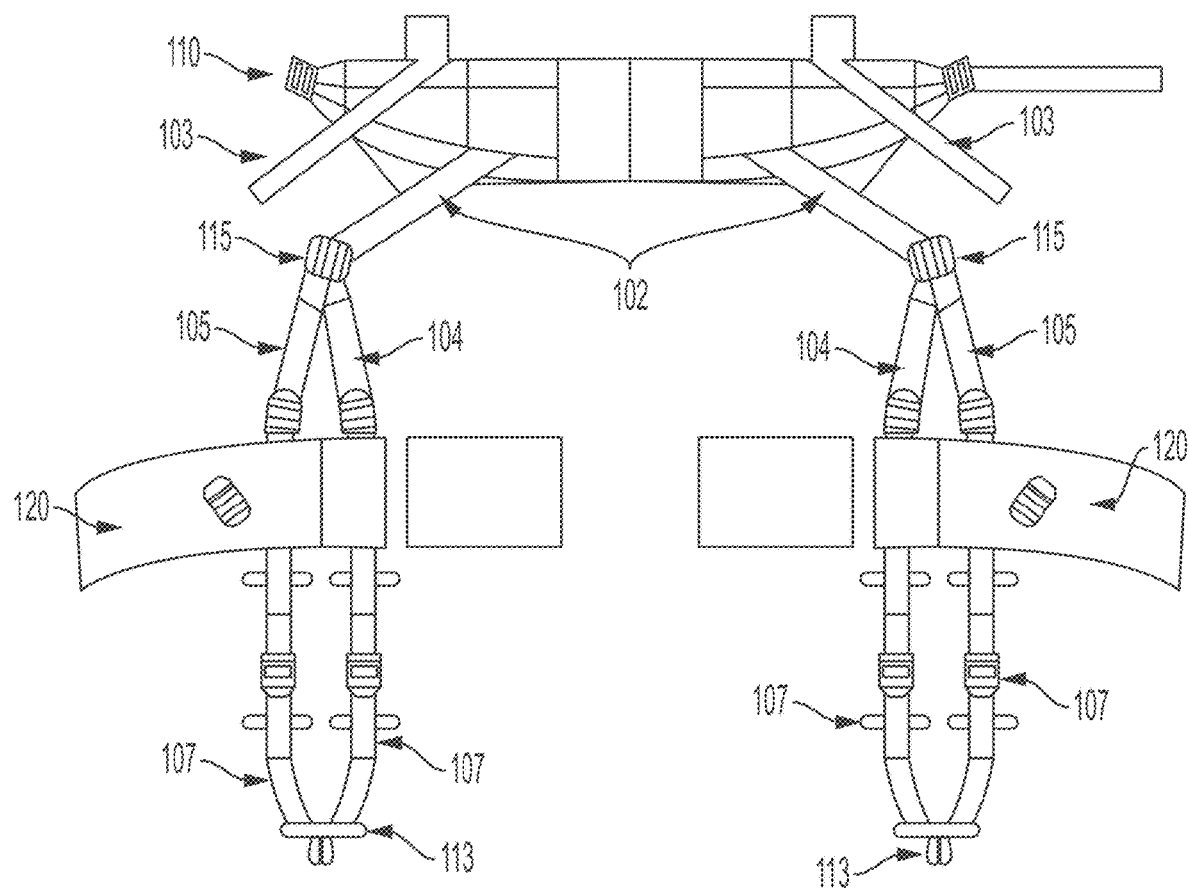
FIG. 4 shows an example of a flat pattern layout for a soft exosuit (V5) according to at least some aspects of the present concepts.

In at least some aspects, the soft exosuit 100 is constructed from flat materials (e.g., webbing, fabric, etc.) that are cut or otherwise formed to a predefined size and stitched together. FIG. 4 shows one example of a flat pattern layout for a soft exosuit according to at least some aspects of the present concepts. The waist belt 110 can be formed in sections, which can be overlapped and secured, as with conventional belt securement devices, to adjust the waist belt to people with various waist diameters. By way of example, the sections or panels shown in FIG. 4 can be constructed from one or more layers of rip-stop nylon and a fusible interfacing layer or from one or more layers of rip-stop nylon and a layer of foam padding (e.g., ⅟₁₆" to ½" thick polyurethane or ethylene-vinyl acetate (EVA)). The connection elements can be constructed from, for example, ½"-3" polyester webbing. In one aspect, the connection elements 102, 103 are formed from 2" wide polyester webbing, while the balance of the remaining connection elements are formed from 1" wide polyester webbing. Some connection elements (e.g., distal ends of calf connection elements 107) can be stitched to form loops to facilitate connection to other connection elements or structures. Buckles (e.g., plastic buckles) can be used to fasten and tighten the connection elements. The thigh braces 120 can comprise one piece or two pieces and is constructed, in at least some aspects, from a stretch twill material (e.g., a cotton-polyester blend) with hook and loop faster (e.g. Velcro( ) stitched to one side.

Figure 5:
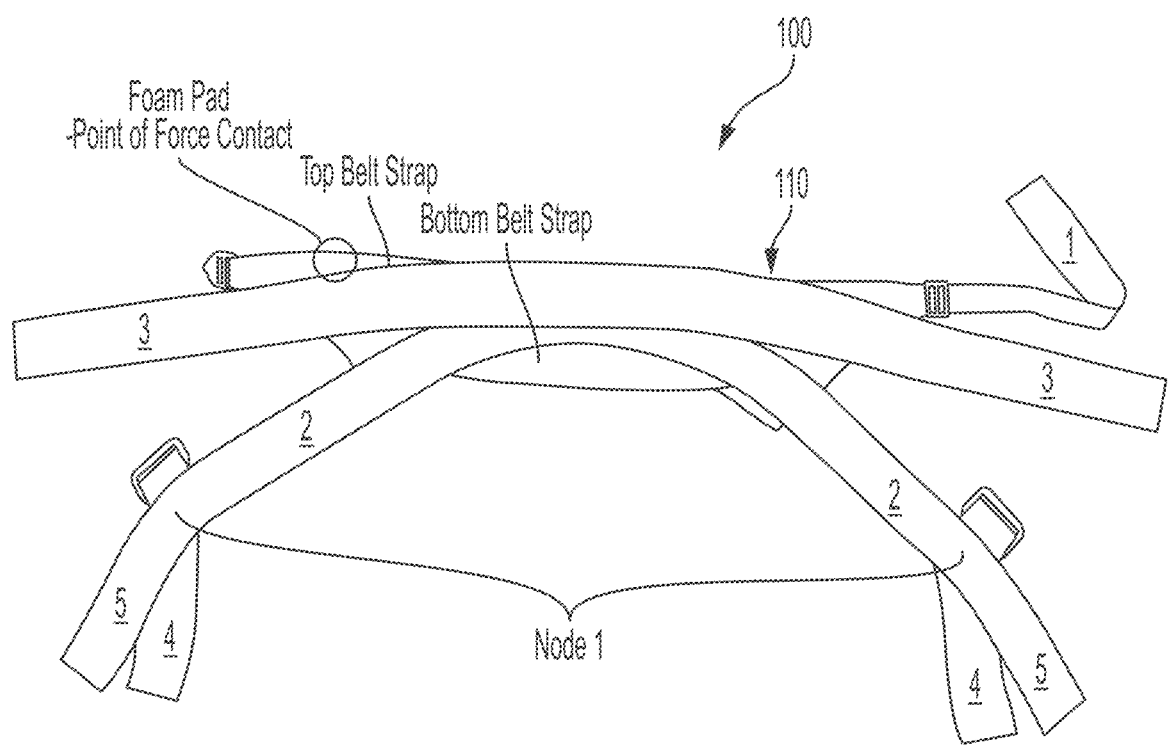
FIG. 5 shows a waist belt of a soft exosuit (V5) according to at least some aspects of the present concepts.

FIG. 5 provides an illustrative example of how the connection elements of a soft exosuit according to at least some embodiments of the present concepts can be arranged and configured. In FIG. 5, the different connection elements of the soft exosuit comprises Strap 1 (Waist Belt Connection Element), Strap 2 (Node 1 To Same Hip Connection Element), Strap 3 (Node 1 To Opposite Hip Connection Element), Strap 4 (Thigh Connection Element—Lateral), Strap 5 (Thigh Connection Element—Medial), Strap 6 (Thigh Connection Element To Calf Connection Element—Lateral), Strap 7 (Thigh Connection Element To Calf Connection Element—Medial), Strap 8 (Calf Connection Element—Lateral), Strap 9 (Calf Connection Element—Medial).

Figure 6A:
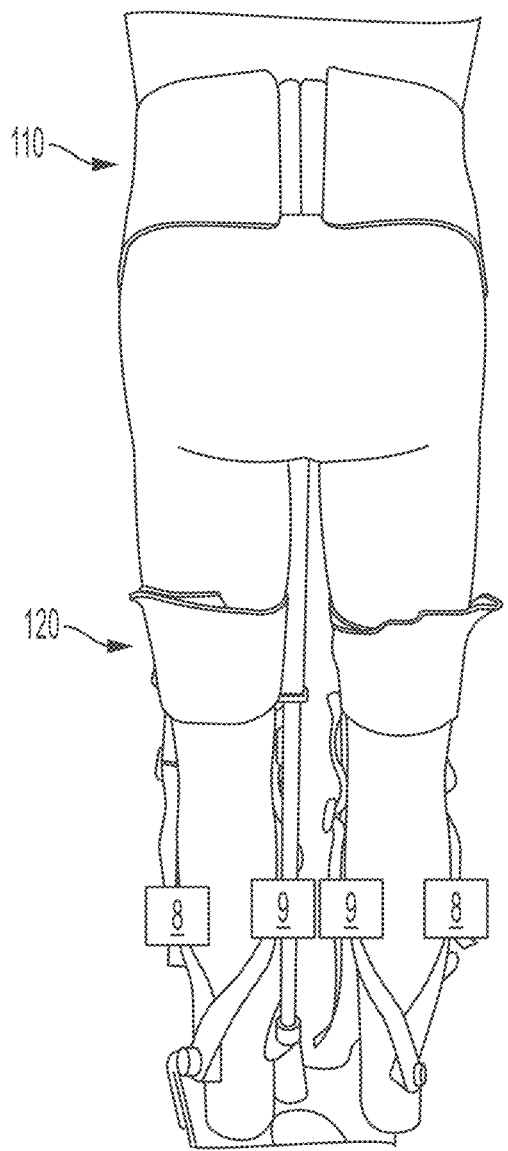
FIGS. 6A-6B show front and back views of a soft exosuit (V5) according to at least some aspects of the present concepts, an upper portion of which is shown in FIG. 5.
Figure 6B:
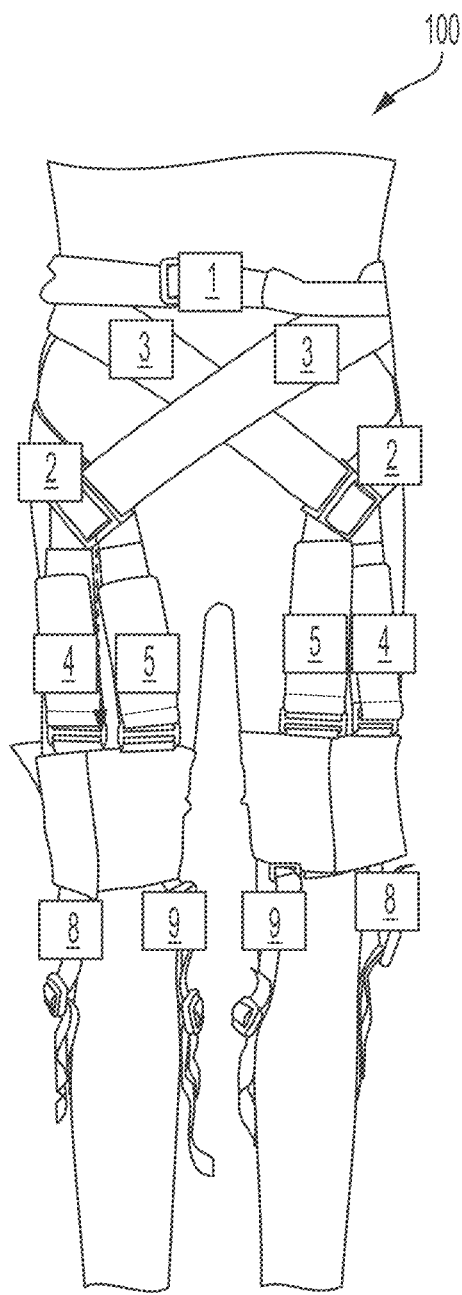

In FIG. 5, the waist belt is displayed flattened out presenting the side facing away from the user. This view provides an overview of the waist belt and the connection elements attached directly to it. In accord with some embodiments of the invention, the waist belt includes a top belt connection element and a bottom belt connection element that can be joined at the ends to a connection element and buckle that enable the waist belt to be fastened around the waist of the user with foam or other padding arranged between the waist belt and any points of contact (e.g., iliac crest) on the body. Connection elements 2 and 3 of FIG. 5 depend from waist belt 110 and connect to a top of node 1, as shown in FIG. 5 and FIG. 6B. Connection elements 4 and 5 of FIG. 5 depend from a bottom portion of node 1 and connect to an upper portion of thigh brace 200. In FIGS. 6A-6B, the soft exosuit shown in part in FIG. 5 is shown on a mannequin for illustration.

The waist belt 110 keeps the soft exosuit from being pulled down under vertical force or slipping over the iliac crest due to horizontal force that is the result of the angle of the connection elements that attach the thigh braces to the pelvis portion of the exosuit. The belt is also prevented from slipping down due to the tension placed around the pelvis by tightening the waist belt connection element. It accomplishes this by creating tension around the pelvis where a portion of the belt passes on top of the iliac crest of the hip bones. The pelvis serves as a support or anchor point for the forces which are transmitted from the T-connector 113 at ankle up through the connection elements of the soft exosuit 100 to the waist belt 112.

In accord with some embodiments, the pelvis has a relatively small range of motion throughout the gait cycle compared to other bony landmarks, such as the knee and shoulder. The pelvis has its largest movement in the transverse plane where it rotates a total of approximately 12° throughout the gait cycle. In comparison, the knee moves approximately 50° in the sagittal plane and movement of the shoulders is highly dependent on the user's posture at any given time. Accordingly, in accord with the present concepts, use of the pelvis is favorable for embodiments of the soft exosuit 110 in accord with the present concepts that are directed primarily to gait assistance. The pelvis's range of motion and the cyclic nature of the positions of the various leg segments throughout the gait cycle make the distances between the pelvis and various leg segments highly predictable throughout the gait cycle, which help inform selection of appropriate anchor points capable of maintaining soft exosuit 100 tension at specific times during the gait cycle. Further, the pelvis structure defines a ledge to which the waist belt 110 can be effectively attached to anchor both vertical and horizontal forces.

The stiffness of the soft exosuit 100 is, in part, determined by the compliance of the user-soft exosuit interface. The lower the compliance of the interface between the user and the soft exosuit 100, the higher the stiffness of soft exosuit in operation. By anchoring to a stable and low compliance feature, the soft exosuit can transmit higher forces to the body of the user. In addition, the symmetry of the pelvis allows for the loads to be distributed evenly onto the body of the user. By distributing the actuation forces to each side of the body, the normal forces acting on the body from the soft exosuit at any one point can be reduced, helping to minimize the formation of pressure sores, friction and rubbing and thereby increasing the perceived comfort of the exosuit. As noted previously, in at least some aspects of the present concepts, the actuation forces may also be, or may alternatively be, distributed to one or more other locations on the body (e.g. torso, shoulders, etc.).

In at least one aspect, the waist belt 110 comprises a top belt connection element and a bottom belt connection element, with the top belt connection element being disposed over the top of the hip bone (optionally with foam padding provided on the top belt connection element at locations where it rests on top of the iliac crest), and the bottom belt connection element disposed to lie just below the iliac crest. These two connection elements provide, in combination, a stable attachment platform.

The pelvis, at the iliac crest, provides a suitable anchor point for minimizing the compliance of the soft exosuit. As noted, the soft exosuit advantageously leverages the geometry of the pelvis, which provides a ledge at the iliac crest on which the waist belt may rest. This makes it possible to anchor both vertical and horizontal forces. Horizontal forces can also be resisted by connection elements (e.g., bottom belt strap) which surround the side of the pelvis. Reducing compliance allows for a stiffer soft exosuit, which can be useful to effectively apply forces to it and thus the wearer. As the soft exosuit reaches a certain level of stiffness, it can be useful to protect the user from the forces being transferred to them via the soft exosuit. Padding, such as layered fabric or foam padding, can be used to spread these forces across a greater surface area on the user as well as providing a damping medium which reduces the impact of these forces. However, this padding can increase the compliance in the system and thus presents another variable to control to optimize compliance and stiffness to achieve a balance in efficiency and comfort.

In at least some aspects, node 1 (see, e.g., FIG. 1, FIGS. 5, 6B) can be configured as the junction at which the forces resulting from the ankle actuation on each respective leg converge and then divide up to be distributed to each side of the user's pelvis. Adjusting the position of node 1 on the user's thigh can be useful to maintain force balance and soft exosuit 100 tension. The force may be distributed via one or more straps that attach the thigh braces 120 to the waist belt 110 of the soft exosuit.

As shown by way of example in FIG. 1 and FIGS. 6B, 7, a node (e.g., Node 1 in FIG. 6B) is placed at the middle of the thigh in the frontal plane, in accord with at least some aspects of the present concepts, and can be adjusted by connection element 2 and connection element 3, as shown in FIG. 6A. The vertical placement of node 1 on the thigh can be adjusted according to the size of the user and the distance from the node to the top of the thigh, which varies from user to user, but is generally far enough down so that it does not interfere with hip flexion. Proper vertical placement can be verified by having the user wearing the soft exosuit flex their hip after the node position has been set to see whether it interferes with hip flexion. The placement of the node can be used to optimally align and adjust the force paths in the soft exosuit 100 which, in accord with some aspects of the present concepts, can prevent or reduce problems associated with the thigh brace 120 rotating due to force imbalances. Improperly aligned force paths can create unwanted moments at the hip and knee which can result in unnatural motion, muscle fatigue and soreness. Through the use of node 1 (see, e.g., FIGS. 5, 6B, 7), the forces resulting from the ankle actuation are transmitted in a controlled and linear path from the ankle to the front of the thigh, where it can be further distributed to either side of the pelvis. With the connection elements passing into one junction (node) in this way it allows for the tension paths around the hip and knee to be adjusted more coherently by tightening, loosening or repositioning the connection elements on the exosuit. This enables greater control and fine tuning of the moments that the soft exosuit generates at the hip and knee throughout the gait cycle.

In accord with some embodiments of the invention, the particular configuration of soft exosuit utilizing node 1 helps to achieve a much higher exosuit stiffness than would otherwise be achievable since it anchors the force path to each side of the pelvis, where it is possible to achieve a much higher exosuit stiffness. The use of node 1 enables the soft exosuit 100 to distribute the forces over the pelvis, where the stiffness of the waist belt was far greater, resulting in the soft exosuit being able to maintain higher forces while suffering very little displacement. The connection elements connecting node 1 to the waist belt 110 can be secured to the node's position as they are constrained in the medial, lateral and vertical directions. Connection elements 4 and 5 (see, e.g., FIG. 7) can be tensioned to establish a pretension in the soft exosuit between the waist belt 110 and thigh brace 120 that increases the soft exosuit stiffness through pre-loading it downwardly against the pelvis and upwardly against the thigh. Correct pre-load resulting from tensioning connection elements 4 and 5 can be accomplished by creating, qualitatively, a snug tension across the front of the thigh that can be adjusted according to the user's comfort, which can vary from user to user.

In accord with at least some aspects of the present concepts, the waist belt 110 (see, e.g., FIG. 1) functions optimally when tension is maintained in the waist belt. If the waist belt 110 is not properly tensioned, the soft exosuit 100 will sag when actuation is applied.

Proper vertical placement of the waist belt 110 is desirable to maintain proper soft exosuit stiffness. In accord with some embodiments of the present concepts, the soft exosuit 100 utilizes the iliac crest on the pelvis as an anchor for the majority of the forces acting on the user. If the waist belt 110 is not supported by the iliac crest then the soft exosuit 100 may not be able to provide as much initial stiffness, unless it is supported by other features of the body. If the waist belt 110 position is set too low, or becomes too low during use, it could interfere with the hip motion of the user, causing discomfort (e.g., soreness of the hip flexors) and decreasing soft exosuit functionality.

During evaluation of aspects of the soft exosuit, it was found by the inventors that tension created across the hip during early to mid-stance could lead to muscle fatigue in the hip flexor and gluteus medius muscles. In early to mid-stance, the hip is flexed and, thus, to create a moment that will resist this flexion, tension is required to pass from behind the hip's center of rotation, below it, and to the front of the thigh. Thus, if connection element 2 in FIG. 5 or FIG. 6B passes below the hip's center of rotation, it could create such moments. There are two possible ways that could lead to connection element 2 creating these moments. The first is that node 1 is positioned too low on the thigh. The second is that connection element 2 attaches further behind the waist belt. Connection element 2 can be attached directly to the waist belt (e.g., via Velcro®) once node 1 (see FIG. 5 or FIG. 6B) is positioned correctly with respect to the center of the thigh. Once node 1 is correctly placed, it can be secured by attaching connection element 2 to the waist belt 110 by extending connection element 2 in a straight line from node 1 to the waist belt (i.e. making sure that the connection element remains smooth and flush with the wearer), ensuring that connection element 2 has a proper angle of attachment to the waist belt. Generally, node 1 can be laterally positioned in the center of the thigh, about 10 cm inward of the pelvis (e.g. iliac crest), directly above the patella and vertically positioned just below the crease between the thigh and torso. Connection elements 2 and 3 can each extend angled upwardly from this point to the side of the pelvis (side of the iliac crest), on the same side and opposite side of the body, respectively. Outer connection element 2 can be angled between about 40-65° with respect to the horizontal and connection element 3 can have a correspondingly smaller angle with the horizontal.

If node 1 is placed in an incorrect horizontal location, it will result in a disadvantageous rotation of the exosuit. For example, if node 1 (see, e.g., FIG. 1, FIGS. 3, 6B) is placed either to the left or to the right of the middle of the thigh, tension in the soft exosuit will then be unbalanced with respect to the symmetry of the leg, causing (over repeated cycles) a rotation of the thigh brace 120 in a direction of the imbalance such that the calf connection elements 107 no longer align correctly with the knee's center of rotation, creating incorrect moments on the user.

In at least some aspects of the present concepts, node 1 is placed directly in the center of the thigh several centimeters below the flexion point of the thigh. The approximate vertical position can be determined by having the wearer flex their hip once the node has been positioned to see if the node 1 interferes in any way with their hip flexion. Nominally, node 1 is placed close to the flexion point, but not so close that it interferes with hip flexion. Node 1 should be horizontally positioned in the center of the thigh, as horizontal misalignment could cause the soft exosuit to rotate undesirably. Once node 1 is positioned correctly with respect to the thigh, it is first secured by attaching connection member 2 to the waist belt by extending it in a straight line from node 1 to the waist belt, this ensures that connection member 2 has a proper angle of attachment to the waist belt, second connection member 3 is looped through node 1 buckle and attached, using care to ensure that, when securing connection member 3, the node center position does not shift. Vertical placement of node 1 is not as critical to the soft exosuit's function as the horizontal placement. If node 1 is positioned too high up on the thigh it will interfere with the user's hip flexion and will be apparent.

In accord with some embodiments of the present concepts, the thigh brace 120 can wrap around the lower thigh. In one aspect, the thigh brace 120 comprises two pieces that are joined together, the front piece which can have a hook and loop fastener (e.g., Velcro®) facing towards the user and a back piece which can have a hook and loop fastener (e.g., Velcro®) facing away from the user. The calf connection elements 107 can be sandwiched between the two layers and secured in place by the hook and loop fastener (e.g., Velcro®).

In accord with at least some embodiments of the present concepts, the bottom of the thigh brace 120 is placed between approximately 3-6 centimeters (and preferably between about 4-5 cm) above the top of the patella, but this distance can vary depending on user's physiology. Preferably, the thigh brace 120 is positioned higher to allow for a greater range of adjustability for the calf connecting elements 107. For a skinny to medium sized user with low to moderate muscle mass, the thigh brace 120 can be positioned 4 centimeters above the patella. For users with larger thigh diameters, the thigh brace 120 can be positioned 5 or 6 centimeters above the patella to permit correct positioning of the calf connecting elements 107. Thus, the position of the thigh brace 120 above the knee can be selected to provide for proper placement of the calf connecting elements 107, which are attached to the thigh brace 120, and to ensure that the calf connection elements 107 do not interfere with the knee's range of motion. Furthermore, with the thigh typically having a larger diameter further up the leg, this allows the calf connecting elements to avoid contacting the knee area, thereby avoiding chafing in the knee area.

In accord with at least some aspects of the soft exosuit 100, the location and angle at which the calf connecting elements 107 exit the thigh brace 120 can be adjusted. This adjustability permits a user to adjust the soft exosuit to accommodate their particular physiology and musculature while positioning the calf connection element 107 appropriately relative to the knee's center of rotation. Adjustments to the placement of the calf connection elements 107 with respect to the knee's center of rotation are used to ensure the correct moments are produced at the knee.

In accord with some embodiments of the invention, the thigh brace 120 can contribute to exosuit stiffness by balancing the horizontal load when the soft exosuit is tensioned. This horizontal load can be a result of the loading path of the soft exosuit being angled slightly as it travels up from the ankle to the pelvis. A change in direction occurs at the thigh brace 120 to accommodate the correct placement of the calf connection elements 107 with respect to the knee's center of rotation. The correct placement of the calf connection elements 107 is desirable because a tension is created across the knee joint when the soft exosuit is actuated. Depending on where the calf connection elements 107 are positioned with respect to the knee's center of rotation, the moment generated responsive to this tension can either help or hinder the user. In order for the soft exosuit tension to not adversely affect the user's natural knee moments, the tension can be in line with or slightly in front of the knee's center of rotation at the time of actuation. The position of the calf connection elements 107 on the thigh brace 120 and the angle at which it exits the thigh brace 120 can be adjusted so that the tension is in-line with or in front of the knee's center of rotation.

When a tension in the lateral calf connection element 107 is applied at the T-connector 113 (see FIGS. 3-4), the same is occurring to the medial calf connection element 107 on the other side of the leg and these forces on the medial and lateral calf connection elements 107 converge at the thigh brace 120. The calf connection elements 107 are each coupled to the thigh brace 120 via a secure attachment (e.g., buckle, Velcro®, clasp, etc.). The direction of the force acting on the calf connection elements 107 acts to pull them apart from one other and puts tension on the fabric between the two calf connection element 107 attachment points to the thigh brace 120. The resulting tension profile was found to provide the highest tension (largest vector) in the thigh brace 120 at the bottom of the thigh brace 120, with decreasing tension (smaller vectors) with increase in height from the bottom of the thigh brace. It is possible that, for some users, the horizontal force will reverse sign at the top of the thigh brace 120 as the force profile depends on both the direction of the force being applied and how the calf connection elements 107 are angled with respect to the thigh brace 120.

The calf connection elements 107 can attach to the thigh brace 120 and join together in the back of the shank below the bulk of the calf muscle. The junction where the two straps meet below the bulk of the calf muscle is a point at which the Bowden cable sheath 144 can be attached to the soft exosuit 100. As noted, in at least some aspects of the present concepts, the calf connection element 107 length, angle, and location of connection to the thigh brace 120 can all be adjusted to accommodate users of different physiologies. In some embodiments, there are four adjustment factors that provide for correct placement of the calf connection element 107, and an overarching objective for each of these variables is to position the calf connection elements 107 correctly with respect to the user's knee center of rotation. The four adjustment factors are (1) the location at which the calf connection elements 107 exit the thigh brace 120, (2) the angle at which the calf connection elements 107 exit the thigh brace 120, (3) the vertical position of the thigh brace above the patella, and (4) the vertical location of the Bowden Cable T-attachment with respect to the shank.

The factors noted above can be adjusted with respect to the thigh circumference and the thigh length of the user. Where embodiments of soft exosuits in accord with at least some aspects of the present concepts enable such variability in one or more of these factors (e.g., in a suit designed or fitted for a specific user, the soft exosuit may not need to provide for such subsequent adjustability), the optimal placement of the calf connection elements 107 is such that, when the calf connection elements 107 are tensioned, they do not cause moments at the knee that will negatively impact the user's natural gait cycle. One way to ensure the calf connection elements 107 do not cause moments at the knee that will negatively impact the user's natural gait cycle is to having the tension pass through the knee's center of rotation, thus ensuring that the soft exosuit creates no moments on the knee. However, since the knee flexes and extends through a wide range of motion throughout the gait cycle, with a constantly changing instantaneous center of rotation, this approach is difficult to realize. Another, more practical, way to achieve this end is to permit creation of moments that do not negatively impact the user's natural gait.

To further illustrate correct calf connection element 107 placement, an understanding of knee and ankle dynamics is helpful. In at least some aspects of the present concepts, a soft exosuit configured to assist walking movement is actuated during the terminal stance phase and pre-swing phases that occur from approximately 30% of the gait cycle to 62% of the gait cycle. At the beginning of terminal stance (30% gait cycle) the gastrocnemius (calf muscle) and soleus (inner calf muscle) gradually increase their contraction to counter the growing plantar forefoot flexor moment, as well as to store elastic energy in the muscle and tendon tissue to rebound during heel lift/push-off, that occurs as the body is falling forward. This action increases as the ankle begins to plantar flex as the heel comes up and the pivot point moves to the forefoot. Additionally as this is happening, the knee flexion reaches its lowest point (about 5° at 40%). This reduction in flexion occurs as the body's mass is now falling forward on the forefoot that places the force vector of the falling body in front of the knees center of rotation causing passive extension of the knee. However this extension is resisted by posterior muscle action, i.e. the gastrocnemius that is already tensing due to the action at the knee and ankle as well as the popliteus that lies across the knee joint. As the minimum flexion angle is reached (40% gait cycle) the knee immediately begins to flex as at that point the knee joint will have moved in front of the body vector due to the heel rising. At this point, the posterior muscles that were acting to resist knee extension are now promoting knee flexion as well as the body vector that is now posterior to the knee's center of rotation and thus passively promoting knee flexion. Terminal stance ends with initial contact of the contralateral limb (50% gait cycle). With the onset of pre-swing (50% gait cycle) the weight is shifting over to the other leg allowing the knee to flex freely that results from the elastic recoil of the Achilles tendon, the action of the posterior muscles and the passive action of the body vector being posterior to the knees center of rotation. However, if knee flexion occurs too rapidly then the rectus femoris comes on to decelerate the knee causing an extension moment at the knee, thus the extension moment during pre-swing is not always present and is dependent on how rapidly the leg goes into flexion.

From the above description, three points are to be made about the tension of the soft exosuit across the knee joint during the actuation phase. First, if such tension is present in front of the knee's center of rotation between 30 and 40% of the gait cycle, this will cause the posterior muscles (gastrocnemius and popliteus) to work even harder to reduce the decrease in flexion. This creates a feeling of "too much tension" from those wearing the exosuit, which can be remedied by moving the calf connection elements 107 to a more posterior position on the thigh brace 120. Second, if the tension is in front of the knee from 40 to 50% of the gait cycle, this will resist knee flexion that, at that point, is occurring passively due to the body vector being behind the center of rotation as well as actively due to the posterior muscles. At this point, it would be beneficial to dispose the calf connection elements 107 either in-line with or behind the knee's center of rotation as disposing them in front of the knee's center of rotation would likely overwork the posterior muscles. Third, if the tension is in front of the knee from 50 to 62% of the gait cycle, it will be resisting the knee's flexion motion that is occurring passively due to the recoil of the Achilles tendon, as well as the direct muscle action of the posterior muscles. Although the knee's flexion moment is sometimes resisted by the rectus femoris during pre-swing, this is not always the case and the extension moment that may be expected for this portion of the gait cycle may not necessarily occur.

The calf connection elements 107 are advantageously tensionable so as to create moments that do not impede the user's natural walking cycle, or other movement cycle, for a wide range of user physiology. A first challenge to determining appropriate soft exosuit connection element positioning (e.g., to achieve an optimal balance of weight, power, metabolic effect, comfort, variability of different physiology, etc.) was simply large person-to-person dimensional variances. A second challenge was the rate at which the knee goes from being extended to flexing right around push off (50% gait cycle), which is close to the end of the actuation phase. If the strap migrates behind the knee's center of rotation too early, an unwanted flexion moment would be created that would impede the user's natural gait. Thus, in at least some aspects of the present concepts, the calf connection elements 107 are positioned to be either in-line with or behind the knee's center of rotation to avoid adverse moments.

In accord with some embodiments, the calf connection elements 107 are positioned so that their respective lines of action pass through the effective center of rotation of the knee when the wearer is in an upright standing position. This position is determined by finding the junction between the femur and tibia on each side of the tibia and by observing the surface anatomy, with the appropriate position being identified by a bone protrusion on the femur and tibia respectively, between which is a "valley" or depression which runs in the anterior-posterior direction. If looking at the knee from the side, the location that the calf connection elements 107 will nominally pass through is approximately 30%-40% of the distance from the back side (posterior) of the knee. For some people, this is exactly the case. For others (e.g., large people, muscular people) the correct placement is determined on a case-by-case basis using an approximation and trial and error approach.

Desirably, the moments the soft exosuit 100 places on the wearer mirror those naturally created by the wearer (i.e., moments about the joint(s) that equal as closely as possible the natural biological moments during motion) so that the soft exosuit is transparent or otherwise substantially unobtrusive. In situations where joint moments from the soft exosuit 100 may be reversed from a natural moment for the movement at a given time, the soft exosuit 100 desirably minimizes the moment arm about the joint (e.g., to make the knee moment as small as possible by putting the connection elements 107 through the knee center of rotation).

In at least some aspects of the present concepts, the calf connection elements 107 terminate at the T-connector 113 where the Bowden Cable sheath 144 (see, e.g., FIG. 2A) connects to the soft exosuit. In accord with some embodiments, the T-connector 113 is positioned below the bulk of the calf muscle. The calf muscle is compliant and protruding and, accordingly, if the T-connector 113 is placed on it at the time of actuation, it will dig into the muscle thereby increasing the compliance in the system and causing user irritation. The space below the calf muscle is much less compliant and also allows the calf connection element 107 to descend down the shank in a straighter path as opposed to being angled more deeply to accommodate the calf's bulk. If the calf connection element 107 descends the shank at a greater angle with respect to the vertical, this makes the soft exosuit's force path less efficient, as it now wants to straighten when it is tensioned.

In at least some aspects of the present concepts, the calf connection elements 107 are positioned to circumvent the bulk of the calf muscle, which allows the calf connection elements 107 to descend the shank in a straighter line with respect to the vertical. The T-connector 113 at the end of the calf connection elements 107 can be positioned correctly with respect to the horizontal by positioning the T-connector 113 directly in-line with the center line of the heel. In order to position the calf connection elements 107 correctly with respect to the vertical, the connection elements are adjusted such that the T-attachment gets positioned at the top of the footwear (if worn) or nominally so that the T-connector 113 is located below the bulk of the calf muscle, which allows the calf straps to successfully circumvent the bulk of the calf. In accord with some embodiments, some of the more rigid components can be replaced with softer more compliant ones.

One or more footwear connection elements 130 are provided to provide a stiff interface with the user's foot. It at least some aspects, the footwear connection element 130 comprises a harness disposed around a proximal (e.g., heel) and a distal (e.g., upper, toe box, etc.) portion of a boot. Such a footwear connection element 130 relays the upward force due to the actuation at the heel to the front of the foot where it applies a downward force. Transferring the upward horizontal force to the front of the foot in such a way helps to promote ankle plantar flexion by virtue of the complimentary moments that are generated.

In at least some aspects, the footwear connection element 130 comprises one or more connection member(s) disposed to wrap around a middle portion (e.g., upper) the middle of the user's footwear (e.g., boot, shoe, etc.) and around the space between the footwear heel and the instep. The footwear connection element 130 comprises one or more connection member(s) disposed to wrap around the ankle, as shown, providing a constraint to keep the footwear connection element 130 from slipping off the heel and being tensioned upwardly to provide greater stiffness. One or more connection member(s) are also advantageously disposed to constrain the footwear connection element 130 from slipping medially and laterally relative to the footwear. In at least some aspects, a bottom edge of one connection member is advantageously placed about 0.5 cm about the edge of the heel of the footwear. This positioning results from a correct positioning of node 2. The footwear connection element 130 comprises a connection member serving as the actuator cable (e.g., Bowden cable, etc.) attachment point, which directly and/or through another connection member, transmits the actuation force to the heel. Node 2 is desirably placed as close to the bottom of the heel as possible in the vertical direction and directly in the middle of the heel in the medial-lateral direction. Node 3 is placed slightly behind the middle of the foot-sole and its position is dictated by the placement of node 2.

In one example of a method of donning the boot attachments correctly, Node 2 is first placed on the heel, and then the one or more footwear connection elements 130 are placed in appropriate positions relative to the footwear, following which the footwear connection elements are sequentially adjusted as needed (e.g., tensioned/loosened).

The footwear connection element 130 optionally, but advantageously, comprises one or more fasteners that may be adjusted (e.g., by tightening or cinching, such as by using Velcro®, etc.) to secure the footwear connection element around the wearer's foot.

In at least some aspects of the present concepts, the footwear connection element 130 comprises a sock-like structure that can be donned, much like a sock. Alternatively still, the footwear connection element 130 comprises a step-into structure that may then be folded over to envelop the foot, at which position one or more fasteners tightened or cinched (e.g., Velcro®, etc.) to secure the footwear connection element 130 around the wearer's foot. In at least some aspects of the present concepts, the footwear connection element 130 may comprise a one piece or multi-piece textile-based structure, in which webbing extends under the wearer's heel and over the forefoot.

The footwear connection element 130 may take the form of a harness, disposed over boots or shoes, which provided a connection point to the Bowden cable 142 actuator. These solutions are "out of boot" solutions on which the cable 142 pulls to create a force on the boot heel upward with respect to the heel. Other aspects of the present concepts include a footwear connection element 130 utilizing an "inside the boot" force actuator to create moments about the ankle joint, such footwear connection element comprising a cable attached insole and a cable guard. In such configuration, in order to apply forces to the wearer, a cable extends into the wearer's shoe or boot with one end fixed to the actuator external to the shoe (A) and the other affixed an object internal to the shoe under the wearer's foot (B) insole.

In another aspect, a plastic or foam element is optionally inserted in between webbing over the forefoot and the wearer's foot to distribute the pressure over the top of the foot more evenly than if the webbing was used in isolation. In another aspect, a midsole is combined with webbing (and optionally foam or plastic as previously noted) over the top of the foot and/or ankle, to provide additional paths for torque to transfer to the foot.

Attaching a cable or webbing at a lower rear part of an insole element, provides a fixed point at which forces applied to a point on the cable or webbing are transferred to the wearer's heel proximal to the ankle joint in the sagittal plane, creating torque around the joint. This insole can either be a partial or full insole. It may be desired that the insole have some stiffening elements such as carbon fiber to distribute load to the heel. If stiffening elements are used, the insole could advantageously be segmented to allow for maximum range of motion on the ball of the foot. In at least some aspects of the present concepts, a cable guard is provided at a rear portion of the lower leg. For actuation, the cable needs to retract. In situations where the cable is compressed between the boot and wearer's leg abrasion could result as well as loss in efficiency due to friction between the cable wearer and boot. Thus, a system that provides an open channel for the cable to freely move is desirable.

In various aspects of the present concepts, a sock-like footwear connection element 130 is connected to the soft exosuit 100 via a connection element (e.g., webbing) attaching to the top of the sock-like structure and goes directly up to the bottom of the calf connection elements 107. In yet another aspect, the footwear connection element 130 comprises a heel cup configured to wrap around the heel (e.g., the wearer's heel, a heel of the footwear). In still another embodiment, the footwear connection element 130 comprises an insole insert that goes into the footwear under a portion of the wearer's foot (e.g., the heel) or the entire foot, such insole insert, or the aforementioned heel cup, attaching at a rear portion and/or rear lateral portions to a connection member (e.g., webbing) that exits the footwear and attaches to the soft exosuit actuator cable. Desirably, any connection members disposed within the footwear comprises a low friction sheath, low friction coating, or low friction material so as to minimize friction against the wearer. In yet another aspect, the footwear connection element 130 comprises a sole insert that goes under a portion of the sole of the footwear (e.g., just the heel) or the entire sole of the footwear. A connection member (e.g., webbing, cable, etc.) is provided at a rear portion and/or rear lateral portions of the sole insert to connect to a connection member attaching to the soft exosuit actuator cable.

In accord with some embodiments of the invention, an actuator 200 can also be used to reduce the metabolic cost of walking (or other movements or activities) while wearing a soft exosuit 100 in accord with the present concepts. The actuator 200 is used to supplement forces of the desired moment, such as (for walking), supplementing forces about the ankle during the toe push-off portion of the gait cycle when the ankle muscles are generating the greatest power. To perform this action, by way of example, a motor can be used to create the necessary force/displacement on a Bowden cable 142 (or other flexible transmission element such as, but not limited to, webbing, ribbon material, belt, or chain) and sensors 150 (e.g., footswitch sensor 150 in FIG. 2A) can be used to sense joint position and determine actuation timing.

The actuator 200 generates a force that can be transmitted, at least in part, across one or more joints to a distal body part to impart a force to such distal body (e.g., by causing a cable 142 to change the distance between a point on the user's boot and the bottom of the soft exosuit, etc.). With a minimally extensible soft exosuit, this contracting distance generates a tensile force in the soft exosuit 100, footwear connection element (e.g., boot attachment), and cable 142. This tensile force can be applied at a position offset from the axis of the ankle joint and result in a moment about the joint. As one example, flexible Bowden cables 142 can be used by the system 100 to transmit forces from actuator(s) in an actuator unit 200 to the soft exosuit 100. Rigid and/or heavier actuator(s) 200 can be mounted remotely or distally (e.g., on a backpack away from the lower body), such as is shown in FIG. 2A.

In at least some aspects of the present concepts, each limb (e.g., leg) can be driven by its own actuator unit 200, which may comprise one or more actuators. In yet other aspects of the present concepts, each joint can be driven separately by its own actuator unit 200, which may comprise one or more actuators. In still other aspects of the present concepts, a plurality of joints can be driven by an actuator unit 200, which may comprise one or more actuators.

Figure 8:
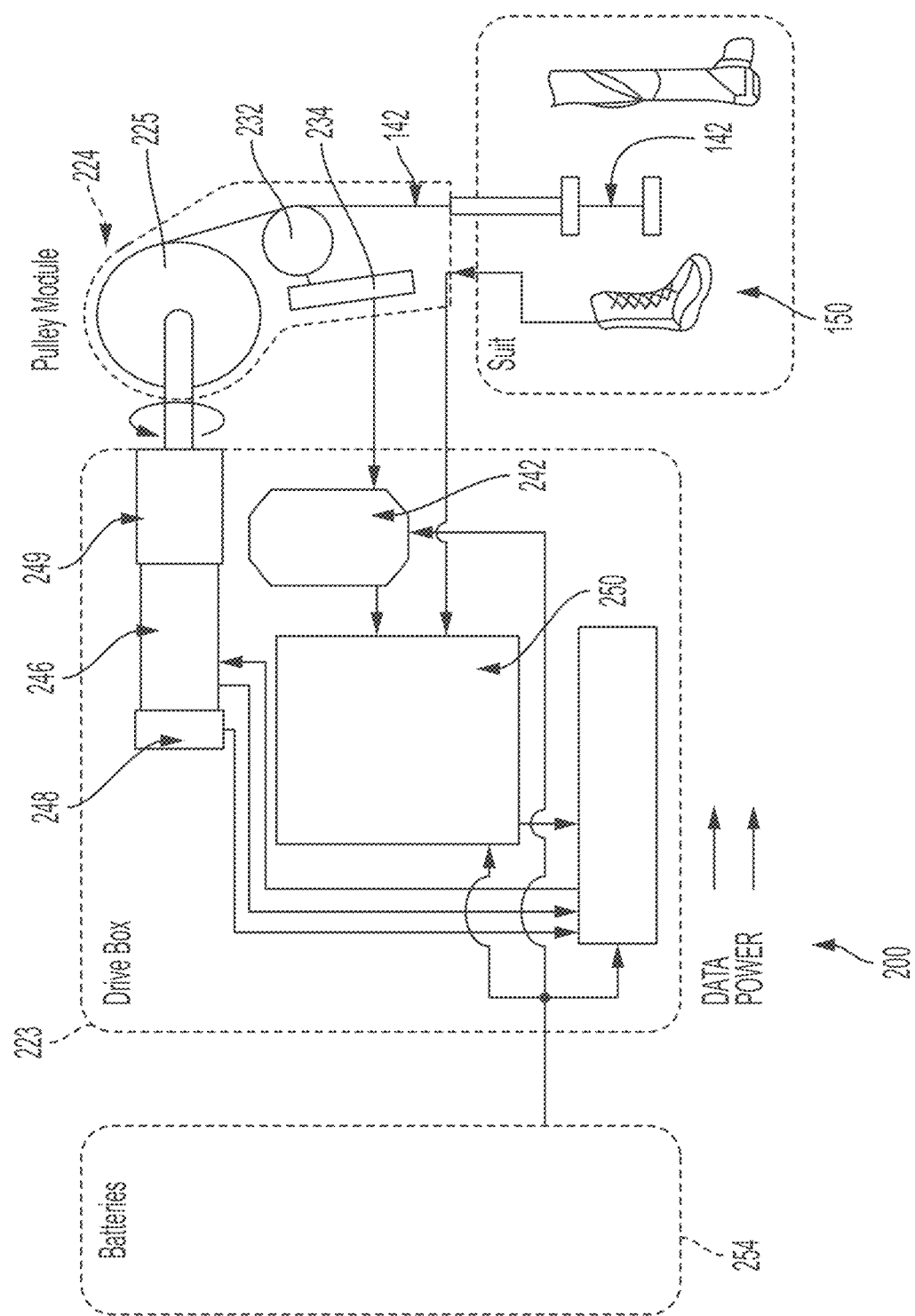
FIG. 8 shows a block diagram of an example of one embodiment of an actuation system for a soft exosuit according to at least some aspects of the present concepts.
Figure 9:
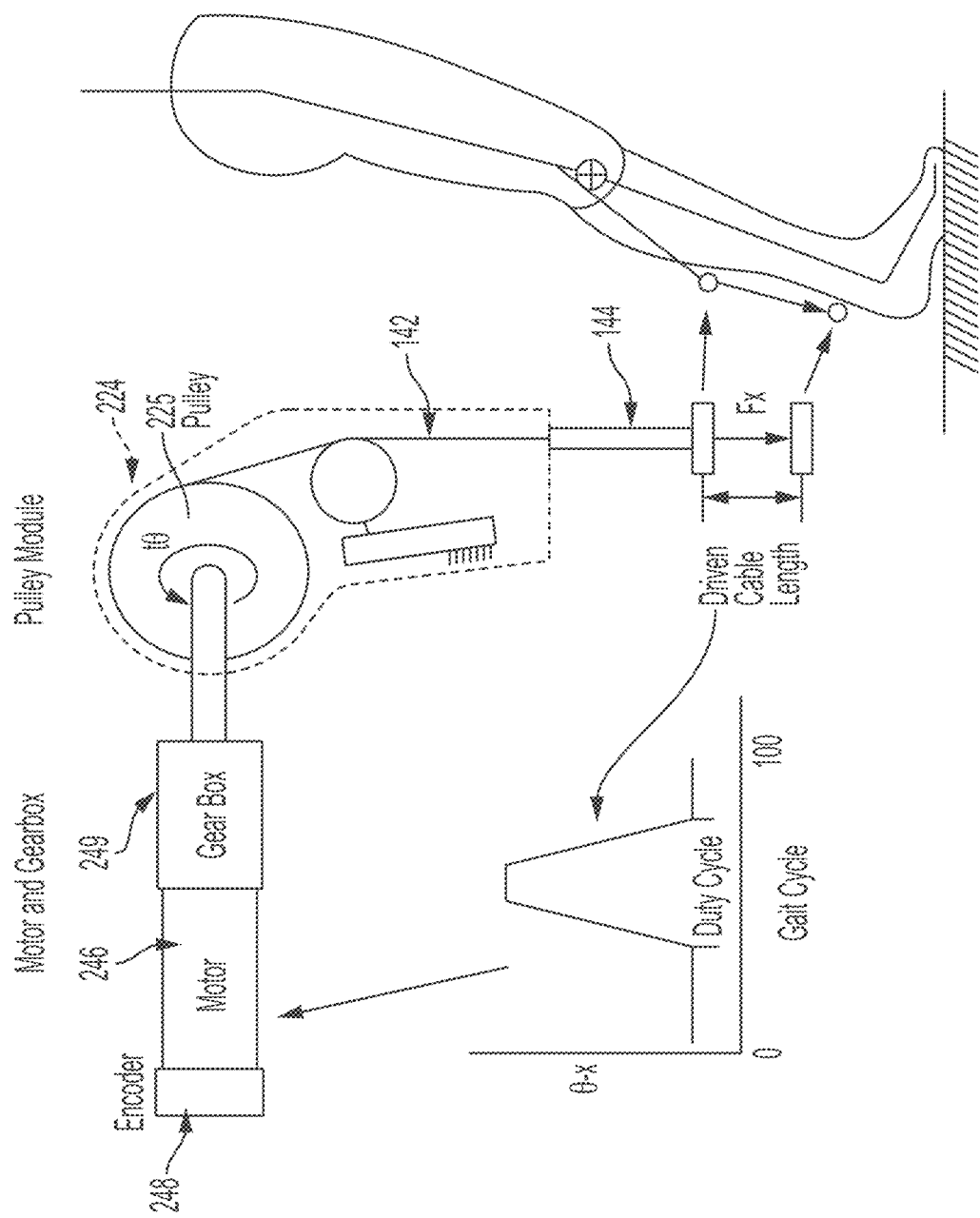
FIG. 9 shows a representation of the controlled actuation of the soft exosuit during a portion of a gait cycle in a soft exosuit according to at least some aspects of the present concepts.

In one embodiment in accord with the present concepts, shown in FIGS. 8-9, each actuator unit 200 includes a drive box 223 and a pulley module 224. The actuator unit 200 is used to drive a Bowden cable 142 and to sense the user's gait by measuring heel strike contact (see, e.g., foot switch 150, FIG. 8). The Bowden cable 142 is attached to a pulley wheel 225 in the pulley module 224 and is extended and retracted by rotation of the pulley wheel 125. In accord with some embodiments, the drive motor 246 includes gearing 249 (e.g., a gear box) to increase the drive torque of an output shaft coupled to the pulley module 224 to drive the Bowden cable 142 that provides the assist the user's motion. In other aspects, the motor 246 is connected directly to the pulley module 224 without intermediate gearing. The drive motor 246 advantageously comprises an encoder 248 or other positional sensor configured to indicate the rotational position of the motor output shaft. The drive motor 246 and encoder 248 are connected to a motor controller used to control the power, speed and direction of the drive motor.

In accord with some aspects of the present concepts, a centralized motor controller is provided to control more than one motor. Alternatively, each actuator unit 200 includes its own resident system controller 250 configured to receive sensor inputs and to communicate with the motor controller to control the operation of the drive motor 246 for that actuator unit. The system controller 250 (or optionally centralized motor controller) can include a computer or microprocessor-based system, such as, but not limited to, those based on the PC/104 standard. The drive motor 246 is coupled directly or indirectly (e.g., through a gear train 249) to the pulley module 224 comprising a pulley 225 engaging a proximal end of the Bowden cable 142.

As shown in FIGS. 8-9, the pulley module 224 comprises a housing adapted to engage the Bowden cable sheath 144 such that, when the pulley wheel 225 is rotated in a first direction, the Bowden cable 142 wraps around the pulley causing the distal end of the Bowden cable 142 to be retracted into the distal end of Bowden cable sheath 144 and, when the pulley is rotated in a second direction, the Bowden cable is unwound from the pulley, causing the distal end of the Bowden cable 142 to extend from the Bowden cable sheath 144. In at least some embodiments, the pulley 225 is enclosed in the housing such that, when it is rotated in the second direction, the cable 142 is driven out and can apply an extension force.

As noted above, in at least some aspects of the present concepts, a single actuator unit 200 may be used to provide energy to one or more limbs and/or one or more joints. As one example, alternating power transmission to separate limbs may be accomplished via a clutch switching power transmission between the limbs, which takes advantage of the out-of-phase movement of opposing limbs (e.g., the legs are typically out of phase during walking).

In at least some aspects in accord with the present concepts, the soft exosuit 100 control system is configured to sense or determine the gait of the user (e.g., via one or more sensors) and actuate the drive motor 246 to pull on the Bowden cable 142 during specific times of the gait cycle or to actuate another actuation system configured to introduce forces at specific times of the gait cycle (or other movement). Actuating the drive motor 246 at predefined points during the gait cycle can create a predefined tension in the soft exosuit 100 that applies a force about the ankle that aids in walking One or more sensors worn by the user (e.g., one or more foot switches 150, one or more joint angle sensors, etc.) are provided to transmit signals to the control system to enable the control system to synchronize the motor actuation with the user's gait cycle (or other movement). In accord with various embodiments of the invention, the sensor can take many forms, including sensors that sense the angular position of specific joints. See, for example, commonly owned WO 2013/044226 A2, which is hereby incorporated by reference in its entirety. In accord with some aspects, the sensors comprise a pressure sensor or a simple on/off switch that senses the pressure of the foot during the gait cycle, e.g., a heel-strike.

In accord with other aspects of the present concepts, one or more sensors can take the form of EMG sensors that sense muscle activation at specific locations. The pattern and scale of these activations can either determine gait cycle (pattern) or amount of assistance required (based on scale). Other sensors that detect joint position, relative or absolute, either with respect to ground or with respect to a point on the wearer, may be used to determine gait pattern and, therefore, can be used to control actuator activation. Other sensors can include, but are not limited to, hyper elastic strain sensors, accelerometers, inertial measurement units, internal measurement Units (IMU) and/or Goniometer sensors. These sensors, or other sensors, singly or in combination, can detect motion indicative of body position. Depending on the sensor(s) used, heuristics specific to that system are able to be developed to determine when the muscles in the body are applying force to a joint (e.g., such as the ankle, knee, or hip) so that the soft exosuit 100 can, in turn, be configured to apply force at the appropriate time and in proportion to the estimated muscle force. For example, one possible scheme would be to estimate the dynamics of the user's body by estimating velocities of each of the joints and, using an approximate rigid body model of the wearer, estimating torques at each joint, from which appropriate tension to produce resultant, beneficial torques are determined.

An alternate scheme would involve recording EMG measurements and sensors simultaneously in a training phase. After this data is collected, machine learning algorithms are used to predict when the muscles are contracting, as a function of the sensor inputs. Then, in practice, the EMG sensors would not be used, and instead the trained algorithm would predict muscle activation based on the sensors, and apply tension to the soft exosuit when the appropriate muscles would be activated.

Another scheme would involve directly measuring the muscle activation using EMGs, sensors which detect the muscle diameter, or some other means. Then, the soft exosuit 100 could be tensioned in proportion to the activation of certain muscles or combinations of muscles.

In accord with some embodiments of the invention, one or more foot switches 150 are positioned between the foot and sole of the boot to sense heel strikes to provide measurement of the rate of the user's gait cycle. The foot switch or sensor is used to detect the moment when the heel of each foot first hits the ground during the gait cycle, and the control system uses the signal from the foot switch to calculate the gait period. The position of the ankle at any point during the gait cycle can be estimated based on a known ankle position vs. time curve (assuming level ground and a nominal gate). The estimated ankle position can be used to determine when to retract the Bowden cable 142 and tension the soft exosuit 100. The tensioned soft exosuit 100 can provide a moment about the ankle during the toe push-off portion of the gait cycle to supplement the muscle supplied forces and reduce the energy expended by the user.

In some aspects, Velcro® or some other attachment mechanism is used to connect one portion of the soft exosuit 100 to another after being manually pulled to a desired tension. For example, node 1 (see, e.g., FIGS. 3, 5) can be connected to the waist belt 110 and to the thigh brace 120 using connecting elements have Velcro® fasteners. For example, in FIG. 7, connecting elements 4 and 5 loop through buckles on the thigh brace 120 at the bottom and then can be pulled upwardly and fastened down upon themselves with Velcro® or other fastening component(s). Alternatively, connecting elements 2 and 3 can each be secured at the waist belt 110 with Velcro® directly, without looping through buckles, or by another fastening member or element. Another option is to use a piece of webbing passing through a feed-through buckle preventing it from backing out after it is tensioned, and manually pulling taut the protruding end of the webbing.

In accord with at least some aspects of the present concepts, a force sensor is used to continuously measure the tension in each Bowden cable 142. An idler pulley 232 (see, e.g., FIG. 8) is biased against the Bowden cable 142 and a load cell 234 (see, e.g., FIG. 8) is used to sense the cable 142 tension. Alternatively, other means of sensing cable tension, or more generally flexible transmission element tension, may comprise a load cell disposed at a point at which the cable or flexible transmission element applies force to the soft exosuit. These measurements are logged and used to automatically tension the soft exosuit to an appropriate level. In accord with some aspects, the soft exosuit controller(s) 250 (e.g., system controller) detect(s) an increase in the tension of the soft exosuit due to natural body motion and applies actuation via the actuator(s) 200 based on this signal indicating an increase in tension. Thus, in various aspects, the soft exosuit controller(s) continuously monitor the force in the exosuit, or monitor the force in the exosuit at a sampling frequency appropriate to the user's motion(s), activity, or activities. When the soft exosuit is tensioned to some small amount because of geometric changes in the user's position, the controller(s) can sense that (small) force and actuate the soft exosuit to increase or decrease the tension, as appropriate. For walking, soft exosuit tensioning can be accomplished, for example, by applying a constant offset to the motor position signal from the control system. Of course, tensioning can also or alternatively be accomplished manually by the wearer by manipulating one or more adjustment members (e.g., straps, buckles, clasps, Velcro attachments, etc.).

In some aspects, the actuator unit 200 is configured to communicate with a local or remote external computer (e.g., a desktop or laptop computer, tablet or a smartphone) over a communication channel, such as Ethernet (e.g. wired or wireless—WiFi), Blue Tooth, I2C, or other open or proprietary communication channel. The external computer can be used, for example, to boot-up the actuator system control program upon first power up, adjust control parameters such as exosuit tension, execute diagnostic checks, transmit software, or even remotely control the actuator unit 200. In at least some aspects, the control system automatically boots on power-up and receives control inputs from switches on the exterior of the actuator unit 200 or on a hand held wired or wireless remote control or electronic device (e.g., smart phone app). In other aspects, the control system operates autonomously based on preprogrammed algorithms that detects or anticipates the intent or actions of the user and applies appropriate assistance.

In one example control system configuration, the actuator unit 200 (e.g., the actuator in the example of FIG. 8) is controlled by a Diamond Systems Aurora single board computer (e.g., processor 250) in a PC/I 04 form factor connected to a Diamond Systems MM-32DXA T analog and digital I/O expansion board. The computer can be powered from a 4-cell (14.8-16.8V) Lithium Polymer battery (e.g., battery 254) via a Diamond Systems Jupiter power regulation board. Tension in the Bowden cable 142 is sensed with a 50 kg beam-style load cell 234 (Phidgets, product code 3135) mounted against an idler pulley 232 in the pulley module 224. A full bridge strain gauge on the load cell 234 is connected to a signal amplifier 242 (e.g., Futek CSG 110) through an electrical interface (e.g., pogo pin). Each amplifier/load cell pair is calibrated by adjusting the output of the amplifier 242 while applying known loads to the load cell 234. The amplifier 242 outputs a DC voltage from 0-IOV corresponding to the force on the load cell 234. This voltage is read by an analog input pin of the MM-32DX-AT. The amplifiers 242 can be powered by the PC/104's 14.8V battery via their own on-board power regulators.

In accord with some aspects of the present concepts, the heel strikes can be sensed with foot switches 150 (e.g., FIG. 8), such as foot switches from B&L Engineering (product code FSW). The foot switches 150 can be foot-sole-shaped force sensitive resistors. The terminals of the heel portion of each foot switch 150 are connected to ground and a digital input pin of the MM-32DX-AT respectively. A 1 kΩ and a 10 kΩ resistor in parallel between each foot switch digital input and a +5V rail can pull the digital pin up. When a heel strike occurs, the resistance between the two terminals of the foot switch 150 drops, the voltage at the digital pin decreases to approximately zero, and the change in state can be read by the MM-32DX-AT I/O board. The foot switch 150 can be wired to a 3.5 mm audio jack, which plugs into a stereo cable and to a corresponding 3.5 mm audio jack in the pulley module 224. The electrical connection to the foot switch 150 can be passed through the pogo pin interface to the PC/104 computer 250. The audio jack permits easy disconnection of the foot switch from the rest of the exosuit, which facilitates donning and doffing of the soft exosuit 100.

In some aspects, the PC/104 computer 250 is connected to control switches on the outside of the drive box 223. Power switches are provided for each drive box to break the positive voltage lines of the PC/104 and motor controller batteries. Two momentary toggle switches and a rocker switch provide user input to the control algorithm running on the PC/104 computer 250. The rocker switch can be used to engage the walk mode of the control algorithm and the momentary toggle switches can be used to rotate the left or right motor to tension the soft exosuit prior to walking. These three user interface switches are connected to digital input pins on the MM-32DX-AT with 10 kΩ pull-up resistors and share a common ground with the PC/104. When each switch is activated, the digital input is connected to ground and the pin pulled low. In addition to, or in the alternative to, the box mounted switches, a small hand-held wired or wireless remote (not shown) can be provided. The remote's switches can be connected in parallel with the box's switches and provide duplicate functionality. In addition to, or instead of, the user input switches, other user interface systems can be integrated into the soft exosuit, including voice controls, a touch screen, wearable computer, or a heads-up-display (e.g., Google glasses or wearable display with retinal sensing or other input, such as a wirelessly connected track pad or softkeys).

In accord with some embodiments, the drive box 223 comprises a EC-4 pole 30 Maxon motor 246 connected to a Copley Controls Accelnet Panel ACP motor controller. A HEDL 5540 3-channel encoder 248 with 500 counts per turn with RS-422 digital signaling is used for feedback. Each motor controller is powered, by way of example, by two 4-cell (+14.8-16.8V) lithium polymer batteries in series for a total of +29.6-33.6V. The motor controller, in the example shown in FIG. 8, supplies the motor with up to +24V. The Accelnet Panel motor controller 260 can accept a DC voltage between −10 and 10V to change the angular orientation of the pulley and tension or slacken the cable 142. A −10V signal can move the pulley one full rotation in the counter-clockwise direction from the starting point upon power up and a +10V signal can rotate the pulley clockwise one full rotation. In accord with some aspects, the negative voltages are not used, since in operation the motor controllers 260 are powered on only when the cables 142 are extended out as far as possible. In software, the control signal can be limited to being positive to prevent damaging the system by running the motors into the physical stops.

The control voltage can be generated from one of the analog out pins of the MM-32DX-AT. To ensure smooth motor operation, the voltage signal is sent through a low pass filter. This filter can include an RC single pole construction with R=68Ω and C=47 µF, and provide a cutoff frequency of 48.9 Hz. The signal can additionally be filtered by the motor controller, which implements a digital filter operating on the analog input.

In accord with some aspects of the present concepts, each pulley module 224 include one or more indicators, such as a blue, green and/or red LED which illuminate to indicate various states of the system status (e.g., green illumination when the pulley module is correctly connected to the drive box 223). The power and ground for the LED(s) can passed through the pogo pin interface from the PC/104's battery. A 1 kΩ resistor can be used to bring the voltage from the battery down to a suitable driving current.

In accord with some aspects of the present concepts, the Bowden cables 142 are grounded via the metal pulley box 224 and drive box 223 shell, which serves as the ground for the circuitry inside. Grounding the Bowden cable 142 advantageously prevents the Bowden cable from acting like an antenna and transmitting electrical noise to the load cells and other components of the system.

In accord with some aspects of the present concepts, the actuator unit 200 uses a 200 W brushless motor 222 (which operates at a reduced duty cycle) to move the pulley 225 and cable 142 through the assistance trajectory. The pulley 225 converts the motors torque and rotational speed to a force and displacement that can be applied through the cable to the ankle (see FIG. 9).

Figure 10:
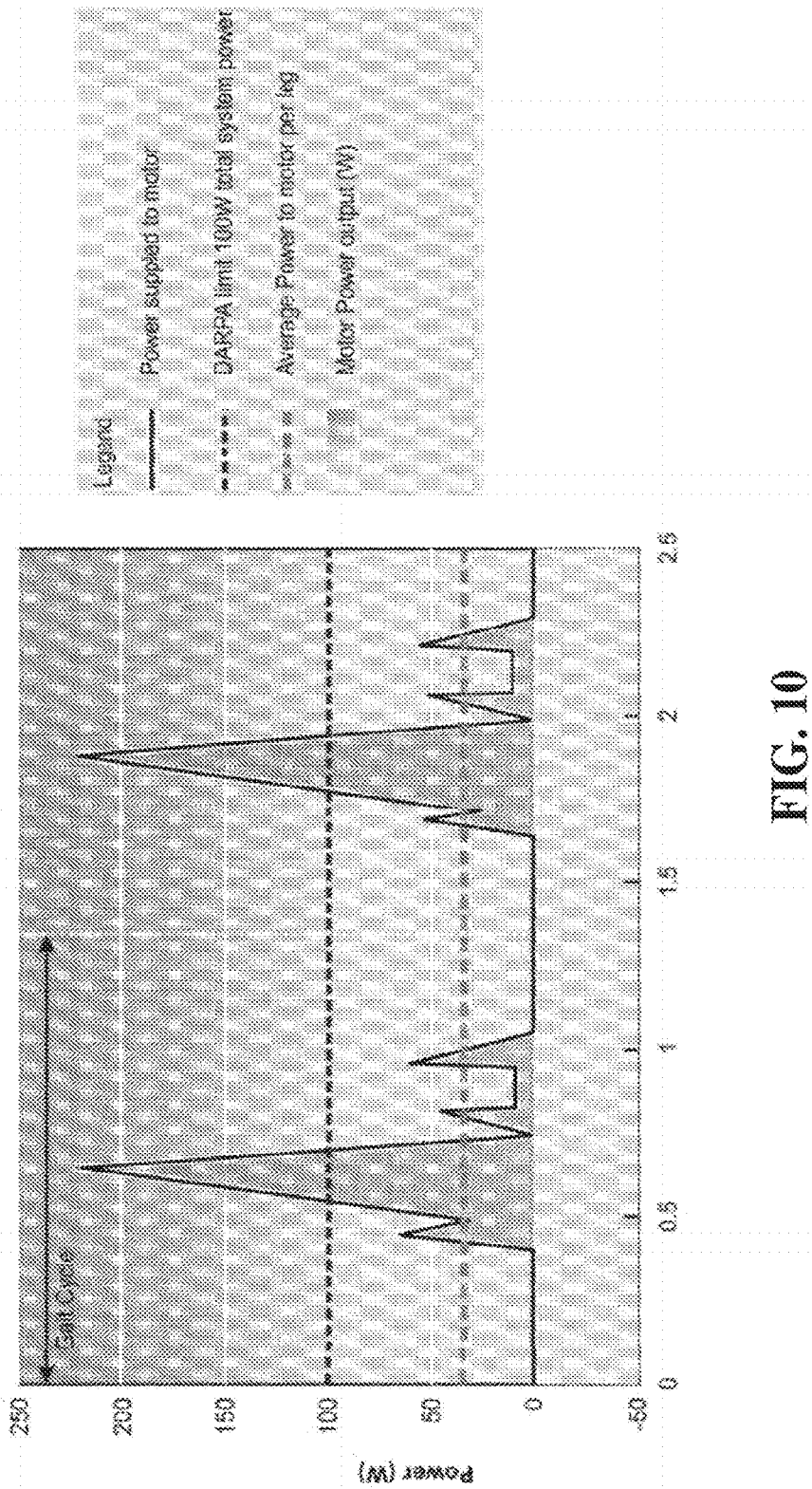
FIG. 10 shows an approximation of power input to a motor over a gait cycle in a soft exosuit according to at least some aspects of the present concepts.

The assistance provided by the actuator unit can be limited, for example, by motor supply power, which was 100 W in the soft exosuits under test, but is not a functional limitation. In the tested soft exosuits, the duty cycle of the motor 246 provided up to approximately 200 W for a portion of the cycle, then returning to a low power draw for the remainder of the cycle while maintaining an average power consumption at or below a working 100 W requirement selected for testing (FIG. 10).

In accord with some aspects of the present concepts, the EC-4 pole 30 brushless motor 246 by Maxon Motors can be used because it is a high efficiency motor that provides high power to weight ratio and a compact size. Other motors can be used depending on the performance requirements of the system. While a rotary motor was used in various examples above, other actuators can also be used including, but not limited to, electro-mechanical actuators (e.g., motors, solenoids, etc.), pneumatic actuators (e.g., pneumatic cylinders, McKibben type actuators, etc.) and hydraulic actuators (e.g., hydraulic cylinders, etc.). In yet other aspects of the present concepts, different types of motors can be utilized (e.g., high torque and low speed) that require no gearhead and consequently provide reduced weight, reduced noise and improved efficiency.

Further, while preceding examples disclose the cable actuator 142 system as comprising a pulley system 224 controlling movement of a Bowden cable, other actuators and/or flexible transmission members may advantageously be used with the soft exosuit. By way of example, any actuator capable of shortening the length of a cable or cord connected between two points having a sheath (Bowden cable) or not (Free cable described above) can be used. These actuators could be placed anywhere on or off the person, depending on the movement to be assisted, the context of such motion, contraindications, and the availability of alternative actuation placements. The actuator(s) may be distally located (e.g., in a backpack borne by the user's shoulders) with a proximal end of the actuator power transmissions element (e.g., cable) attached to a suitable location of the soft exosuit system (e.g., footwear attachment element 130) as described above. Alternatively, one or more actuator(s) may be disposed in between anchor points, connection elements and/or nodes, or over a portion of the length between terminal ends of the cable. Examples of other types of actuators can include, but are not limited to, one or more pneumatic or hydraulic linear actuators, pneumatic or hydraulic rotary actuators, ball or lead screw actuators, belt or cable driven actuators, electro-active polymer, etc.

In accord with other aspects of the present concepts, actuators which reduce the length between the terminal ends are used and include one or more semi-passive actuators, such as a magnetic or mechanical clutch. These actuators would engage at a point in the gait where the length between points is shorter then when assistance should be given (e.g., when the knee is bent). In conjunction with a retractable length of cable such that it has a minimum level of tension, the clutch would lock the length at shorter state such that when the leg naturally extended, force would be generated due to the stretch in the soft exosuit and cable. This would be classified as a semi-passive system and would be expected to require a lower energy level than active systems.

In accord with the other aspects of the present concepts, various mechanisms can be used to adjust the tension in the soft exosuit. In some embodiments, the same mechanism that actuates the soft exosuit can also be used to adjust the tension in the exosuit. In other embodiments, a separate mechanism can be used to tension the soft exosuit, singly or together with an actuator. The soft exosuit can be actively shortened using an actuator which reduces the length between two points on the suit. One mechanism that could accomplish this is a motor pulling on a Bowden cable, the sheath of which is connected to one point on the soft exosuit and the center of which is connected to a different point on the suit. This can be accomplished using, mechanical pneumatic, hydraulic, or other actuators.

Of course, as previously noted, the tension may be adjusted manually at one or more points by physical adjustments to the relative positions of the connection elements, anchor points, and nodes (e.g., adjusting straps using buckles and/or Velcro®, tensioning a drawstring, wire or cable and locking it in place, etc.). As another example, the wearer could pull on a webbing strap passing through a locking buckle, which secures the webbing strap after release. In another example, the wearer could pull on a piece of webbing (e.g., a connection element) and secure the webbing with Velcro® to a part of the suit.

The wearer could also pull on or otherwise tension a cable passing through a ratchet mechanism (e.g., a rotary ratchet mechanism, such as made by made by Boa Technology Inc., disposed on the waist belt 110) or lockable spool configured to secure the cable in place at a set tension. The ratchet mechanism or spool it attached to one end of a Bowden cable (e.g., at a top of the cable where the ratchet mechanism is hip mounted), the other end of which was connected to two locations on the soft exosuit to reduce the distance between them, with interacting elements (e.g., pawl element, ratchet element) providing releasable securement. The wearer could also advance a ratcheting mechanism by rotating a central hub around which a cable is wrapped, or could tension the soft exosuit with a screw mechanism that is then locked into the final position. Tension can be released by pushing a button to release the interacting elements of the ratchet mechanism (e.g., to move a lever away from ratchet gear teeth). The ratchet mechanism or spool can either be turned manually (to tension or de-tension) by the soft exosuit wearer or by an actuator, for example a geared motor. Even where a soft exosuit is not being actuated as an assistive system, the soft exosuit may still be worn in a tensioned mode. In various configurations, the ratchet mechanism can be located at the wearer's waist or hip (so as to facilitate adjustment while walking or running), near the ankle, or potentially elsewhere on or about the wearer's torso.

In accord with some embodiments, a mechanism to tension the soft exosuit can include a screw element. In one aspect, a carriage element is connected to an end of a Bowden cable and is configured to move up and down by means of a threaded portion in which a screw element is disposed. A support structure holds the carriage element in place relative to the cable sheath, and a top portion of the screw is exposed to the user to permit rotation of the screw. Rotation of the screw causes a linear movement of the carriage and the attached Bowden cable end, thereby increasing or decreasing, respectively, a tension in the soft exosuit. An optional locking element in provided to minimize the potential for loosening of the setting. In one aspect, the screw could be controlled by a small motor or other actuator to turn the thread, in which case no locking element would be needed.

As previously noted, the soft exosuit can optionally be actively tensioned (e.g., cable shortened or lengthened) is accord with a program as the user of the soft exosuit moves. Alternatively, in other aspects, the soft exosuit is automatically tensioned using one or more actuators, and maintained at one or more set tension(s) (e.g., a fixed value, a fixed range of values, different values or ranges of values for different portions of movement, a nominal average value, a nominal peak value, etc.), the set point(s) of which could be adjusted by the user. In this respect, the system is configured to sense the tension in the soft exosuit to provide appropriate inputs for the controller controlling the tension.

With all of these mechanisms, the soft exosuit can be made to be loose-fitting on the wearer by releasing these tensioning mechanisms, such as to facilitate doffing of the soft exosuit. Such tensioning (or detensioning) devices permit a user, for example, to retain a first level of tension between certain points on the soft exosuit and a second level of tension (higher or lower than the first tension). The soft exosuit advantageously comprises multiple tensioning mechanisms capable of operating simultaneously.

During the gait cycle, the motor(s) 246 can operate over a range of torques and speeds to achieve the desired cable 142 trajectory. Since higher motor efficiencies occur at high speeds and low torques, some embodiments of the invention can select a combination that includes a motor with a pulley and gearbox that keeps the motor operating as close to maximum efficiency as possible during the gait cycle.

In accord with some embodiments, the Maxon EC-4 pole 30 has a nominal continuous speed of 15,900 RPM. However, for this embodiment, the motor is limited by the max speed of the encoder: 12,000 RPM. An alternative encoder (MR, Type ML, 500 CPT, 3 Channels, with Line Driver Maxon #225778) can be used in the actuator system would increase the maximum motor speed.

In accord with some embodiments of the present concepts, a better motor for this system would have a lower nominal continuous speed for higher torques. A lower operating speed would reduce the number of necessary stages in the gearbox and would result in a higher overall efficiency.

In accord with some embodiments of the present concepts, the pulley 225 and gearbox 248 convert the motor's fast rotation into cable 142 lengthening and shortening movements driven by the pulley wheel 225. The pulley wheel 225 and the gearbox 248 together determine the maximum cable travel and the maximum cable speed for given load states. The pulley wheel 225 diameter and the gear reduction can be determined by working backwards from the minimum cable travel needed and the maximum cable speed required to meet the biomechanics and exosuit stiffness needs. The total amount of assistance was driven by these two limits, as well as the power budget.

In accord with some embodiments of the present concepts, the pulley wheel 225 can be a single wrap design, while in other embodiments, the pulley can be a multiple wrap design. With a single wrap design, the pulley wheel 225 circumference cannot be less than the cable travel distance. In accord with some embodiments, the cable travel can be based on the soft exosuit 100 architecture and biomechanics of walking of the user. In accord with some embodiments, the cable travel can include three lengths: cable pull length, exosuit tension length, and a margin of safety to prevent bottoming out. In accord with some embodiments, the cable travel was given a significant safety length due to uncertainty in design parameters and user variability. The cable pull length and the cable tension length were measured from the soft exosuit and previous actuator system with participants ranging in height from 5'8" to 6'5". The three lengths and calculated pulley diameter can be seen in Table 1.

TABLE 1

| | | |
|---|---|---|
| Cable pull length (Lp) | 8 cm | Length needed to assist foot given the lever arm to the back of the boot + the soft exosuit stiffness |
| Cable tension length (Lt) | 5 cm | Length needed to tension the soft exosuit prior to walking. Takes up slack in the system due to wearer differences |
| Cable safety length (Ls) | 7 cm | Length needed at the end of travel to prevent bottoming and to accommodate various sized people or added pull length |
| Total Length (Lcirc) | 20 cm | |
| Pulley diameter | 70 mm | Distance over circumference multiplied by working revolutions |

In accord with some embodiments of the present concepts, the use of a single wrap pulley resulted in a usable angle of 340° (0.94 revs). The selected pulley diameter of approximately 70 mm provided appropriate cable length. In general, a larger pulley and a larger bend radius provide less wear and reduced cable stress, whereas a smaller pulley or shaft can provide a much higher transmission ratio.

Figure 11:
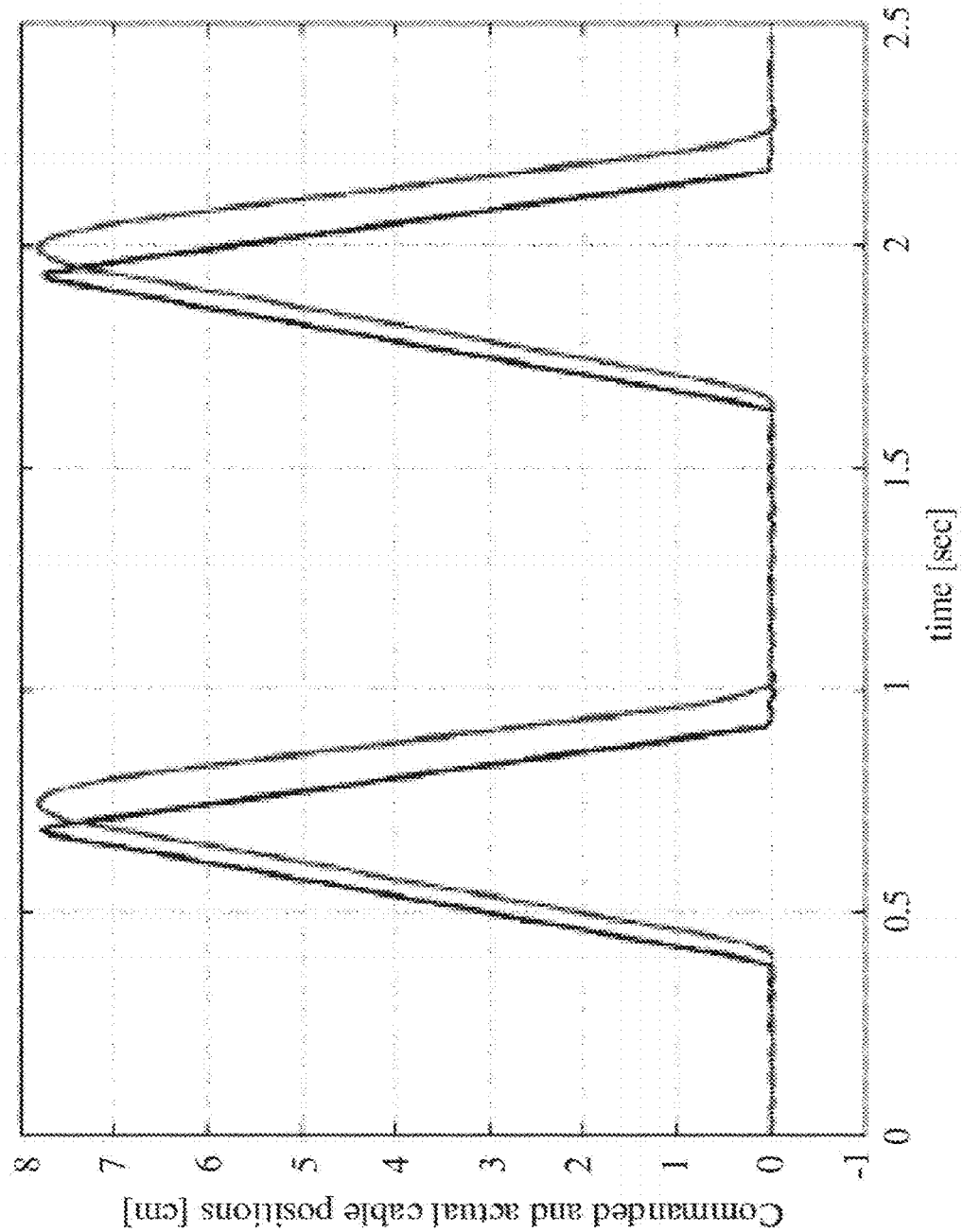
FIG. 11 shows an example of a plot of cable displacements as a function of time in a soft exosuit according to at least some aspects of the present concepts.

In accord with some embodiments of the present concepts, the gearbox 244 is chosen to meet the maximum speed required during cable pull and release when assisting the ankle. As seen in FIG. 11, the cable displacement for maximum assisting case can be treated as a triangle operating over the active portion of the cycle. The leading line is the commanded motor position signal in units of centimeters and the following line is the resultant motor position as measured by the CME-2 motor controller software scope. A positive displacement corresponds to a retraction of the cable and the delay between signal command and motor movement stems from acceleration limit of the motor controller.

As seen in Table 2, which shows gear reduction calculations in accord with at least some aspects of the present concepts, the maximum cable speed was found to be 37 cm/sec for the given pulley diameter (70 mm) and maximum motor speed. From the maximum cable speed, the necessary gear reduction was found to be 107:1 and a gearbox with a reduction of 111:1 was selected.

TABLE 2

| Variable | Value |
|---|---|
| Gait Cycle (T) | 1 sec |
| Duty cycle ($p_1 - p_2$) | 40% to 83% |
| Length of pull and release over duty cycle (Lp) | 8 cm |
| Maximum cable speed ($V_{cable}$) | $1 Lp/T(p_2 - p_1) = 37$ cm/s |
| Pulley diameter (D) | 7 cm |
| Max motor speed limit | 12000 RPM |
| Gear reduction (R:1) | $R = (M_{speed}/60)/(V_{cable}/L_{circ}) = 107$ |
| Selected gearbox reduction | Closest gear reduction is 111:1 |

It is desirable for the motor to operate within its speed-torque curve and that forces applied during high speed pulls do not exceed the motor's limits to preserve the life of the motor.

In accord with some embodiments of the present concepts, a Bowden cable is utilized that includes an inextensible cable translating inside an inextensible sheath. The Bowden cable 142 transmits forces from the actuator unit 200 to the ankle (via forces transmitted to a footwear connection element 130). The Bowden cable sheath 144 is attached to the soft exosuit and actuator unit 200 and the cable 142 is anchored to the footwear connection element 130. Webbing and/or cables are optionally routed through guides in the fabric of the soft exosuit.

In accord with at least some embodiments of the present concepts, the current system tension in the cable is input to the control system for data logging and pre-tensioning of the soft exosuit prior to walking Sensing tension in the cable can also be used in a gait control algorithm. The pulley module's 224 load cell 234 can be mounted to a small idler wheel which deflects the cable by a small angle as it passes from outside the box to the pulley. In general, the force required to deflect the cable increases linearly with the tension in the cable.

In accord with some embodiments of the present concepts, a B&L Engineering foot switch is mounted in the user's footwear and provides a range of sensitivity to enable activation by a user within one or more specified operational weight range). When not compressed, the foot switch has a nominal resistance of a few hundred mega-ohms, creating an effective closed circuit. The resistance drops down to 14Ω during heel strike (around 300 lbs. of force), a value much less than the 909Ω pull-up resistance (1 kΩ in parallel with 10 kΩ, which pulls the PC/104 digital pin low. The 11 kΩ resistor was added in parallel with the 101 kΩ resistor to minimize on/off toggling during transitional motions, such as when the heel strikes and when the heel is lifted up.

As configured in the tested configurations of soft exosuits, a Diamond Systems Aurora PC/104 computer 250 having a 1.6 GHz Intel Atom CPU, 2 GB of RAM was used and booted MS-DOS with a real-time kernel from a 4 GB SSD disk. The MS-DOS installation can be configured to launch an xPC Target binary executable on startup. The xPC Target application waits for a connection from the host computer, receives a compiled program from MATLAB/Simulink on the host computer, and executes the program. The Aurora PC/104 can be paired with a Diamond Systems MM-32DX-AT I/O expansion board to provide 32 analog inputs, 4 analog outputs, and 24 digital pins assignable as inputs or outputs. In accord with some embodiments of the present concepts, the PC/104 xPC Target combination provided a useful amount of processing power and flexibility. The PC/104 has a desktop CPU capable of 48.2 FLOPS and 2 GB of RAM, and control algorithms can be developed for use in the invention without worrying about speed or memory. The small size and low power consumption make the PC/104 suitable for use in a portable system. In accord with some embodiments of the present concepts, the Copley Controls Accelnet Panel ACP motor controller is a high performance controller capable of velocity control and position control. It has numerous command inputs (RS232 serial, CAN, PWM, analog voltage). The Copley Controls software allows basic auto-tuning and calculations of controller gains.

In accord with some embodiments of the present concepts, a Futek CSG110 was used as a general purpose amplifier for the full bridge strain gauges. The Futek CSG110 has DIP switches for setting excitation voltage and the mV/V sensor range as well as rotary potentiometers for calibrating the zero point and span of the DC voltage output to each particular load cell. The Futek CSG110 amplifier allows the load cells to be interfaced with the PC/104.

In accord with some embodiments of the present concepts five batteries are used to power this system. Four Gens Ace 14.8V 4S1P 5000 mAh 40 C lithium polymer batteries are used to power the motor controllers and motors, two per drive box (one drive box per limb). Each pair of batteries is wired in series in order to supply the motor controller with 29.6V DC. The fifth battery is a lithium polymer Gens Ace 14.8V 2S1P 4000 mAh 25 C that is used to power the PC/104 computer, both Futek amplifiers, pulley module LED's, and a cooling fan in each drive box. The PC/104 battery can share a common ground with the motor controller battery pairs and every component in the system. Batteries in accord with some embodiments of the invention could be an attachment to the system. These batteries could be contained in a housing with a terminal connector contacting at least 2 electrical connector blades capable of carrying greater than 200 W. These blades could interface with mating connector inside the motor hosing to form a power connection capable of powering the motors. The battery housing and motor housing could have mating retaining features such as latches to secure the housings making a quick release interchangeable system.

Lithium polymer batteries were selected because they provide acceptable performance in this application. Lithium polymer chemical construction provides one of the highest energy storage to weight ratios and is more robust and safer than lithium ion. In other embodiments of the invention, the soft exosuit may include energy harvest elements (e.g. from sun, wind, natural body motion, body heat, vibration, inductive coupling with a charging station, corded Li battery charging port, etc.) to reduce the overall battery size required to power the suit.

In accord with some embodiments of the present concepts, the control scheme can include the process of deciding how to move the motors based on the input from the sensors. The control scheme can be implemented in the code that runs on the PC/104 embedded computer. In accord with some embodiments, the control scheme can be written in Simulink blocks and MATLAB code. Simulink blocks for the MM-32DX-AT analog expansion board can handle input and output (e.g., I/O). One Simulink block can be used to read values for all the sensors and another Simulink block can be used to send the position values to the motor controllers. Additional Simulink blocks can be used to capture data and save it to the PC/104's disk or send it to a host computer for saving or debugging. The bulk of the processing can be accomplished by a MATLAB script embedded in a Simulink block. This MATLAB script can use the foot switch states, user interface buttons, and the current time step to calculate the desired motor positions. In accord with some embodiments of the invention, the Simulink block diagram can run at a fixed time step of 0.001 seconds (1 millisecond) on the PC/104.

In accord with some embodiments of the present concepts, the motor 246 outputs for each leg can be calculated from a trapezoidal trajectory, generated prior to runtime. This trajectory has a unit width and a variable peak height corresponding to the level of actuation desired (e.g., a pulse with a 4 cm amplitude, a pulse with a 6 cm amplitude). The cadence of the user's gait can be calculated from the timing between multiple heel strikes. In particular, the gait period can be recorded for a predefined number of steps, for example, the previous 20 steps, and the average taken. A twenty step moving average proved sufficient for a low pass filter. This average gait period can be used to scale the trapezoidal trajectory across one full gait cycle for each leg. Each leg can be treated independently and the waveform for each leg can be calculated independently. In some embodiments, both legs can be treated the same and the same calculated waveform can be used for each leg.

Upon heel strike, the control scheme can use a look-up table to generate the required motor pull. The flat trajectory from 0-40% of the Gait Cycle (GC) acts as a delay, keeping the soft exosuit slack as the foot is planted on the ground and the user's hip pivots into position above the foot. Starting at 40%, the motor pulls the cable in and tensions the soft exosuit to the maximum level at 62.5% GC when toe off occurs. After a period of holding, the motor then unwinds the cable back down to zero at 83% GC and resets for a new cycle.

The trajectory can be limited by the physical performance of the motor 246, gearbox 244, and Bowden cable 142. The downward slope of the trajectory can be bound by the maximum slew rate of the motor. Additionally, the motor controller can limit the maximum acceleration of the motor to 2500 rotations/sec$^2$ and the maximum velocity of the motor to 11500 rpm, effectively rounding the sharp corners of the trapezoidal trajectory and shifting it slightly (~3%) to the right. Finally, this trajectory can be generated based on ankle position vs. time charts that begin when the heel first touches the ground. The foot switches used in this system require a significant amount of pressure to trigger and thus a heel strike is not sensed until the heel is on the ground and the user's weight has begun to load the foot. This occurs at somewhere between 2-6% in the nominal gait cycle, most likely 2-3%.

In accord with some embodiments of the present concepts, the user interface switches are provided on the outside of the drive box 223, on a handheld remote, or via a wireless device, to modify the way the control scheme functions. When the walk switch is disengaged, the control scheme can optionally continue to run, but does not output pulse signals after heel strikes. Each tension toggles adds or subtracts an offset to the motor positions looked up from the trapezoidal trajectory. The offset grows in magnitude depending on how long a tension toggle is held down.

In accord with some embodiments of the present concepts, the value of the force sensors can be data logged and used to adjust the magnitude of the trapezoidal trajectory, but not used to calculate the desired motor positions. In accord with some embodiments of the invention, the force sensors can be incorporated in a feedback loop to follow a desired force trajectory throughout the gait cycle instead of desired motor position.

In accord with some aspects of the present concepts, a direct line cable can be used instead of a Bowden cable. A direct line cable can include a free cable from the actuator to the point of action. This will create a force in line with the cable between the two end points. In accord with other aspects of the present concepts, a multi-point cable system is used. For example, a multi-point cable system can include a free cable from the actuator 120 that passes through angle transition points along the path to the distal end and transfers forces and displacements along its length through some or all of the transition points including the end. Moments about each joint between the ends of the cable depends on their location with respect to the transition points of the free cable. The cable or webbing can be configured to slide with respect to the transition points and the wearer, unlike the Bowden cables where the cable is shielded until exiting the end. A multi-point cable and/or direct cable can include one or more of a wire or filament rope, webbing, such as the soft exosuit material, an elastic element (e.g., rubber) or any other flexible force transmission element.

In accord with some embodiments of the present concepts, Textile based force sensors can be used to measure linear displacement of woven fabric webbing between two points A and B. This linear displacement measurement can be combined with the properties (e.g., elastic properties) of the woven substrate to a calculated force measurement. The force can be measured along the collinear line formed by points A and B and terminating at the end points of that line where fabric meets other connectors. Woven webbing generally provides a strong durable fabric typically made in ribbon form (e.g., length, width, and thickness). Applying force linearly along the length of the fabric causes a stretch (strain) in the fabric. This stretch has been measured and is relatively consistent such that a force applied to the fabric will result in a specific strain measurement. Using this property the textile based force sensor can calculate the force based on the measured strain (e.g., measured strain in about the 0.05-5% range). In accord with some embodiments of the present concepts, a textile based force sensor can be used to aid in control of one or more exosuit actuators. The force measurement combined with actuator position measurements and force displacement profiles can be used by the control system to detect motion and provide feedback. It also aids in determine correct position of suit elements (via a stiffness measurement).

In accord with some embodiments of the invention, textile based force sensor can be used for recoding of forces in the soft exosuit elements during any activities, to aid in development by measuring forces in specific areas of the soft exosuit, to detect injury by measuring joint angles, and to detect joint angles either for control or data analysis.

In accord with some embodiments of the present concepts, the sensors can be placed at various locations on the soft exosuit. In one aspect, a surface based sensor is adhered to or attached to a connection element (e.g., woven webbing fabric) or other element at two points along a length of the connection element or other element. In another aspect, a full surface sensor is adhered to or attached to a connection element (e.g., woven webbing fabric) or other element at two points over an area of the connection element or other element. In another aspect, a pocket is formed in or woven in (for a woven material) a connection element or other element and a sensor is placed in the pocket (the material properties of the pocket would need to be used when calculating force). In yet other aspects, a sensor is constructed into the webbing directly. In still other aspects, the connection element or other element bearing one or more sensor elements (of any type) is a layered material or a composite material and the sensor(s) are disposed internally between layers of the layered or composite material.

In accord with some embodiments of the present concepts, sensors which measure linear displacement can be used in the system. Preferably, the sensor can be capable of measuring strains in the range of about 0.05-5% for current webbing. Traditional strain sensors with a medium strain range generally include those with a strain range 0%-10%. Other sensors include hyper elastic sensors with a large strain range (e.g., liquid metal such as disclosed in WO 2013/044226 A2, which is hereby incorporated by reference in its entirety). Alternatively, traditional strain sensors with low strain range can be used by making the area where strain sensor is attached very stiff to lower the webbing strain.

Figure 15A:
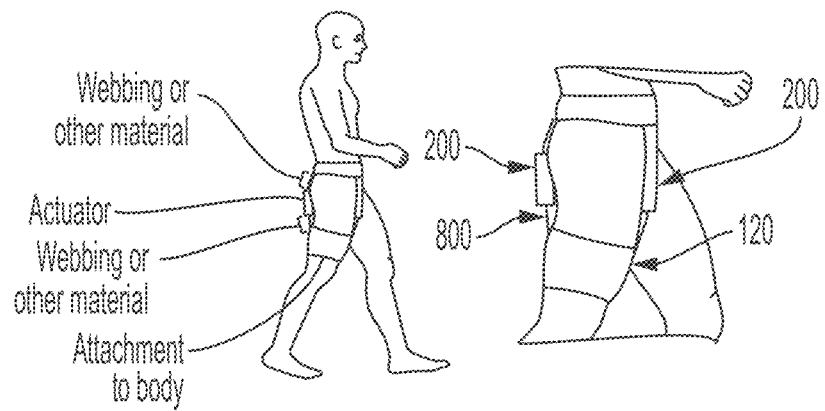
FIGS. 15A-15B show aspects of a soft exosuit in accord with at least some aspects of the present concepts.
Figure 15B:
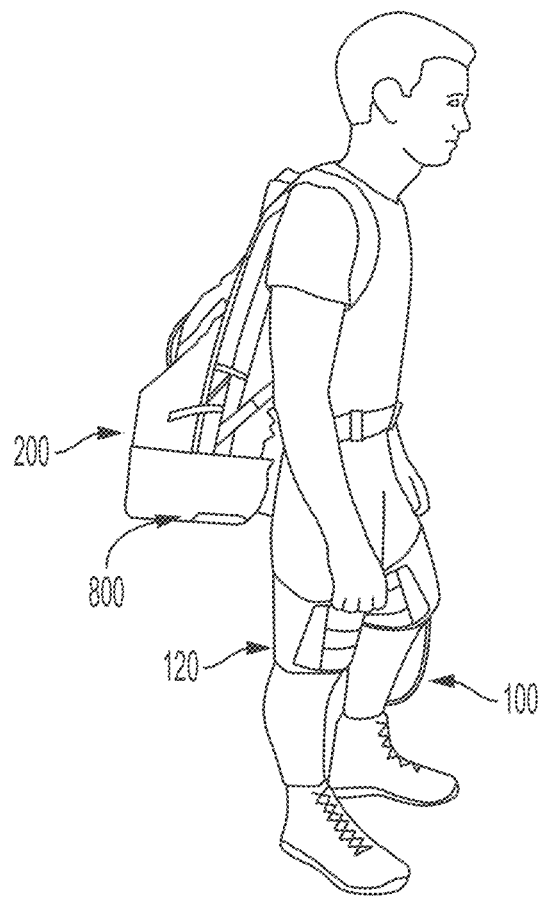

In accord with some embodiments of the present concepts, such as is shown by way of example in FIGS. 15A-15B, actuation can be provided at the hip joint to assist with motion and, in particular, walking, running and jumping. Also, as the hip joint is close to the torso, force can be transferred directly from a torso-mounted actuator or shoulder-mounted actuator to the hip joint itself. The actuator(s) 200 can be attached to a person such as by a waist belt or a backpack (as shown in FIG. 15B) and the actuator(s) and other appurtenant components (e.g., power system, etc.) can be adjacent thereto or alternatively distributed on the posterior side, anterior side, or both to distribute the system mass. The application of forces across the hip can be accomplished by pulling on the hip, on a distal end, with a tensile element (e.g., 800) such as a cable, piece of webbing, ribbon, etc., that is attached at a proximal end to an actuator 200. With no sheath required for this tensile element, the friction will be very low and thus the efficiency of the system high. One benefit of the hip joint being located close to the torso is that donning and doffing the soft exosuit is readily accomplished. The actuator, located on a backpack or fanny pack structure on top of the user's clothing, and the tensile elements can remain outside the body and secured to the thigh with a brace that is also outside the clothing and thus provide for a low-profile device that is easy to attach to and remove from the thigh.

The soft exosuit 100, in accord with at least some of the present concepts, comprises an actuator unit with a length of webbing, strapping, cable, or another other means of applying tensile forces (called the "ribbon" henceforth) 800 extending from it and attaching to the hip. In operation, the actuator 200 can retract the ribbon to create forces causing the hip to extend, and extend the ribbon causing the ribbon to slacken.

When the actuator 200 retracts the ribbon, the ribbon will tend to push into the gluteal region if the hip is flexed due to the change in angle of the ribbon. To prevent discomfort from this configuration, several solutions are possible. One is to have the ribbon offset from the body to some extent at the actuator end, such as is shown in the left, center of the above figure. This will increase the hip angle that can be reached before the ribbon pushes into the gluteus. Another option is to have a wide ribbon (e.g., 2"), to minimize pressures on the wearer. A low-friction material also may be worn on the gluteal region to reduce friction and increase comfort of the ribbon moving against the body. A sheath may also be used over a large length of the ribbon, i.e. a Bowden cable could be used, to protect the body from motion of the ribbon. An alternate means of reducing pressures on the body is to offset the distal end of the ribbon at the thigh attachment. This could be accomplished with rigid or semi-rigid components attached to the thigh brace, which may extend backward as a "spur" to provide an offset for the ribbon connection point from the thigh. For example, in one embodiment of a hip attachment system, a piece of fabric can be secured around the thigh with Velcro in the front. The actuator can attach to this thigh brace with a 2" wide ribbon, and the top of this ribbon can be pulled upward. The thigh brace is restricted from moving up the user's leg due to the conical shape of the thigh. Also due to the conical shape, there is little to prevent the thigh brace from moving downward, and so it can have a tendency to slip down the leg if there is no tension on the ribbon pulling it upward. The thigh brace can be held upward by other elements connected it to a waist belt, or by other means.

In some aspects, an actuator 200 flexible transmission element (e.g., ribbon, webbing, cable, belt, etc.) extends down over the gluteal region of the user and connects directly or indirectly to a soft element that engages the thigh (e.g., thigh brace). In one aspect, a rigid or semi-rigid spur can be used to create an offset from the back of the thigh. In one example, a semi-rigid element is connected at the back of the thigh and, as force is applied via the ribbon to the bottom of the semi-rigid element, it bends outwardly from the thigh, thus increasing the offset (and moment) from the thigh. This could be useful for creating a low-profile suit that collapses against the body when not in use, and creating a larger moment arm when large forces are needed. At intermediate forces, the moment arm could be in an intermediate position. Many other configurations of elements, each having different amounts of stiffness can be used in a single system, including various arrangements of soft, flexible, rigid, and semi-rigid elements. Springs and other elastic elements can also be included as elements of the system for regenerative purposes.

In accord with one or more embodiments of the present concepts, the actuator 200 comprises a motor driven drive pulley adapted to engage and wind the ribbon in response to control signals from a control system. The drive motor can be connected to the drive pulley using a transmission. The transmission can include a timing belt and timing gears or a set of gears that transfer power from the drive motor to the drive pulley. In alternative embodiments, a drive shaft and one or more gears or timing pulleys can also be used to connect the drive motor to the drive pulley to wind and unwind the ribbon at a predefined rate to provide motion assistance. The actuator can also include an idler pulley that engages the ribbon and measures the force applied on the idler. The force signal, for example, provided by one or more strain gauges, can be transmitted to an actuator controller to control actuation of the ribbon. Additional sensors can be provided on the hip or other joints of the user to detect motion and control the actuator to provide assistance. For example, flexion of hip can be an indication that the user is starting to move.

In accord with some embodiments of the present concepts, a control system can be provided for one or both legs to control the actuator and receive signals from sensor to detect motion and adjust the actuator forces to coordinate them to the motion, as described above.

In at least some aspects of the present concepts, the soft exosuit 100 is configured to actuate multiple joints. For example, a pulley 224 actuated by actuator 200 is configured to actuate multiple sets of Bowden cables 142 to separately provide assistive forces to different joints (e g, ankle, hip), the joints being operatively associated with sensors 350 to measure joint kinematics and inform the control system of such joint kinematics. Exemplary sensors are disclosed in WO 2013/044226 A2, WO 2012/103073 A2, WO 2012/050938 A2, and U.S. Pat. No. 8,316,719 B2, each of which is hereby incorporated by reference in their entirety. Further, any of the aspects of the present concepts may further integrate other actively controlled materials such as, but not limited to, those disclosed in WO 2011/008934 A2 or WO 2013/033669 A2, each of which is hereby incorporated by reference in their entirety. By way of example, soft exosuits in accord with any of the disclosed aspects may comprise hyperelastic strain sensors located, by way of example, at any one or more of the ankle, knee and hip (i.e., attached to both sides of each respective joint), to measure human biological joint rotations in the saggital plane. The resulting soft exosuit is very lightweight, cost-effective and easy to don and doff.

This soft exosuit is, in at least some aspects, formed from a combination of elastic and inextensible fabrics or material capable of applying forces across joints in the lower limbs. Forces are created by contracting a cable or other tensile element with a first end fixed to the suit above the joint and a second end fixed below the joint. As described herein, the contracting cable or other tensile element transmits forces through the soft exosuit's inextensible members to the various anchor points to carry the loading. So configured, the soft exosuit allows for multiple joints to be acted upon simultaneously. Advantageously, the soft exosuit comprises a sensor system configured to measure joint angles of the one or more joints and, desirably, three joints (hip, knee, ankle) It is to be understood that although examples herein are directed particularly to impulses applied to a user's legs during activities such as walking or running, the present concepts include motions other than walking or running, and limbs other than the legs (e.g., the arms). In at least some aspects, a multi-pulley and a drive box provides assistance for arm movements. For example, a multi joint actuation capability is provided by a single drive unit configured to activate 1-N pulleys (where N is an integer), the drive unit comprising a single input (e.g., shaft) adapted to drive, directly or indirectly (e.g., through one or more gears), a plurality of pulleys. For joints such as hip flexion and ankle flexion, which operate in tandem, the two pulleys could be active at the same time. Activating two or more pulleys could be done via a permanent connection between the pulleys or a selector which would engage one or more pulleys simultaneously.

Figure 12:
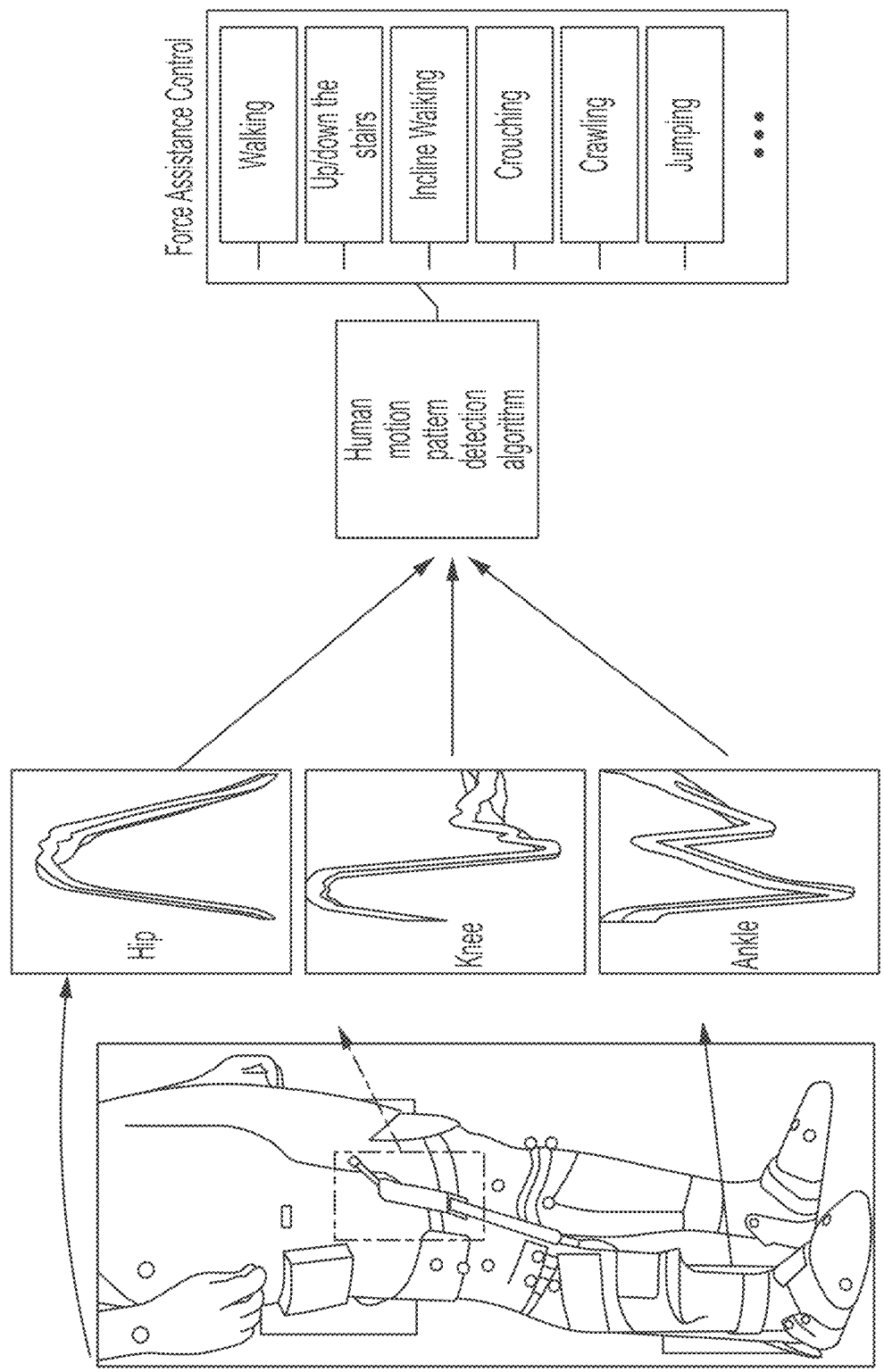
FIG. 12 shows aspects of a control scheme for a soft exosuit in accord with at least some aspects of the present concepts.
Figure 13:
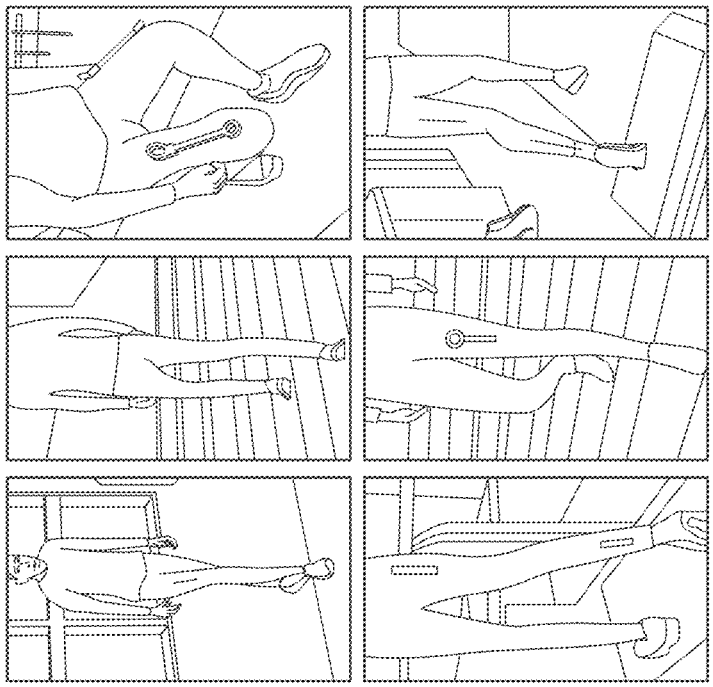
FIG. 13 shows aspects of a control scheme for a soft exosuit in accord with at least some aspects of the present concepts.
Figure 13:
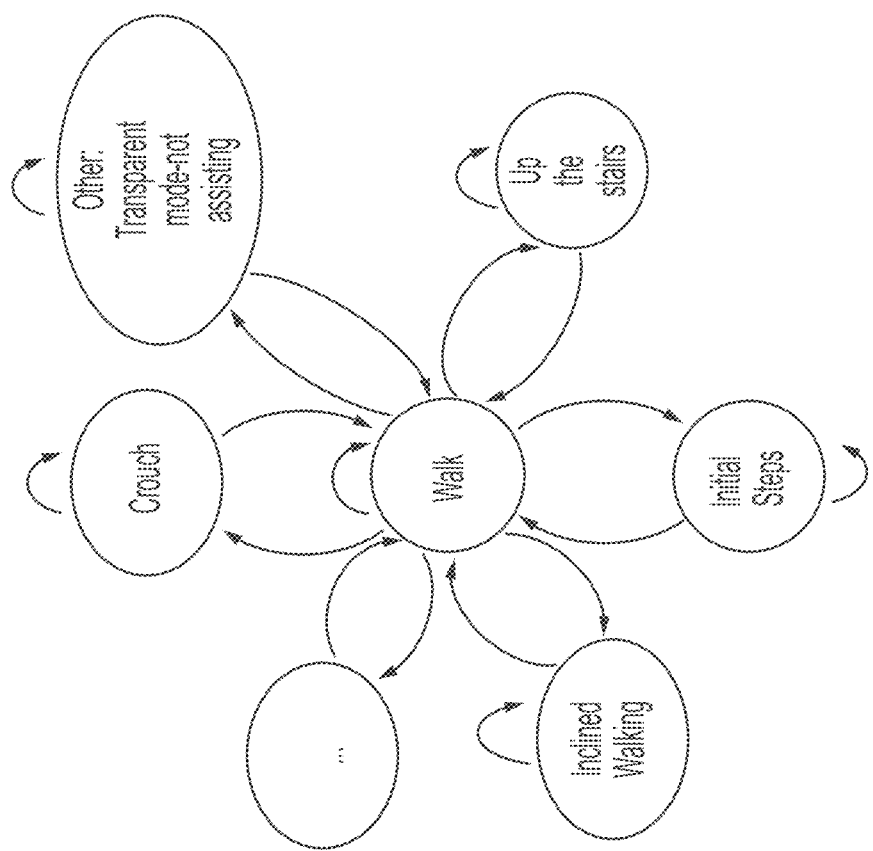
Figure 14:
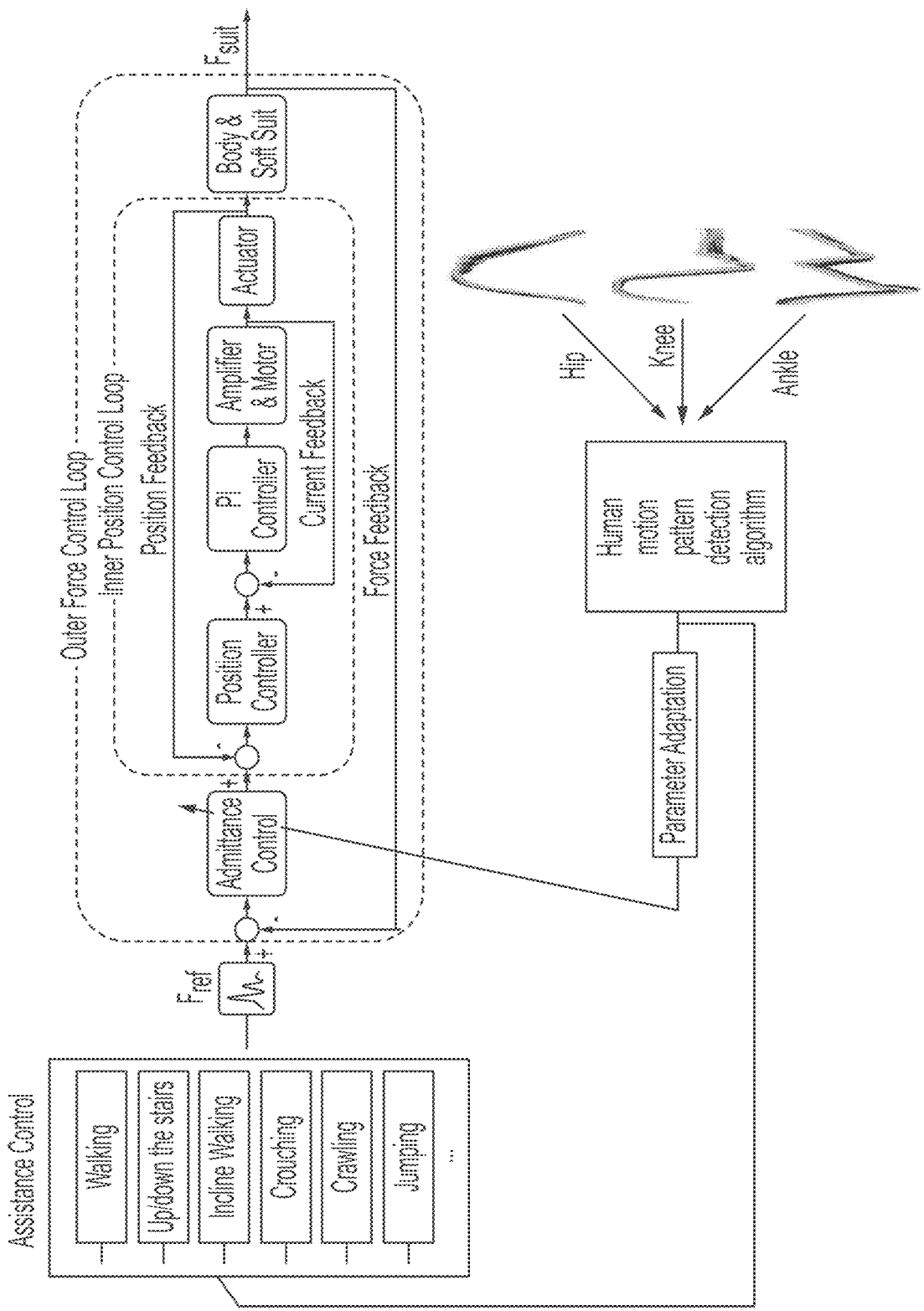
FIG. 14 shows aspects a control scheme for a soft exosuit in accord with at least some aspects of the present concepts.

FIGS. 12-14 show various aspects of control schemes that may be implemented for a soft exosuit in accord with at least some aspects of the present concepts. Such control schemes are flexible and can be adapted as desired for a particular suit and application. By way of example, the soft exosuit 100 of FIG. 12 comprises a plurality of hyperelastic strain-sensors (such as disclosed in WO 2013/044226 A2) to measure suit stiffness and pressure. By way of example, such hyperelastic strain-sensors may comprise a stretchable silicone rubber (e.g., EcoFlex 0030, SmoothOn; PDMS, Dow Corning) sheet embedded with conductive liquid microchannels of non-toxic eutectic gallium-indium (eGaIn), wherein deformation of the channels causes a change in electrical resistance corresponding to the change in length (which in turn can be related to the rotation of the joint). As shown, hyperelastic strain-sensors are disposed across the ankle, knee and hip to measure changes in angle of the monitored joints. The hyperelastic strain sensors can be disposed in parallel with the force-path of the active suit in order to measure real-time suit deformations, such as shown in FIG. 12.

The control system is able to relate, via a human motion pattern detection algorithm or look-up table, the sensed movements of the joints (e.g., looking only at absolute changes in angle, looking at changes in angle in relation to time, velocity and/or acceleration, etc.) to one of a plurality of predicated activities such as walking on a level surface, walking on an incline, walking on a decline, running on a level surface, running on an incline, running on a decline, walking up stairs, walking down stairs, crouching, crawling, jumping, limping, favoring one limb over the other, etcetera. Based on this motion data, the control system may (1) store the data on a local physical storage media, (2) wirelessly transmit the data to another local or remote device via an on-board communication system, (3) transmit the data, through a wired connection (e.g., communication cable), to another local or remote device, device via an on-board communication system and/or (4) use the data to provide real-time force assistance control to adapt the suit seamlessly to the wearer's state of activity and environment. For example, if the soft exosuit measured joint deformations are above a threshold defined based on comfort (e.g., user preference) and/or suit mechanical capabilities considerations, the control system may be configured to automatically decrease assistance level until these deformations are again within a desired operational region. Additionally, the soft exosuit may be used in combination with an active, wearable exoskeleton. In such implementations, the measurement data can be transmitted wirelessly or through a wired connection to a controller of the exoskeleton to thereby cause the exoskeleton to adapt the level of assistance. Moreover, the soft, hyperelastic sensors can be used to measure pressure in relation to any point of interface between the wearer and the soft exosuit, which can be used for online adaptation of the assistance level based on comfort considerations.

Additional control schemes can be used with the soft exosuit if a force sensor is used to measure tension in the cable (e.g., an in-line sensor). The soft exosuit creates tension passively due to the biomechanics of walking. For a given leg, this tension occurs starting around 15-35% of the gait cycle, depending on how the soft exosuit is adjusted, and rises as the leg pushes off from the ground. This rising force can be used as an input to the control system, giving information about when and/or how (e.g., force profile, force timing, etc.) the soft exosuit should be actuated.

Figure 18:
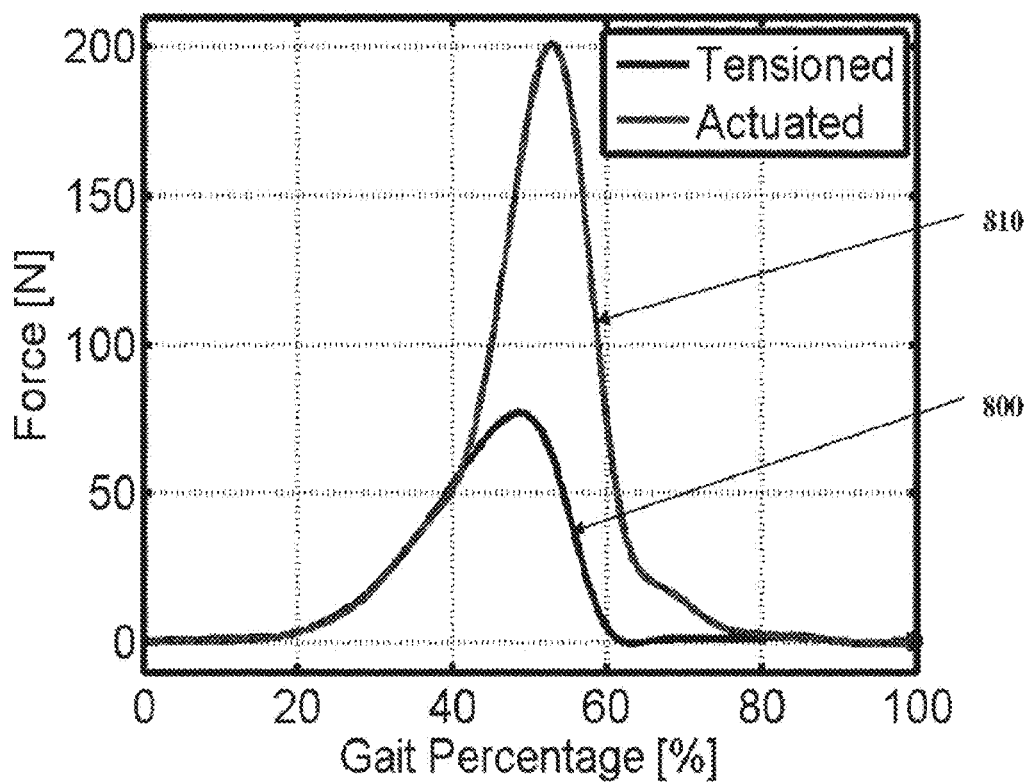
FIG. 18 shows a graph depicting the timing of actuation of the soft exosuit during a gait cycle and the corresponding suit force in relation to cable position.
Figure 19:
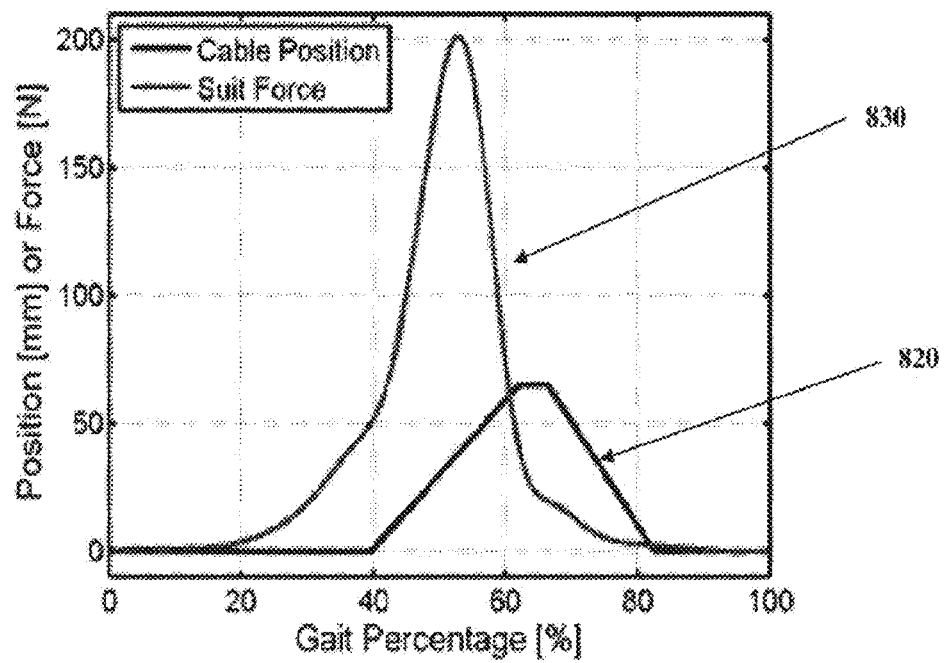
FIG. 19 shows another graph depicting the timing of actuation of the soft exosuit during a gait cycle and the corresponding suit force in relation to cable position.

One control scheme from this information involves, first, tensioning the suit to the point where, during level-ground walking, the peak forces are at a certain threshold magnitude (e.g., $F_{peak}$). Once the suit is pre-tensioned in this manner, the force on the cable is monitored and can be used to predict where in a gait cycle the user is, or is about to be, since the force on the cable predictably crosses the threshold at the same point of the gait cycle. With respect thereto, FIG. 18 shows a graph depicting the timing of actuation of the soft exosuit 100 during a gait cycle and the corresponding suit force under two conditions: when the suit is tensioned 800 and when the suit is actuated 810. The tensioned graph 800 means that the suit has been set to a certain length, and then the length is held fixed throughout the gait cycle. The actuated graph 810 means that the tension in the suit is changed by pulling it together with a Bowden cable, or the like, at the ankle. In graph 800, the tension in the suit changes throughout the gait cycle due to the different motions of the joints (as in FIG. 9D). FIG. 19 shows, for the actuated case 810, the relative timing of the cable position and the suit force and more particularly a graph depicting the timing of actuation of the soft exosuit during a gait cycle (as a percentage of gait cycle) and the corresponding suit force (graph 830) in relation to cable position (graph 820).

In the graph of FIG. 18, the tensioned force crosses 50 N at 40% in the walking cycle, which is repeatable across many steps. This force occurs before actuation begins each cycle, and thus this information can be gained regardless of if the cable is actuated or not. Thus, for the example of FIG. 18, where the control system measures a force in the actuating cable that approaches (or optionally equals or exceeds) a threshold force $F_{thresh}$, the control system is able to utilize this information of the wearer's position in the gait cycle to take one or more actions (e.g., actuate immediately or after a delay). For example, the controller can get an estimate of the person's gait period by looking at the elapsed time between when the force crosses the threshold on two successive steps, or on several successive steps and then taking an average.

Further, from this information on the threshold cable force magnitude and/or flag indicative of crossing a threshold force magnitude, the controller also knows where the person is in their gait at that time. For example, the controller could be set to start a position-controlled pull on the cable at 40% in the gait cycle. In this case, whenever the controller detected that the force crossed the threshold that corresponded to 40% in the gait cycle, the controller could initiate the pull immediately. Or, if the controller was supposed to start a position-controlled pull at 43% in the gait cycle, then the controller would use the gait period to compute the delay between 40% in the gait cycle and 43% in the gait cycle and predictively initiate the pull only after lapse of that computer delay.

Further, to get a more accurate assessment of where the person is in their gait cycle, the controller could also monitor the tension force over time and look at several points where it crosses different force thresholds. In general, the pattern of force versus time will change depending on the person's walking speed. The slope of the force-versus-time curve can also be used to estimate the person's walking speed (or gait period). The slope should also be used in predicting where the person is in the gait cycle since the peak tension force is also a function of the person's walking speed, where the tension decreases as walking speed increases. In summary, a controller can be configured to made that estimates (Current % InGait,GaitPeriod)=$f$(CableForce($t$), CableForce($t-1$), . . . ,CableForce($t-N$))

where f( ) is a function and N is the number of samples used to track the cable force over time. N can be as small as 1 (using two samples to estimate the slope) or as large as 100-1000, depending on the sample rate of the force sensor. To get a good estimate of the slope, forces should be examined for the period of around 5-10% of the gait period. That is, if our gait period is 1 second, then to estimate the slope, the controller should use samples from the current time back to 0.05 or 0.1 seconds prior to the current time.

Yet further, instead of having the cable (e.g., Bowden cable 142) or cables (e.g., for a multi joint activated soft exosuit) pull in (and release) with a position profile (% of gait), there are other control options. The motor could pull in with some specified velocity until a certain peak force is reached. The motor could also pull such that the force at the ankle follows some prescribed force trajectory. The motor could also pull in with some specified velocity until it detects force decreasing due to the biomechanics of walking. Similarly to how the tension increases in the soft exosuit and cable at 15-35% in the gait cycle due to the biomechanics of walking and the soft exosuit changing length, the tension in the soft exosuit and cable will also decrease at around 60-65% in the gait cycle due to the configuration of the body causing the soft exosuit to slacken. In particular, the ankle lifting up at around 60-65% of the gait cycle and the knee bending cause the soft exosuit to become slack even if the cable is held at a fixed length or is being pulled by the motor (and decreasing in length) at moderate or slow rates. This decrease in force due to the biomechanics can be used as a trigger for when the cable should be released and fed out again. At that point, the cable should be released at some specified velocity or following a certain force trajectory back to the nominal tensioned point.

In general, the process of tensioning and releasing the cable(s) can be done following a force trajectory, position trajectory, velocity trajectory, some combination of these, or some other scheme.

As noted above, real-time measurements of human biological joint angles using wearable strain sensors (e.g., hyperelastic strain sensors comprising liquid metal conductors, conductive fibers integrated with nonconductive stretchable fabric, etc.) or other type(s) of sensors (e.g., inertial systems, angular velocities measured from a plurality of gyroscopes/accelerometers attached on different limb portions, etc.) can be used to inform the control system of the soft exosuit and/or of assistive exoskeletons when performing daily-life or field tasks, such as represented in FIG. 13. The information provided by these strain sensors (or other sensors providing positional data or derivatives thereof) can be used to classify different human motions such as walking, going up or down the stairs, incline walking, crouching, crawling, stopping, jumping, etcetera, once suitable baselines are established either for the wearer or for a population similar to the wearer (e.g., anatomically similar). Real-time analysis of human motion is of vital importance when a person is wearing a wearable exoskeleton or assistive devices in real-world applications (i.e., out-of-lab). The assistance required to perform these various activities totally differs and a strategy that works well for walking won't benefit the user or may even destabilize the user's motion when the user performs variations of the same task (incline walking) or performs other movements. In accord with at least some aspects of the present concepts, sensors integrated into the soft exosuit (e.g., strain sensors, pressure sensors, gyroscopic sensors, accelerometers, etc.) are used to measure one or more joint rotations or limb motions (e.g., rotation of the hip, knee and/or ankle), or are used to permit determination of one or more joint rotations or limb motions, and this information is compared to reference data for the wearer of the soft exosuit (e.g., wearer baseline data) or for a population having similar characteristics (e.g., look-up tables, algorithms, etc.) to determine kinematics and/or other characteristics of motion. The determined motion(s) can then be used by the soft exosuit control system to affect on-board systems (e.g., actuation times and/or magnitudes for a single joint type, actuation times and/or magnitudes for a plurality of joint types, etc.) or to communicate with and/or effect local or remote external systems (e.g., worn exoskeleton). Thus, the obtained classification of human motion(s) can be used to define a state-machine that updates in real-time to inform the control system as to what motion(s) the wearer is performing.

Further, where a plurality of soft exosuits are deployed amongst a plurality of users (e.g., a squad of soldiers), motion data from the plurality of soft exosuits are communicated, in real-time, to one or more local or remote external systems and the motion data analyzed (either singly or in combination with other measured data, such as position data for each wearer, respiration, heartrate, etc.), in the aggregate to determine the motions of the group and characteristics of such motion, infer causes for deviations from expected values, and initiate corrective actions or engage other local or remote systems deemed appropriate responsive to such characteristics of motion. By way of example, if a squad of soldiers is expected to be walking along a road, and GPS data for the soldiers shows the soldiers moving to opposing sides of the road, GPS data alone doesn't indicate whether the soldiers are taking cover in ditches or simply allowing a vehicle to pass. However, if the same GPS data is combined with information that showed rapid movement of each of the soldiers combined with an assumed prone or semi-prone position, such information transmitted in real-time to a remote control system could automatically initiate an alert that the squad has possibly been engaged by hostiles and data on nearby assets could automatically be routed to appropriate decision makers remotely or in the field. Thus, the soft exosuit sensor data is not only utilizable by a soft exosuit control system for an individual user, but can be used by external (command and) control systems, which may utilize as control inputs data from a single channel (e.g., one soft exosuit) or multiple channels (e.g., a plurality of soft exosuits).

In accord with the aforementioned use of sensor data, such sensor data can also be used to provide to the soft exosuit control system information about the user's gait, such as gait phase, speed and amplitude. These parameters will allow the force profiles delivered to the user biological joints during walking by actuator(s) 200 to be adapted in real-time, resulting in an increased efficiency of the assistance. By way of example, such utilization of sensor data can permit elimination of other sensors, such as the aforementioned foot switch sensors, which would be rendered unnecessary.

FIG. 14 shows an example of one exemplary advanced control architecture adapted to change soft exosuit assistance based on detected soft exosuit wearer motions. Since the assistive forces required by each joint while performing different motions are completely different, a control system should be configured to provide adequate assistive forces to the user during the different considered activities. In FIG. 14, a human motion pattern recognition algorithm output, such as was generally described above in relation to FIGS. 68-69, informs the control system to determine the reference trajectory forces to be delivered to the user. Humans adapt the biological impedance of their limbs when performing different motions, such as walking in an inclined terrain, running, etcetera. Implementing a position-based admittance control with force as an input ($F_{Ref}$) allows defining the virtual impedance (inertia, damping and stiffness) felt by the user during actuation ($F_{suit}$), provided that the inner position control loop compensates the dynamic and friction components. The use of on-board soft exosuit sensors thus permits utilization of sensed motions in combination with an admittance control architecture to adapt the soft exosuit to work with the user based on the movements of the user, as shown in FIG. 14, providing more natural and efficient actuation. The human motion pattern recognition would be used to change the assistance force of an active exoskeleton and to change the virtual impedance delivered to the user.

Figure 16:
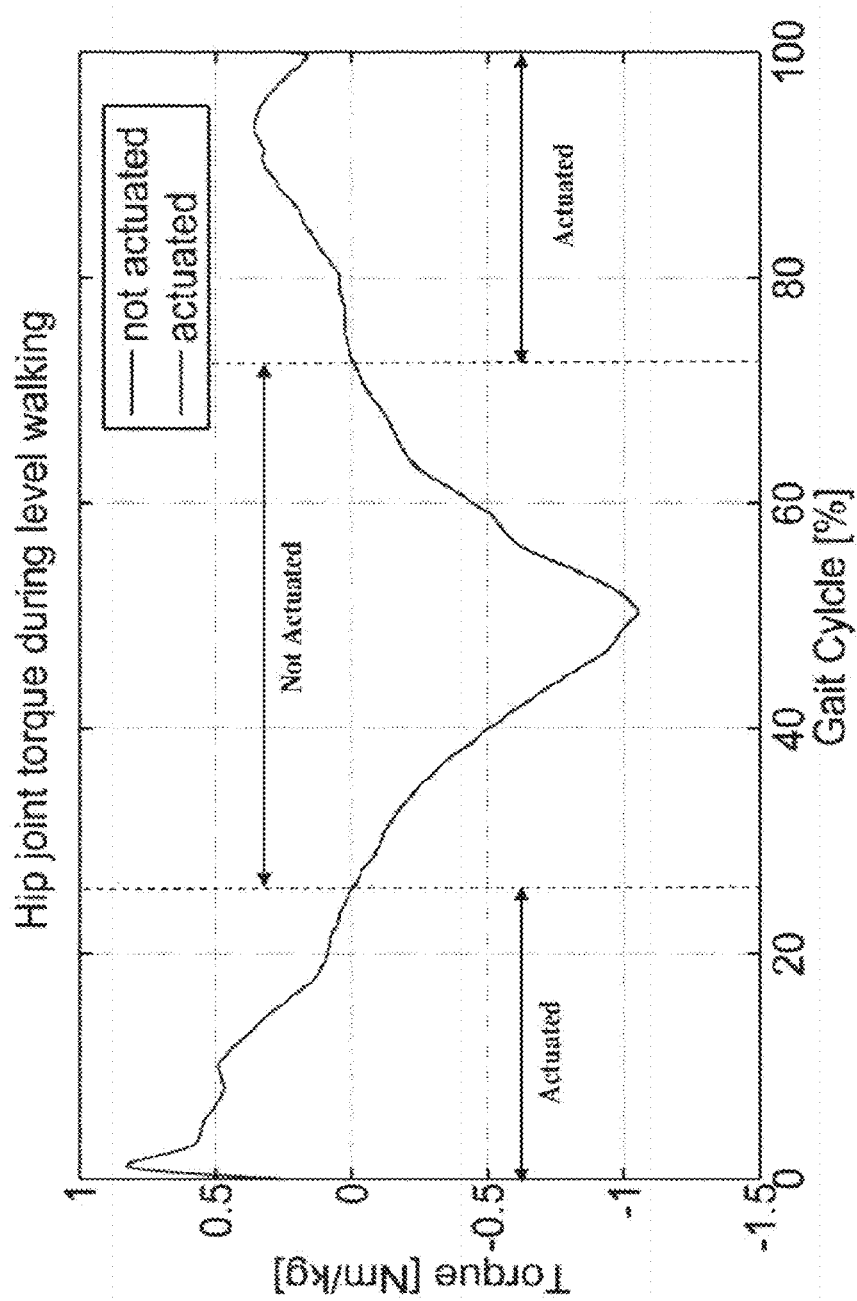
FIG. 16 shows hip joint torque vs. gait cycle percent during level walking.

Returning to the soft exosuit 100, and particularly to a system built to assist hip extension both during normal and walking uphill/downhill (see, e.g., soft exosuit of FIGS. 15A-15B), FIG. 16 shows hip joint torque during level walking where the soft exosuit is actuating between about 0% to about 25% of the gait cycle, not actuating between about 25% to about 75% of the gait cycle, and again actuating between about 75% to about 100% of the gait cycle. The positive torque corresponds to hip extension (portion of curve associated with actuation) whereas the negative torque corresponds to hip flexion (portion of curve associated with no actuation). Two control schemes are useful in providing such assistance, position-based control and force based and admittance control.

As to position-based control, during normal gait, hip extension starts before heel strike occurs. A position-based control scheme needs to take such characteristic into consideration. In order to get information about the step frequency during normal gait, foot switches are used to detect the heel strikes. The time for one step is measured by subtracting the time for the last heel strike from the time of the previous one. This information is then stored in a buffer which consequently comprises the step frequency. By averaging the step data saved in the buffer, or data derived therefrom, the next heel strike can be predicted by adding that specific time to the last heel strike event. In that context, position control means that a fixed trajectory is replayed if the system time reaches the predicted time for the next heel strike. In order to adapt the position controller to different speeds, the fixed trajectory is time scaled, meaning that the peak of the trajectory never changes but the time the motor reaches that maximum can change depending on the measured step frequency.

Figure 17:
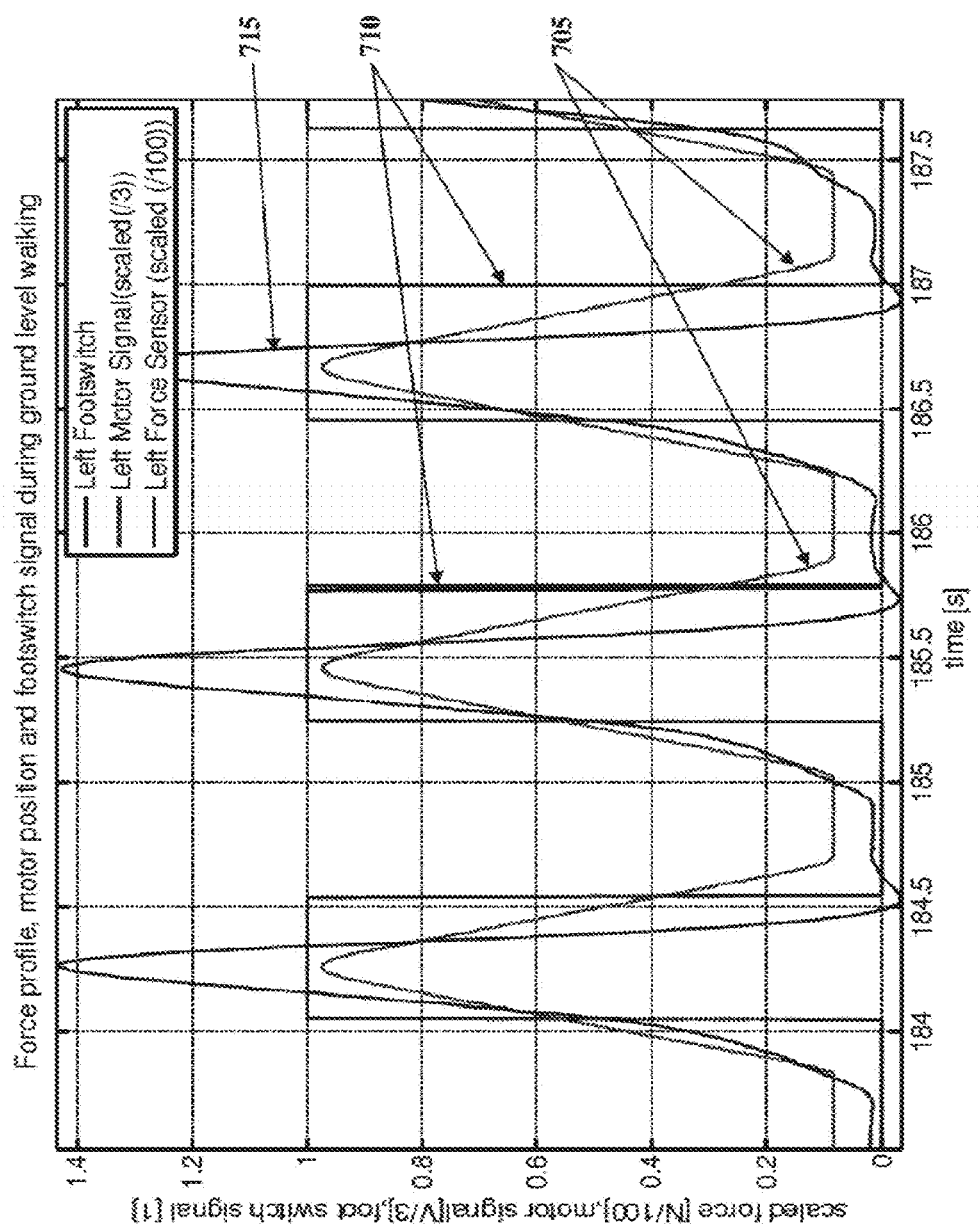
FIG. 17 shows profile, motor position and footswitch signal during ground level walking.

FIG. 17 shows an extract of recorded data during ground level walking depicting curves for force profile, motor position and footswitch signal. It can be seen from curve 705 that the motor starts spinning before heel strike occurs, shown by curve 710. By playing back the scaled motor trajectory, a corresponding force is generated, as shown by curve 715. It is to be noted that the force is the force in the cable and not the actual hip moment. The main disadvantage of such position-based control is that the system needs to be at least slightly pretensioned to permit the trajectory to be played back to apply the desired forces. Otherwise, the system would mainly wind up slack cable, resulting in low applied forces.

As to force based and admittance control, force based control can advantageously be used to track hip motion. By always having a slight (<5N) tension in the cable, the controller is able to follow the hip motion, which eliminates the main disadvantage of the position based controller. Since the position based control showed good results for the applied moment and for assisting the user, admittance control is chosen as an advanced controller for the system. The motor is still position controlled, which shapes the inner control loop. By developing an efficient position controller, the physical system properties like inertia and friction can be neglected. By adding an outer admittance control loop, the system behavior can be simulated and shaped to the physical system accordingly. The controller set point, the desired value, and the error are now forces in that specific case.

In order to follow the correct torque profile for hip extension (see FIG. 16), foot switches are used to synchronize the controller in the first place. The exact same principle is used as for the position controller. Tracking the hip motion by using the admittance controller enables the system to work without foot switches as well. Foot switches can only provide the time a heel strike occurs. Similar information can be obtained by reading the motor encoder and marking the point where extension changes into flexion. By knowing that specific point, the same principle can be applied as for using footswitches. As mentioned, the motor encoder signal is used to estimate the hip angle. Although, it is not necessary to know the exact angle since the only information needed to synchronize the controller with gait is the change between extension and flexion.

In view of at least the above, various non-limiting control strategies to optimize the power delivered to the human biological joints when performing different activities are discussed below and with reference to FIGS. 20A-34B.

Through human subject experiments, the inventors have evaluated the performance of different assistive strategies in terms of power delivered to the wearer by the soft exosuit actuator(s). Traditionally, assistive strategies are predefined, and adapt only as a function of gait percentage, so they are scaled to the specific gait speed and cadence. While this guarantees some degree of adaptation, it does not ensure an optimal delivery of positive power from the device to the wearer.

Indeed, such methods do not account for the physiological step-to-step variability, and, due to inexact timing, can result in less positive power delivered to the wearer, and in a reduction of negative power absorption by biological structures.

In at least some aspects of a soft exosuit control system in accord with the present concepts, joint angular velocity and acceleration are measured by one or more sensors. The soft exosuit control system estimates, in real-time, when an applied force will result in a boost of positive power to the wearer's biological joints and use this information to both trigger application of a requisite force and to adaptively modify the applied force to change a commanded force profile as needed. This on-line computation ensures that only positive power is delivered at the right moment during the gait cycle. It also ensures that step-to-step variability is entirely accounted for.

Figure 20B:
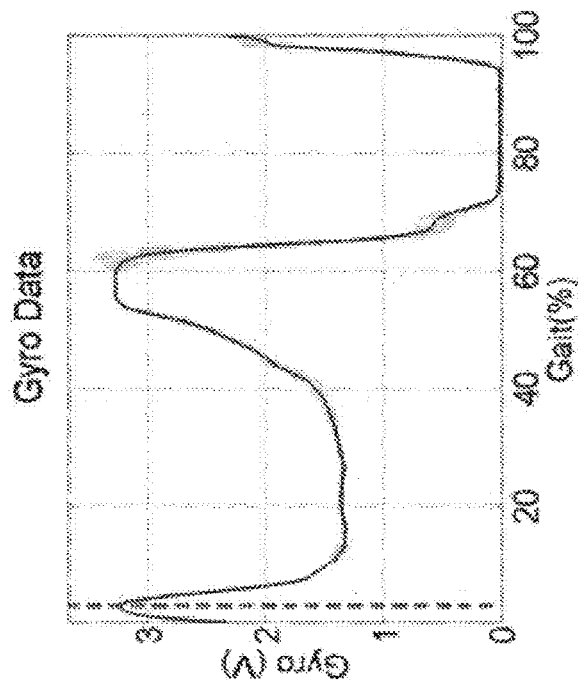
FIGS. 20A-20B respectively show an example of a gyro attached to a footwear attachment of a soft exosuit according to at least some aspects of the present concepts and a graph of velocity data obtained by the gyro in relation to a percentage of the wearer's gait cycle.
Figure 20A:
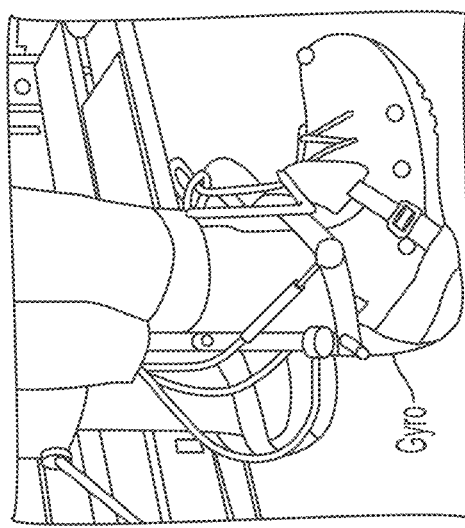

FIG. 20A shows an example of a control system utilizing a gyroscope attached to a user's footwear (e.g., attached to a boot, as shown). FIG. 20B shows a plot of the Gyro velocity (V) as a function of Gait (%). The output signal from the gyroscope is used by the control system to estimate angular velocity of the limb and to determine when the joint speed is positive. When the joint speed is determined to be positive, or at a point in time at which the control system predicts the joint speed will be positive, the control system instructs the soft exosuit actuator(s) 200 to initiate delivery of positive forces to the joint that will result in a boost of power to the joint.

Since human walking kinematics and kinetics vary slightly from user to user when delivering actuation and under different loadings (e.g., carrying different weight in a backpack as shown in FIG. 2B), the inventors sought to determine optimal assistive trajectories, based on real-time estimation of power, to provide resulting systems and methods better suited to a variety of different subjects, activities and operating conditions.

Figure 21B:
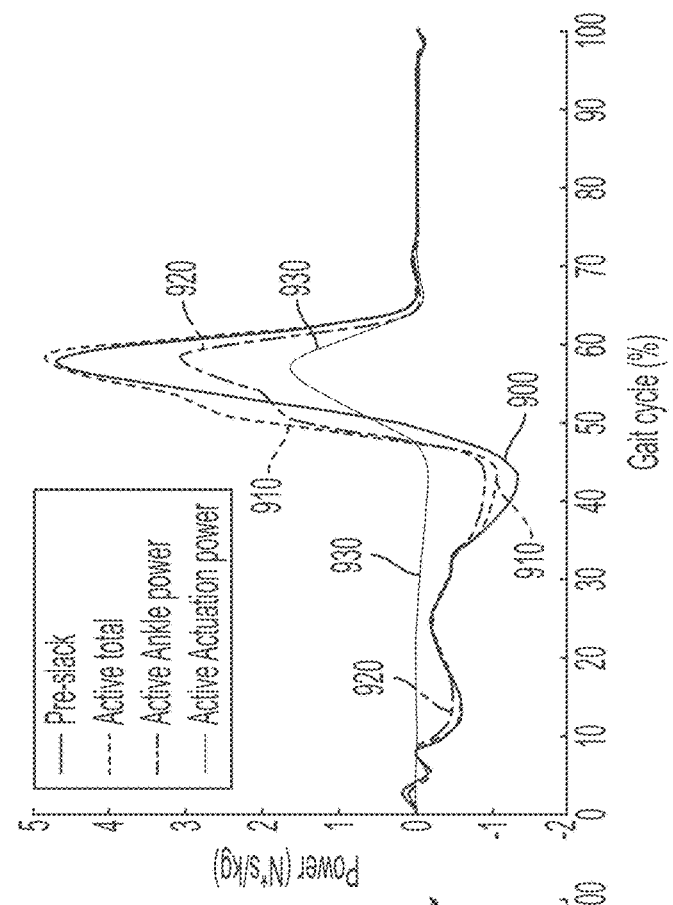
FIGS. 21A-21B show power calculations for different components of a soft exosuit in accord with at least some aspects of the present concepts.
Figure 21A:
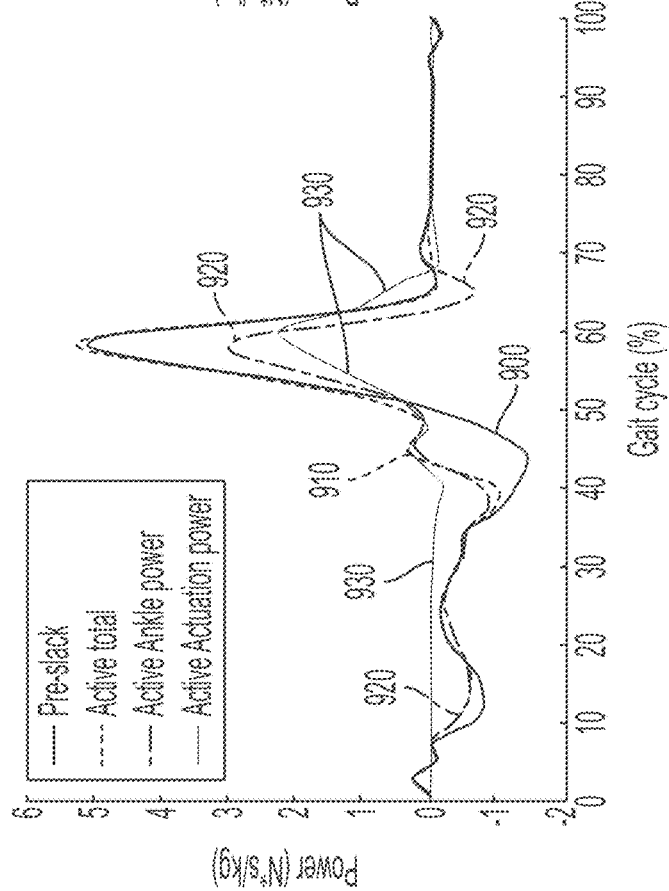

FIGS. 21A-21B show power calculations for the gyroscope embodiment shown in FIG. 20A and gyroscope data represented generally in FIG. 20B. Dashed black lines 900 indicate the power absorbed/produced by the biological joint when the wearer of the soft exosuit 100 is walking without assistance from the soft exosuit. Lines 910 indicate the power absorbed/produced by the combination of the biological joint and the active soft exosuit when the wearer of the soft exosuit is walking with assistance from the soft exosuit. Lines 920 indicate the power absorbed/produced by the biological joint with assistance and lines 930 indicate the power delivered by the active soft exosuit to the joint.

As shown in FIG. 21A, the actuation trajectory results in a reduction of the negative power absorbed by the biological joint (active ankle power) compared to normal walking (Pre-slack), therefore reducing the efficiency of the biological structure. As shown in FIG. 21B, a more optimal actuation trajectory results in a preserved negative energy part (active ankle power) compared to normal walking (Pre-slack) as well as a decreased positive power required when walking Overall, the second actuation trajectory depicted in FIG. 21B is more optimal as it reduced the overall energy cost for one gait cycle.

Figure 22A:
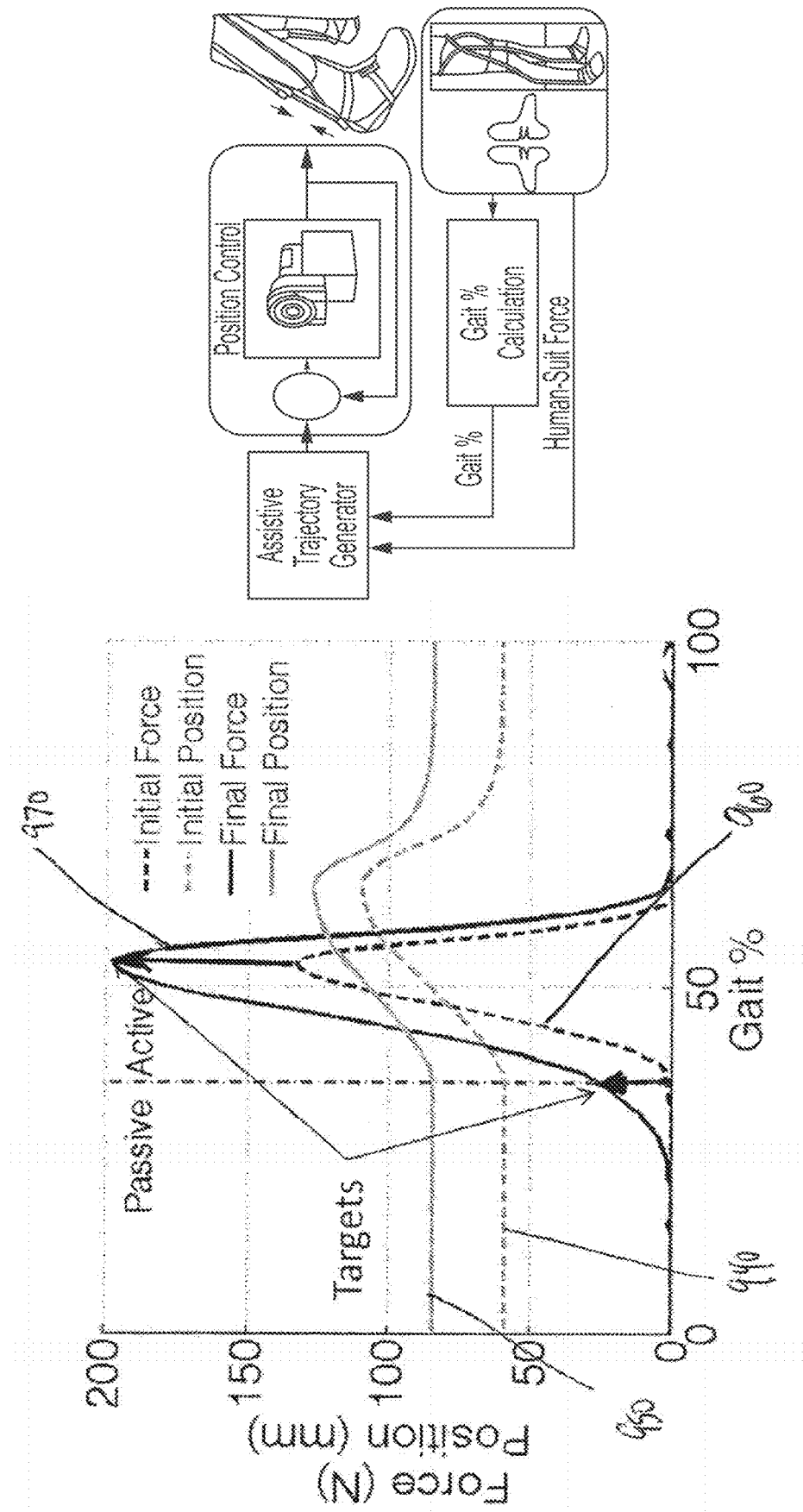
FIG. 22A shows plots of Force (N) and Position (mm) as a function of Gait (%) for a control system in accord with at least some aspects of the present concepts, which is represented in FIG. 22B, which uses gait timing in combination with an Assistive Trajectory Generator, Position Control, and Human Suit-Force Monitoring.
Figure 22B:
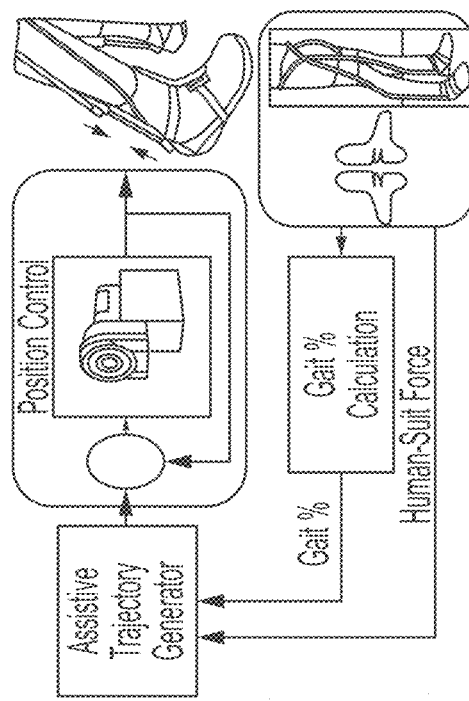

Unlike conventional rigid exoskeletons, the soft exosuit is flexible and has the potential to deform or move over time as the wearer engages in one or more activities (e.g., walking) This presents a problem when the soft exosuit is controlled using a position control scheme since the assistive profiles resulting from this position controller will be correspondingly modified over time and for different motions. By monitoring key features of the force profile, including the peak force and the passively generated force before actuation, the assistive position profile can be automatically adjusted to keep the force consistent over time and for different motions. FIG. 22A shows an example wherein a target pre-tension of 30N is desired, with a peak cable force of 200N to be applied to the heel. Line 940 represents an initial position of the soft exosuit relative to the wearer and line 960 represents an initial force for the initial position of the soft exosuit. The initial force is applied starting just before about 40% of the gait cycle. Through feedback from continuous monitoring of the human-suit interaction force (FIG. 22B), the trajectory is modified by increasing the baseline position and its peak (Line 950). Line 970 represents a final force for the position of the soft exosuit in the modified or final position of the soft exosuit relative to the wearer. The upward arrows from the initial force (line 960) to the final force (line 970) represents the modification of the applied force from the initial force to the final force to account for the differential movement of the soft exosuit in accord with the control scheme represented in FIG. 22B. The final force is applied starting just after about 20% of the gait cycle. The assistive profile is also advantageously modified based on detection of different motions (walking, jumping, etc.) of the wearer of the soft exosuit.

Figure 23A:
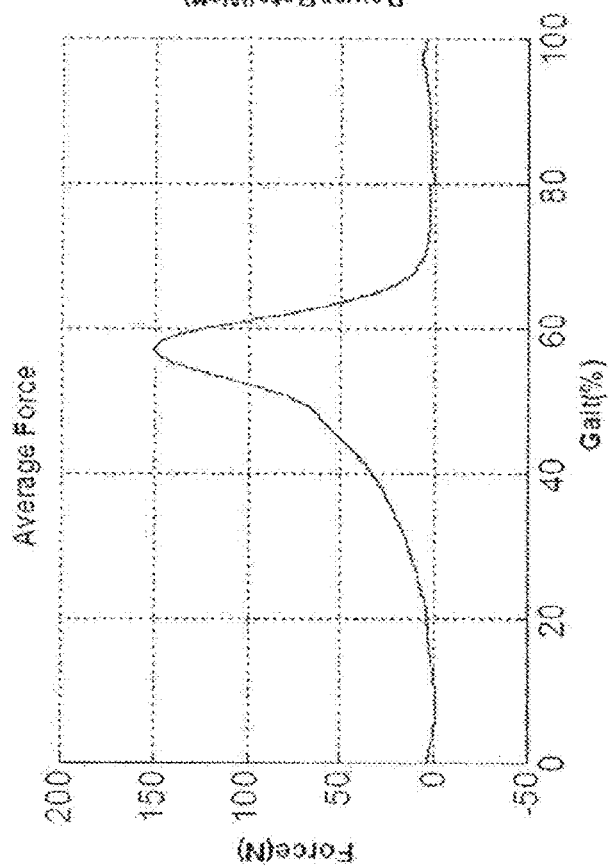
FIG. 23A shows Force (N) as a function of Gait (%), within one standard deviation, for an average ankle actuation profile with a soft exosuit 150N desired peak force.
Figure 23B:
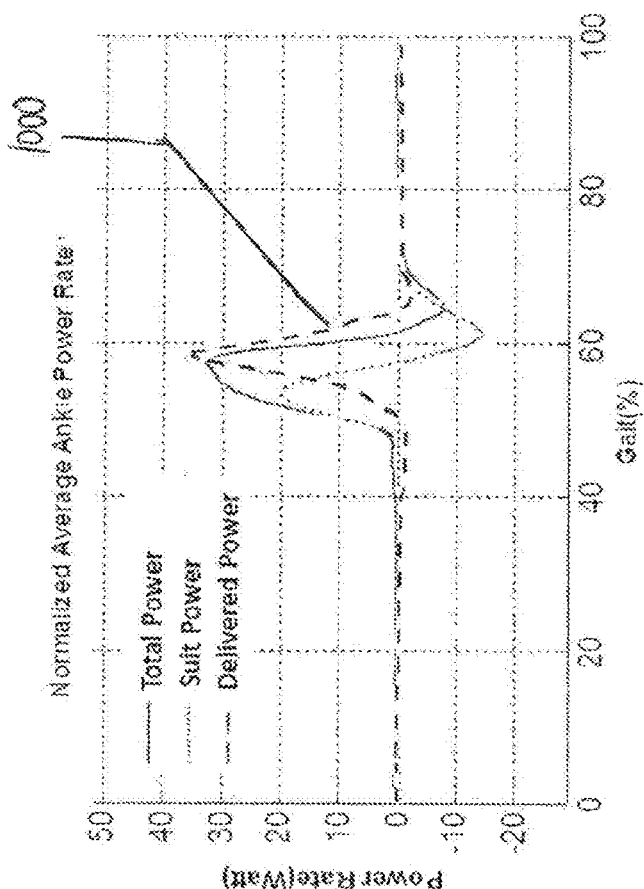
FIG. 23B shows normalized average ankle power (Watt) as a function of Gait (%), within one standard deviation, in accord with at least some aspects of the present concepts.

FIGS. 23A-23B show graphs relating to a soft exosuit force-based position control utilizing information from a soft exosuit-integrated gyroscope, such as is shown by way of example in FIG. 20A. By measuring joint angular velocity with a gyroscope, the control system is able to estimate, in real-time, when an applied force (e.g., to a footwear connection element 130, as shown in FIG. 2A) will result in a boost of positive power to the wearer's biological joints and use this information both to trigger and to modify the shape of the commanded force profiles. If the trajectories are applied earlier, this will imply a reduction in the negative power absorbed by the biological structures as was shown in FIGS. 21A-21B.

In order to assist the ankle, a force-based position control triggered by the gyro signal can be implemented. The control system applies a pre-tensioning force to the soft exosuit 100 to take advantage of the passive properties of the suit. FIG. 23A shows the average ankle actuation profile, within one standard deviation, during a human subject test experiment with a 150N desired peak force. In the control system shown, the control system was set to reach 25N pretension at 36% of the gait cycle, with the suit tension adapted to increase slowly leading up to the ankle assisting force initiated at 47% of the gait cycle to facilitate both the suit structure and the walking kinematics. At 47% of the gait cycle, the actuator(s) 200 outputs a force trajectory necessary to reach the desired peak force (in this example) of 150N at around 56% of the gait cycle, with a relatively rapid return to the pretension position at 65% of the gait cycle in order to avoid interfering with motion of the limb during the swing phase.

In the control system of FIGS. 23A-23B, the gyro controls the timing of the actuator's pulling, such as via Bowden cable 142, on the targeted limb and joint (e.g., ankle moment). In an example of ankle activation, to achieve pure positive power, the pulling in accord with the algorithm should start with the ankle plantar flexion movements, which can be detected by the gyro attached on the heel of the wearer of the soft exosuit. The advantage of this algorithm can be seen in the power rate plot of FIG. 23B, wherein the delivered power (Watts) of the ankle joint (curve 1000) is almost pure positive for this actuation strategy. FIG. 23B shows the power generated by the exosuit on the cable ("Total Power"). Part of this power is delivered to the joint ("Delivered Power") and part goes or comes from the suit ("Suit Power"). It can be seen that the powered delivered to the ankle ("Delivered Power") is almost always positive throughout the gait cycle, and does not negatively impact the gait by absorbing negative power.

Figures 24A, 24B:
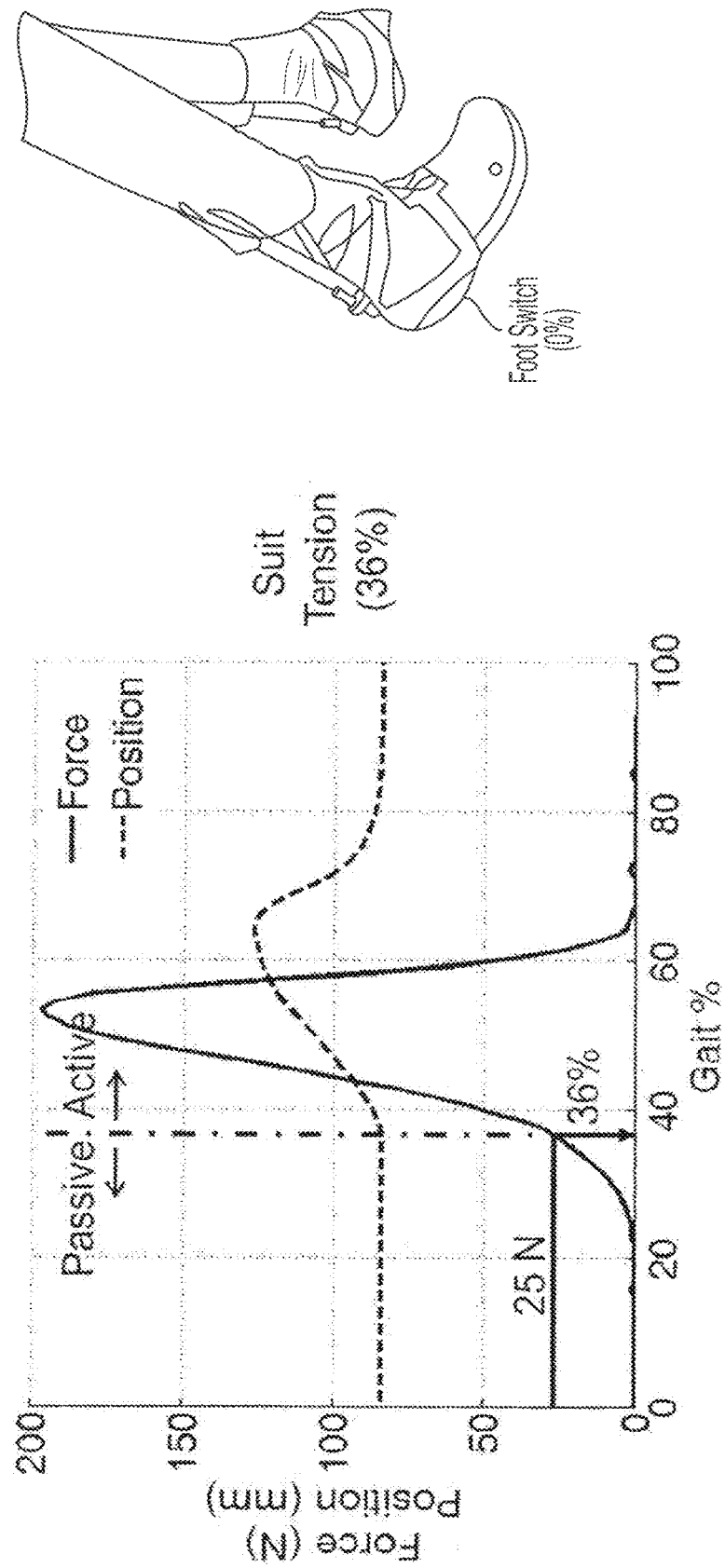
FIGS. 24A-24B show a soft exosuit control system delivering synchronized assistance to gait with no step delay in accord with at least some aspects of the present concepts.

FIGS. 24A-24B show a control method that delivers synchronized assistance to gait with no step delay (zero-step delay control). Wearable systems that assist locomotion typically time their control algorithms by measuring the heel-strike. Therefore, in order to calculate the gait % while walking within the current step, they require an average of the last 3-5 steps. This fact makes transitions between different movements hard (i.e., not smooth) when walking in rough or uneven terrain wherein the user is required to change speeds and/or gait and/or activity (e.g., inclined walking, jump, crouch, etc.).

By taking advantage of the unique properties of the soft exosuit disclosed herein, which can passively assist walking, a control system can deliver synchronized assistance to gait with no step delay (zero-step delay control). In other words, this zero-step delay control does not require information about the previous steps to be able to generate the assistive profiles. In order to ensure smooth transitions, the controller monitors the passively generated human-robot interaction forces, in addition to the heel strike, to get multiple data points within a single gait cycle and use the desired level of pre-tension force (normally from 20 to 50N) to trigger the assistive, active profile.

Between about 30-60% of the gait cycle, which extends from one heel strike to the next for a given leg, the calf muscles and tendons push the body up and forward, and the hip muscles and ligaments swing the leg forward. Initially, the calf and hip absorb power by stretching as the body's center of mass falls downward and forward over the planted foot. After around 50% of the gait cycle, this absorbed power is returned to the body as the tendons and ligaments elastically recoil. The muscles in the calf and hip actively contract to supplement this returned power with additional energy. The soft exosuit 100 absorbs and transmits power in this manner as well: with the actuator actuation member(s) held at a fixed length initially, the soft exosuit material itself stretches and the tissue under the suit compresses as the body falls forward. This induces a tension in the suit and absorbs power from the body. Thus a multi-articular soft exosuit architecture has the unique property in that the soft exosuit only becomes tense when the body is in the correct pose for forces to be applied. Information from the passively generated human-suit interaction forces can be used to deliver the desired assistance.

FIG. 24B shows a foot switch activating at 0% of the gait cycle, with a human-suit force application at 36% of the gait cycle. As shown in FIG. 24A, the activation of the assist occurs at 36% of the gait cycle, prior to which the suit is passively increasing (from about 20% of the gait cycle) tension up to a threshold of about 25N. The assistive profile is shown to start increasing following 36% of the gait cycle, with the force rapidly increasing to a peak of 200N at about 54-55% of the gait cycle and rapidly dropping off thereafter.

The gait % at which the assistance is provided is calculated as follows:

$$\text{Gait } (\%) = \frac{(t - t_{0\%}) \times 36}{(t_{36\%} - t_{0\%})} \quad (1)$$

As an initial consideration, motions such as jumping, crouching, or crawling don't generate the same passive forces and hence don't trigger an assistive profile, keeping the system in a fully-transparent mode and hence not interfere with the wearer.

The control algorithm works as follows:

First, the control system detects a heel strike, via a heel strike sensor or other sensor providing information relating to a heel strike, and waits for the passively generated force to reach a specified threshold (e.g., 25N). Second, the Gait (%) is calculated within the step using Equation (1). Third, the control system triggers the position assistive profile based on Gait (%). Fourth, the control system monitors the pre-tension force at $\text{Gait}_{av}=36\%$ and the peak force value for the step. Fifth, the control system corrects an assistive position profile initial and maximum amplitude to ensure realization of the desired forces (position-based force control method). This control method therefore can deliver a timely, synchronized assistive profile by only detecting heel strike and the passive force threshold event.

Over multiple steps, the amount of assistance, pretension and timing of the pretension event can be updated by updating an average Gait % ($\text{Gait}_{av}$) using heel strike and the average step time for the last N steps.

Accordingly, there is provided a force-based position control with gait percentage estimation and assistance triggering from both sensors (e.g., both foot switches). The controlled position profile is adapted by using the force-based position control to correct the passive pre-tension level and peak forces. The average gait % ($\text{Gait}_{av}$) is calculated using the heel-strike. The maximum position profile adaptation is 1 mm per step, and will be activated only when the user has the right sequence of signals from both foot switches, hence this doesn't affect the achieved force significantly when transitioning between motions or taking random steps. Results show that this control works robustly for different events such as obstacle avoidance, jumping, sudden stops, etc.

Other combinations of sensors are possible to use with zero-step delay control, so long as one sensor reading occurs after 0% in the gait cycle and before 36% in the gait cycle, and the suit tension can be used as the second sensor.

In accord with other aspects of the present concepts, a control system is configured to provide automatic adjustment of a force profile based on suit pressure monitoring. By way of example, sensors can be integrated in a soft exosuit 100 to measure pressure levels at the physical interface between the user and the human in some key areas of the body which support forces. The controller(s) (e.g., processor(s) 250) of the soft exosuit 100 monitor pressure in real-time in one or more different areas, including but not limited to bony areas such as the iliac crest, and adjust the peak force and/or position profile to keep the user-felt pressure within specified limits, which are optionally user-configurable for the user's comfort. Measurement of real-time pressure in one or more key areas of the human to soft exosuit interface can thus be used to ensure comfort.

Figure 25:
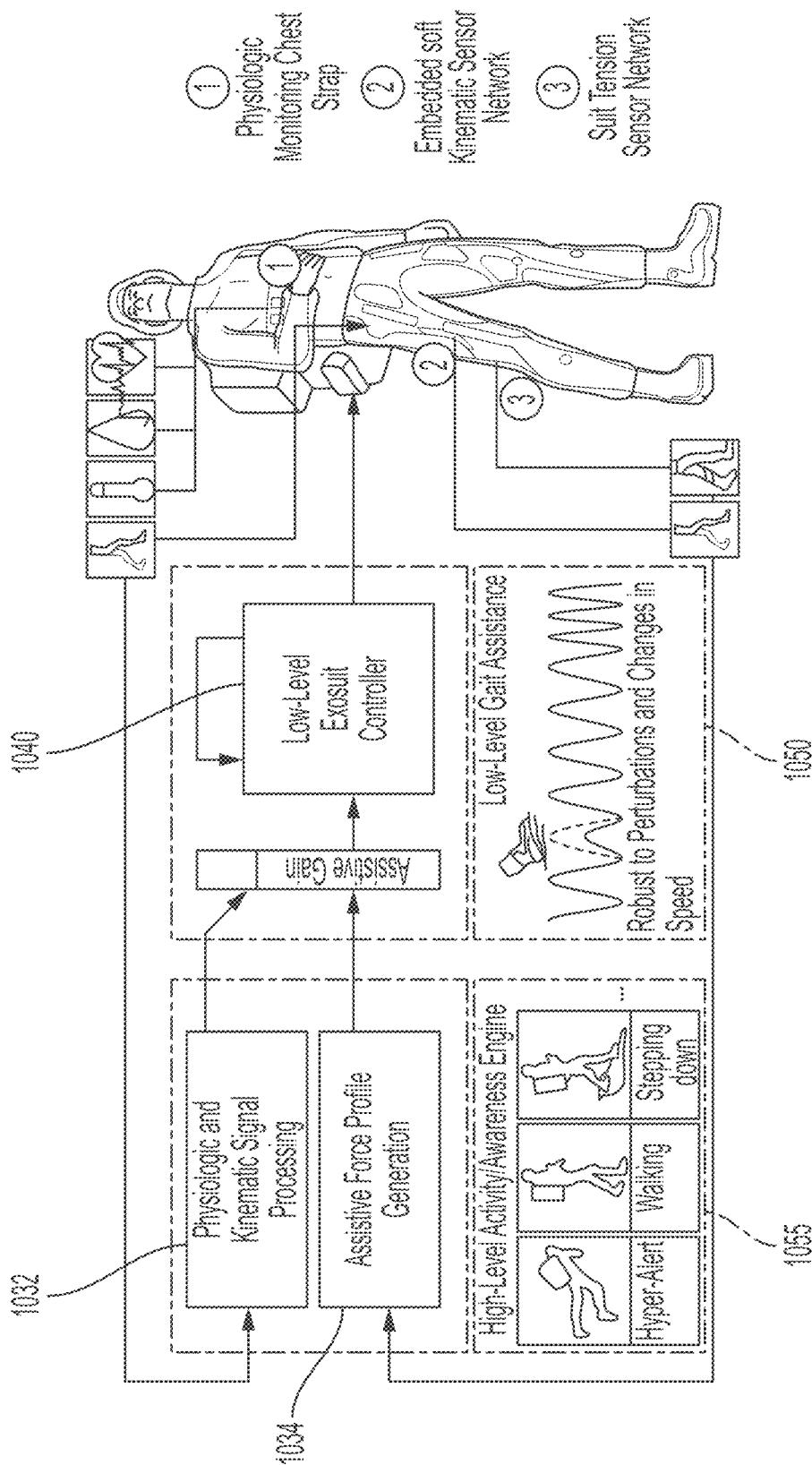
FIG. 25 depicts a multi-layered control architecture for a soft exosuit in accord with at least some aspects of the present concepts.

FIG. 25 shows a control system for the soft exosuit 100, in accord with at least some aspects of the present concepts, configured to adapt to different activities and physiological states of the wearer. In one embodiment, the control system of FIG. 25 utilizes a multi-layered control architecture comprising a low-level gait assistance control (represented by Low-Level Gait Assistance 1050 and Low-Level Exosuit Controller 1040) and a high-level human-awareness engine (represented by High-Level Activity/Awareness Engine 1055, Physiologic and Kinematic Signal Processing 1032, and Assistive Force Profile Generation 1034). The low-level soft exosuit controller 1040 is informed by two key measurements: the suit tension status (provided by the "Suit Tension Sensor Network" (3) in FIG. 25) and gait kinematics (provided by the "Embedded Soft Kinematic Sensor Network" (2) in FIG. 25). The Suit Tension Sensor Network provides a passive, kinematic-based tension information, which in combination with the tension patterns measured at the ankle and hip, enables the detection of gait sub-phases. This can be achieved, for example, by pattern-recognition and machine learning methods that try to find the association between these multiple tension signals, and timing of gait phases. The information from the sensors (1)-(3) of FIG. 25 are advantageously, but not necessarily, processed with data from other redundant sensors, such as inertial measurement units (IMUs) or insole pressure, to ensure robust control (e.g., robust to perturbations and changes in speed).

A multi joint low-level control strategy will provide a reduced parameter set that can be controlled without having to do precise control locally at each joint—rather, control will be optimized across all joints together. This will ensure that the level of assistance to each muscle group is robust to gait cadence, step length, joint angle offset (due to inclined walking), and other joint-level variables. It will ensure a timely delivery of assistance during only the energy-relevant phases of gait for each muscle group (e.g. forward propulsion for the ankle joint during level walking, early stance for hip extension during uphill walking).

A high-level awareness engine 1055 monitors the user's biomechanical and physical stress status by analyzing data from the whole body sensor network. By analyzing the signal patterns, an intelligent activity-adaptation algorithm will dynamically adapt the assistance generated by the low-level controller to different gaits and activities (e.g., different gaits and activities that a soldier will go through during a typical mission, such as but not limited to level, uphill and downhill walking, crawling, and running) The activity engine is also able to detect if the wearer of the soft exosuit 100 is in a transitory phase, or performing non-gait movements (crawling, crouching, etc.), which puts the soft exosuit control in a "hyper-alert" mode, ready to start assistance as soon as is required. Thus, the soft exosuit control system continuously monitors, or monitors at a high frequency, a status of the wearer's movements (or corresponding absence of movements) and adapt the amount of assistance based on the needs of the user and modulate it for the activity or activities in which the wearer is engaged. As depicted in the High-Level Activity/Awareness Engine 1055 of FIG. 25, a soldier is depicted in a Hyper-Alert state (left), Walking (middle) and Stepping Down (right).

Moreover, soft sensors for kinematic and pressure sensing, such as the aforementioned hyper-elastic sensors, can be integrated in the soft exosuit materials (e.g., fabric) for upper and/or lower extremity measurements. Alternatively, separate and apart from the soft exosuit, other garments worn by the user of the soft exosuit may comprise sensors for kinematic and pressure sensing, such as the aforementioned hyper-elastic sensors, and these sensors can be wirelessly linked to the soft exosuit controller(s) through a suitable communication protocol (e.g., Bluetooth, etc.).

In other aspects of the present concepts, signal processing methods and algorithms are used to detect movement intention in soft exosuits and to adapt assistance to the physical status of the wearer based on the detected movement intention. In such aspects, real-time biomechanical, physical-interaction and physiological data are input (e.g., hardwired and/or wireless outputs from one or more sensors or one or more sensing systems to a central controller) to one or more controller(s) that determine the wearer's intention, action and physical state to ensure that the correct assistance is applied at all times by the soft exosuit.

Examples of biomechanical data include but are not limited to the angular rotation speed of body segments (measured through gyroscopes), linear acceleration of body segments (measured through accelerometers), angular position of body segments (measured through inertial measurement units), foot contact and other gait events (measured through foot switches). Example of physical interaction measurements include but are not limited to interaction forces on the cables (measured with load cells), compression forces on the skin (measured with distributed pressure sensors), shear forces. Physiological data examples include heart rate, skin conductivity, EEG signals, surface electromyographic signals.

By integrating the various sensor data, more robust and precise estimations can be developed, as compared to relying on a single sensor type. If necessary, the information from these sensors can be integrated with data from other redundant sensors, such as inertial measurement units. This information can be interfaced to the controller to ensure that the type and level of assistance to each muscle group is robust to gait cadence, step length, level and inclined walking, load bearing and other joint-level variables.

It has been demonstrated that different human activities and motions can be detected by using machine-learning algorithms and pre-processing techniques. Detecting human motions such as walking, running, crouching or stair ascending/descending in real-time can be advantageously used to inform the controller(s) of wearable soft exosuits to provide adequate assistance under these different conditions and or changing conditions. While most of the previous work in exoskeleton design has been carried out in lab environments, hence limiting the user to walking on a treadmill, the present concepts are directly applicable to human actions in real, unstructured scenarios. Information from the soft exosuit's sensors are input into, and interpreted by, control systems adapted to detect and respond to human motion patterns.

The high-level awareness engine 1055 can further monitor the user's biomechanical and physical stress status by analyzing data from the whole body sensor network (e.g., body temperature, perspiration, heart rate, etc.). By analyzing the signal patterns, an intelligent activity-adaptation algorithm is able to inform the low-level controller to adapt the assistance generated to different gaits and activities in which the user is potentially about to engage. For example, a rapid increase in heart rate could indicate, for a soldier, a perceived threat, responsive to which the soldier will be required to run (e.g., to advance toward the threat, to run behind cover, etc.). In this manner, the soft exosuit 100 can continuously monitor the status (e.g., of the soldier) and can adapt the amount of assistance based on the needs of the wearer and modulate it responsive to such needs.

Additionally, the soft exosuit sensors (e.g., an integrated sensor network, such as the kinematic sensors and/or suit tension sensors in FIG. 25) are capable of monitoring and providing real-time biomechanical information to the user in order to provide visual and/or auditory feedback to alert the user to off-normal or emergency conditions (e.g. a breakdown in their gait, extreme physical stress or hardware failure (e.g. low battery)) so that the user can take appropriate corrective action(s), as needed. This approach creates a bi-directional interaction flow between the soft exosuit and the user, promoting a higher perception level leading to more symbiotic interaction.

Figure 26A:
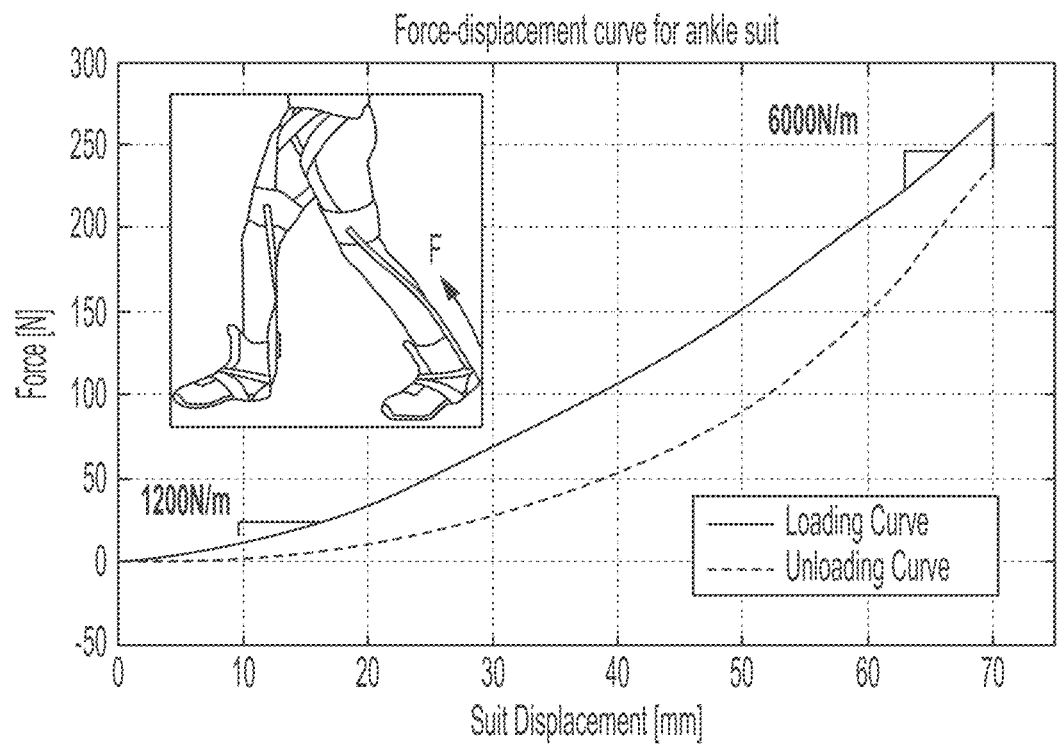
FIGS. 26A-26B show illustrations of force-displacement relationships for an ankle-based soft exosuit and a hip-based soft exosuit, respectively, in accord with at least some aspects of the present concepts.
Figure 26B:
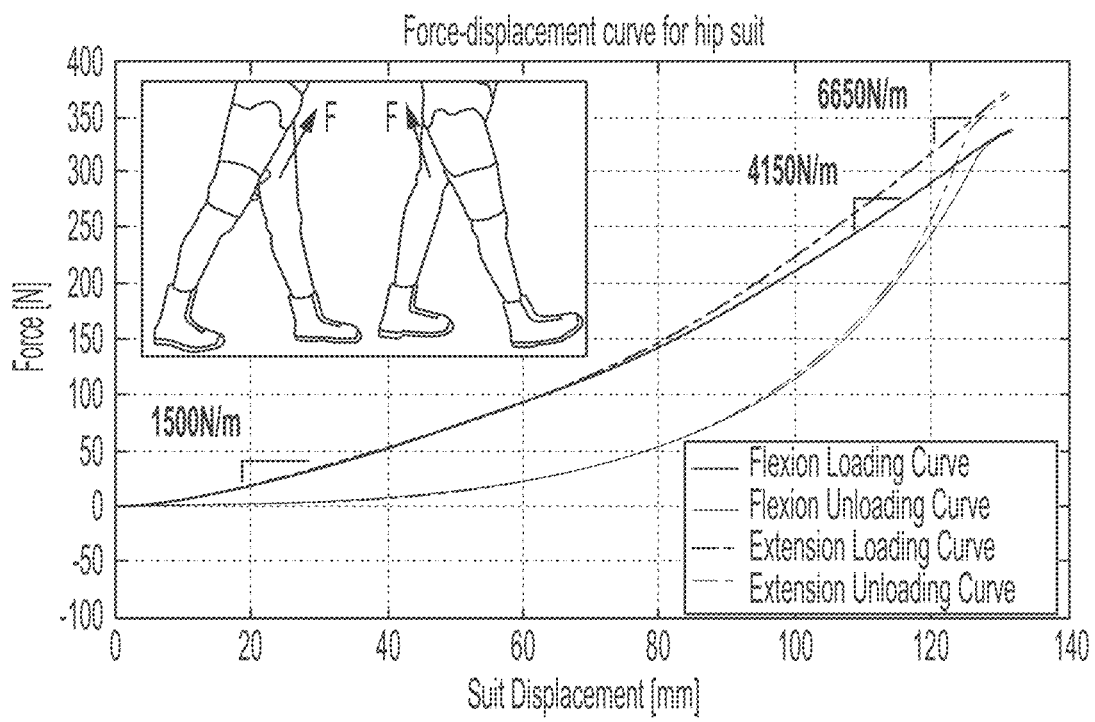

FIGS. 26A-26B, described below, relate to control methods that compute the real-time power flow between the soft exosuit 100, soft exosuit actuation system and the wearer. The power provided by the actuation cable (e.g., cable 142) of the soft exosuit can be calculated, as well as the force and the speed of the cable at an attachment point (at a footwear connector 130) of the soft exosuit. The suit stiffness is then determined by pulling on the ankle cable and recording the force and displacement pairs during multiple loading and unloading cycles. In real-time, power flow can be calculated by using the speed of the cable and the endpoint force, which is measured with a load cell.

The power absorbed and returned by the soft exosuit is calculated using the force in the suit and the suit-human series stiffness model. Given the force at the ankle, the inverse of the stiffness model is used to compute the length discrepancy that must be accommodated by the body's compressing and the suit's stretching. The time-derivative of this variable is taken and multiplied by the force in the suit to compute the Suit Power. The Suit Power, being positive, corresponds to its absorbing power from the wearer and from the motor 246. The power delivered to the human can then be calculated by taking the difference between the power input to the suit and the computed suit power, since the power input to the suit must either go into the suit or the wearer, and the hysteresis losses are already included in the suit power. This power transferred to/from the human is the sum of the powers delivered to the ankle, hip, and knee. The suit stiffness model required for this method was developed by actuating the suit and measuring the resulting force and motor position, while the wearer remained stationary. As is described below, and as shown in FIGS. 26A-26B, this method of estimating the power provided to the wearer is quite accurate.

FIG. 26A shows the force-displacement relationship for an "ankle suit" version of the soft exosuit 100 (see, e.g., FIG. 2A), whereas FIG. 26B shows the force-displacement relationship for a "hip suit" version of the soft exosuit 100 (see, e.g., FIGS. 15A-15B). The hysteresis in the suit was considered for the power calculations. FIG. 26B shows the comparison between the measured power delivered to the wearer by using a Vicon motion capture system and force sensors and the power estimated by using the force measurement in the suit and the stiffness model of the soft exosuit.

Figure 27A:
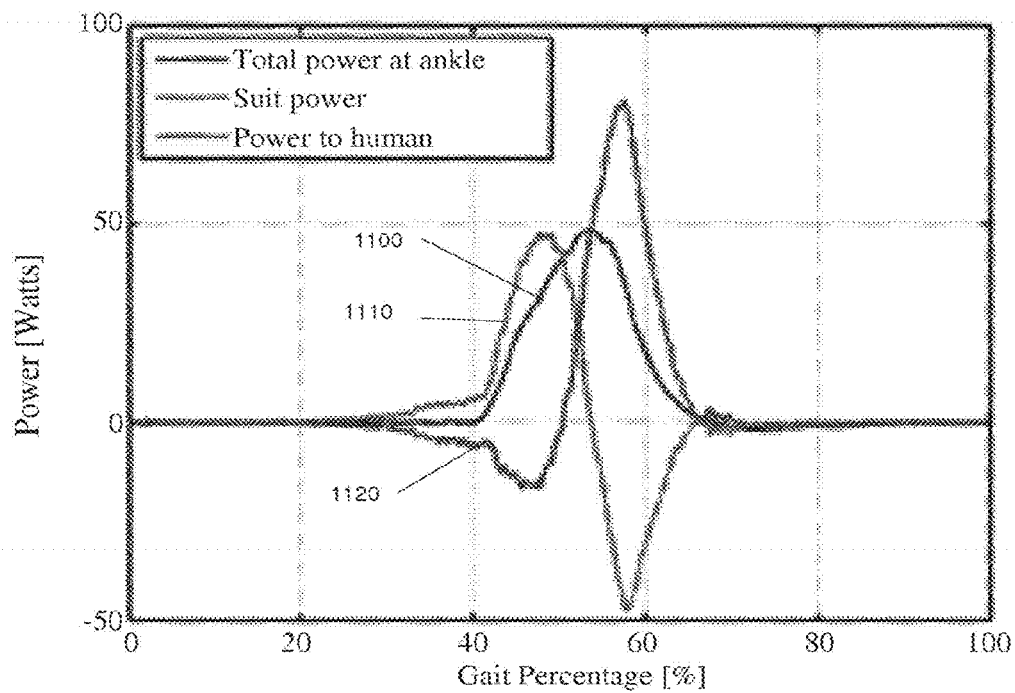
FIGS. 27A-27B show plots of real-time power flow as a function of gait percentage in accord with at least some aspects of the present concepts.
Figure 27B:
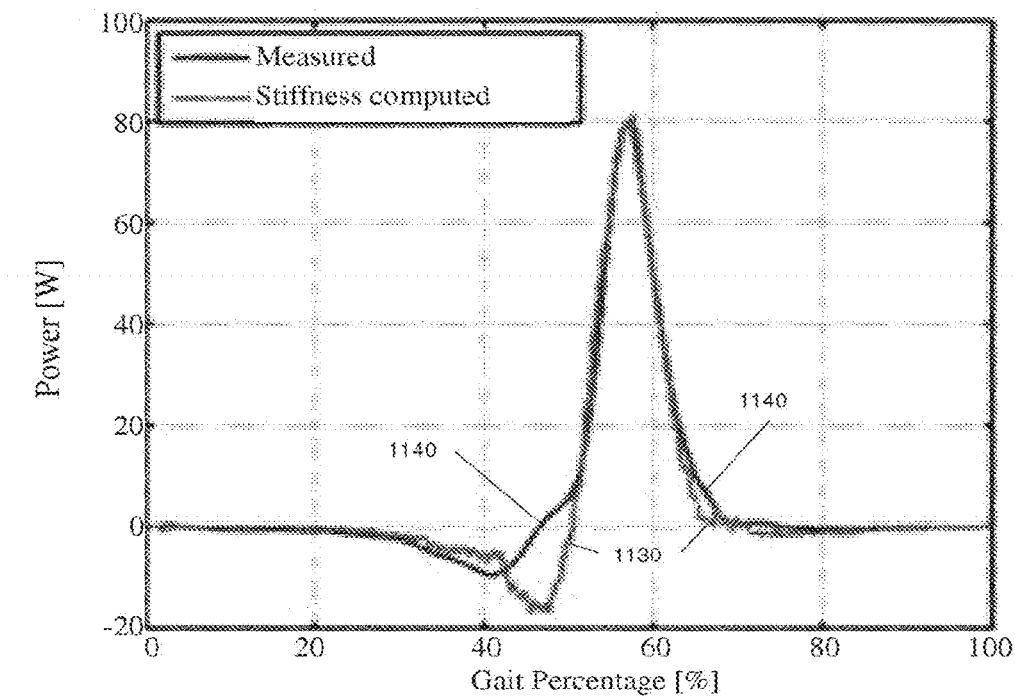

By using the stiffness model of the suit, the power can be calculated, in real-time, in the field. FIGS. 27A-27B show plots of Power (Watts) as a function of Gait Percentage. FIG. 27A shows plots for the total power at the ankle 1100, suit power 1110, and the power delivered to the wearer 1120. FIG. 27B shows plots for the computed stiffness 1130, whereas plot 1140 shows the measured power. Thus, a high-level controller is configurable to observe the power flow, in real-time, and adapt one or more characteristics of the soft exosuit and/or actuator output to optimize the power transferred to the wearer when performing different activities.

The shape and timing of the assistive pulses provided by the soft exosuit 100 can be optimized based on the power transferred to the wearer (which is estimated from the suit stiffness model). For example, the assistive pulse could be changed so that the transferred power is strictly positive, or matches with a desired profile. The assistive pulse can be adjusted by starting with the desired power profile to be transferred to the wearer, and using the algorithm in reverse to generate the desired position of the actuator as a function of time.

The soft exosuit-wearer series stiffness model can also be estimated in real-time, without doing prior measurements, when the wearer is stationary by using estimates of the user's joint angles (from other sensors or with a model of how they walk based on their height, weight, and consequent limb lengths) in conjunction with the motor displacement and force in the suit.

In yet other aspects of the present concepts, the soft exosuit 100 can provide automatic detection and notification of suit misalignments. The soft exosuit 100 monitors the passively generated interaction forces. Preferably, a baseline for the passively generated interaction forces is generated by the wearer simply by walking normally for a few steps so that the system can monitor the dynamic shape of the passively generated forces. If the forces are correct, the system can notify the user that the system has been positioned properly. If there are additional passive forces or the shape of the passively generated tension is not correct, the system will appropriately notify the user that the suit hasn't been properly aligned so that he or she can readjust the position of the one or more components of the wearable system. Based on the measured forces, the soft exosuit 100 may optionally further inform the wearer as to the most likely candidate component for adjustment.

Figures 28A, 28B:
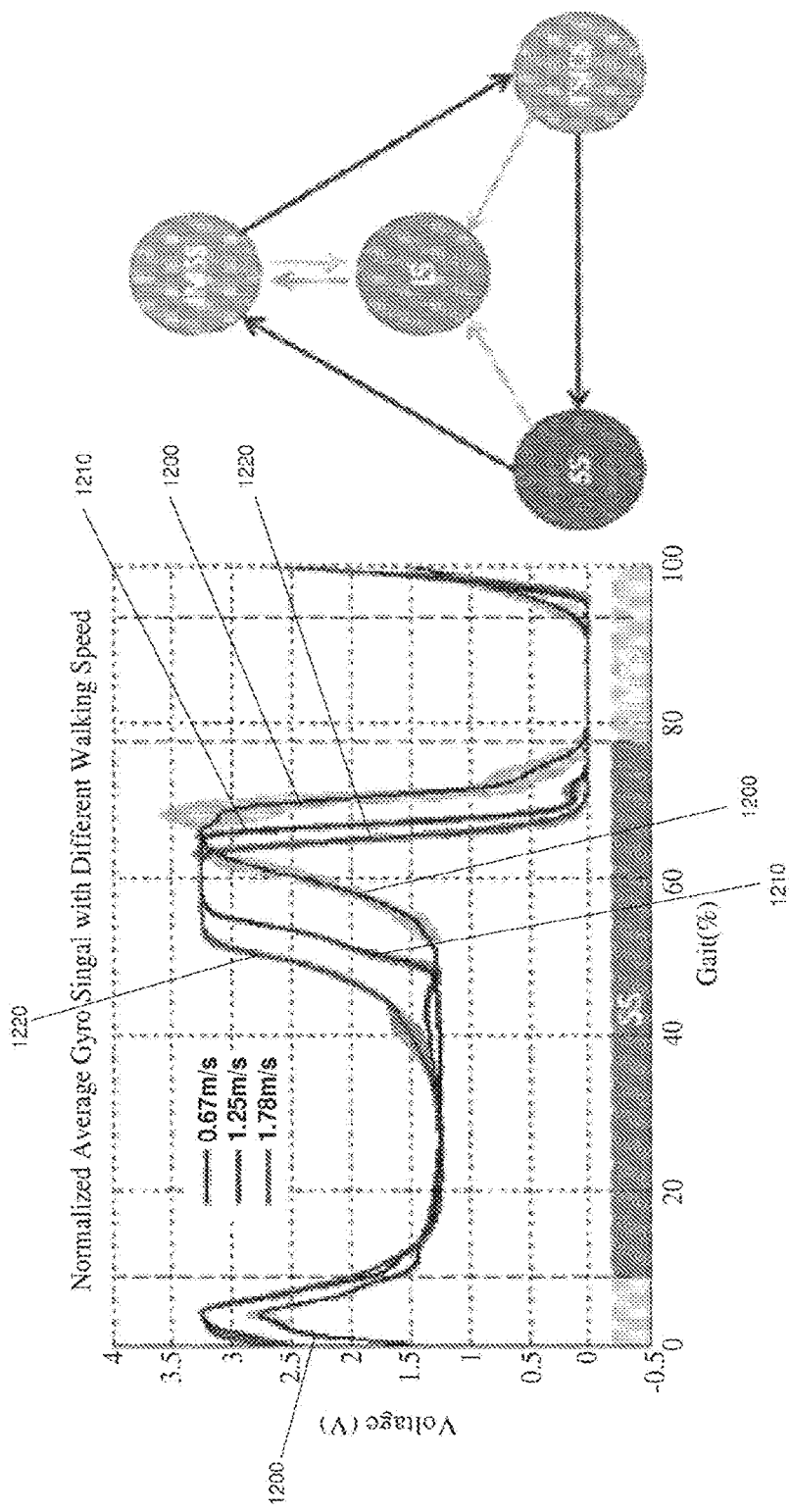
FIGS. 28A-28B show a method and control architecture for a soft exosuit utilizing one or more gyroscopes to detect gait events, including plots of normalized average gyro voltages signals at different walking speeds as a function of gait percentage in accord with at least some aspects of the present concepts.

In still other aspects of the present concepts, the soft exosuit 100 controller(s) detect gait events utilizing one or more gyroscope(s) (e.g., mounted on the heel, mounted on the foot, mounted on the arms, etc.), such as was shown by way of example in FIG. 20A. Foot switches can be replaced with gyroscope sensors located on one or more portions of one or more limbs to detect gait events and reduce the redundancy of the system. A set of gyro data with different walking speeds (0.67 m/s, 1.25 m/s, 1.78 m/s) was collected as shown in FIG. 28A as plots 1200, 1210 and 1220, respectively. Although the walking speeds are different, the 4th % gait event and the ankle positive power event detection remain the same. Thus, a four-state state machine with timing detection can be designed to detect gait events and time the assisting profile.

The four states shown in FIGS. 28A-28B are (1) idle state (IS), non-walking state, (2) initial-mid swing state (IMSS), (3) terminal swing-initial contact state (TSICS) and (4) stance state (SS). For one gait cycle, initial-mid swing state is unique, since the voltage drops to 0 v. This is used as an entry to the state machine from idle state to walking state. Then after the saturation period, it enters terminal swing-initial contact state by detecting heel. In the stance state, once the gyro crosses 1.7V which corresponds to 7.5°/s of the angular speed of the foot comparing to the ground frame, the system starts the assistance. Also, the time for each state is measured, once the elapsed time exceeds the normal time for each state the state machine is set back to idle state. This algorithm adapts robustly when changing walking speed.

In accord with the present concepts, control strategies can also be adapted to assist impaired gait wherein, unlike the prior examples, the control strategies cannot rely on strong regularities of physiological gait typical of a non-impaired wearer, as impaired gait is less regular than physiological gait and every patient has a different gait pattern depending on the type of lesion, advancement of the rehabilitation therapy, and types of compensatory movements developed by the patient.

The control strategies detailed below are able to be used in combination with any gait pattern.

In a first exemplary control strategy for use with any gait pattern, hybrid controls are provided for impaired gait, with automated event detection and manual adjustment from physical therapist. A general architecture for controllers of wearable exosuits comprises two parts (1) an automated algorithm to detect gait events and (2) a manual interface that allows an individual, such as a physical therapist, to determine the timing, type and amount of assistance delivered. As to the first part, the automated algorithm allows the measurement of a multitude of signals such as, but not limited to, angular speeds (gyroscopes) accelerations (accelerometer), magnetic fields (magnetometers), contact switches, and strain sensors. This algorithm can exploit regularities in the signal patterns that are associated with gait event, and processes such measurements to extract the timing of some events that happen during gait such as, but not limited to, heel strike, toe off, and/or mid-stance. This detection of gait events utilizes, in one aspect, a set of logical rules to these measurements of gait event timing and combines them and, in another aspect, uses an expert system, implemented for example with a machine learning algorithm, trained to detect specific events.

As to the second part, a manual interface is provided to enable an individual, such as a physical therapist (or the wearer), to determine the timing, type and amount of assistance delivered. The interface may comprise, for example, a graphical user interface (GUI) implemented on a computer or handheld electronic device (e.g., smartphone) and/or a manual interface, such as a handheld device or wearable input panel with pushbuttons, knobs and/or switches. This interface, however configured, allows regulation of the timing at which assistance from each motor is delivered, relatively to the event (or events) detected automatically. This interface also allows regulation of the amount of assistance that each actuator delivers, as well as regulation of transitions between different assistance levels (e.g., rate of transition, gradual transitions, more abrupt transitions, etc.).

In view of the above, one possible application of this hybrid control scheme is that of gait rehabilitation and gait training in people with mobility problems (caused e.g. by a stroke event, a neuromuscular disease, any other condition or age). Impaired gait lacks the regularity of healthy gait, so that it is not possible to make assumptions on the time delays between different gait events. For example, while the delay between heel strike and the ankle push off phase is regular and predictable in healthy gait, it is unpredictable and very variable in impaired gait. This lack of regularity and predictability can be compensated by this hybrid architecture. The automated part of the algorithm can detect one or more events that happen during gait. The manual interface allows the physical therapist, or the individual himself or herself, to adjust the relative timing of the assistance based on their observation or feeling.

In a second exemplary control strategy for use with any gait pattern, a hybrid control for impaired gait utilizes heel strike detection with a gyroscope and manual tuning of assistance for plantarflexion and/or dorsiflexion. In one embodiment of this control scheme, the automated event detection can detect the heel strike (e.g., using measurements from an accelerometer, a gyroscope, a contact switch, and/or a stretch sensor, etc.), and the manual interface can be used to tune the delay at which assistance to plantarflexion (ankle push-off phase) or dorsiflexion (swing phase), or both, is given. In another embodiment of this control scheme, the automated event detection can detect any event happening before the push-off phase, and the manual interface can be used to time the delay to actuate plantarflexion. In yet another embodiment of this control scheme, the automated event detection can detect any event happening before toe off, and the manual interface can be used to time the delay to actuate dorsiflexion. These embodiments, where an event is detected at any time before actuation takes place, allows achievement of a very high degree of adaptation, since everything happens within the same step.

In a third exemplary control strategy for use with any gait pattern, a hybrid control for impaired gait is adapted to detect any number of gait events on a leg and define trajectories based on these events. In this embodiment, a number N of sensors is placed on the body. Readings from these N sensors are used to detect M events during gait. In one embodiment, a manual interface, such as a GUI, allows to determine when assistance is generated in relation to these events. Each of the M events can be used as a time reference to start, modify, or stop assistance. In another embodiment, a manual interface, such as a GUI, allows determination of the amount and type of assistance generated between each pair of subsequent events. In another embodiment, the manual interface is gradually replaced by an expert system (automated algorithm) that learns and replaces the manual inputs from the physical therapist.

In a fourth exemplary control strategy for use with any gait pattern, a hybrid control for impaired gait is adapted to detect gait events on the normal leg to actuate the assistance to the impaired leg. An example of this control architecture, based on detecting gait events on the normal leg, to assist the impaired leg, is shown in FIGS. 29A-29B. FIGS. 29A-29B shows a possible pattern for signals of a gyroscope mounted on both heels in a patient with impaired gait. In a possible embodiment of this algorithm, the clear, three-peak pattern at the normal leg (FIG. 29B) can be utilized as a time reference to assist the impaired leg (shown in FIG. 29A). In this example, stance phase in both FIGS. 29A-29B is marked by shaded areas. By detecting peaks during the swing phase of the normal leg (FIG. 29B), one can extract a reference for an event that always happens before the swing phase of the impaired leg. This reference can be used to actuate dorsiflexion, which happens during the swing phase.

Equivalently in other embodiments, different types of sensors can be put on the normal leg to detect gait events that can be used to time the contralateral, impaired leg.

This architecture also allows a controller to be configured to observe the movement pattern of the sound leg through one or more sensors, and can actuate the impaired limb so that it can gradually converge to a similar gait pattern.

Figure 30:
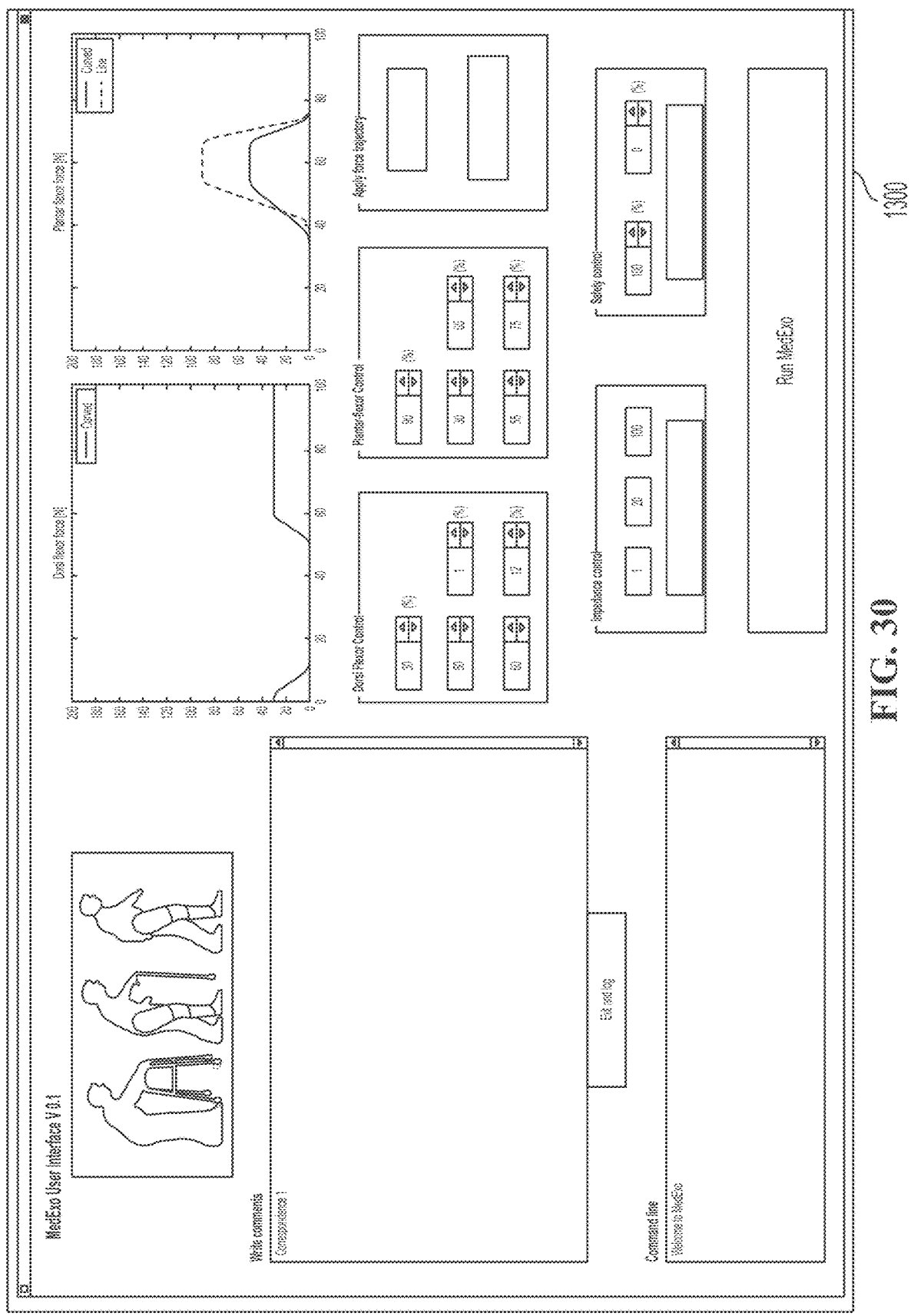
FIG. 30 shows a graphical user interface for a soft exosuit control system in accord with at least some aspects of the present concepts.

FIG. 30 shows a software interface for medical controls, specifically showing a graphical user interface 1300 to display real-time gait parameters measured by the sensors on the suit, as well as input means (data entry fields) of controlling the profile and timing of assistance delivered by the suit in real-time.

In various aspects, the graphical user interface 1300 displays real-time gait data calculated from the suit sensors to provide quantitative information about the patient's gait. The real-time gait data may include, for example, but is not limited to, any one or more of stance symmetry (amount of time single-leg stance on each leg), step length, speed/cadence, knee extension, plantar flexion force, degrees of dorsiflexion, and ground clearance. This output may be displayed quantitatively or graphically, and clinicians will be able to select which parameters they wish to view. The graphical user interface 1300 can also display saved gait and use data to indicate longer term trends, which will be useful for clinicians or patients to view data accrued in between clinic visits. Such data may include long term trends regarding walking speed, distance walked per day, level of assistance supplied by the suit, and/or hours of suit use per day. This data will also be useful to verify patient compliance and to justify use of the suit for third-party payers.

As shown, the GUI 1300 allows the user (e.g., medical provider, patient, researcher, etc.) to control the forces and timing of dorsiflexion and plantar flexion assistance as provided by the suit. The interface includes inputs for the maximum force to apply on the dorsiflexion and plantarflexion cables. The researcher also inputs the beginning and ending timepoints for the ramp up and ramp down for each force based on the calculated gait cycle. Safety measures are advantageously built into the interface, or input into the interface (e.g., by an authorized medical provider) to prevent accidental inputs that exceed preset allowable force or position limits. Impedance, Force, and Position limits can be modified within the interface. Additionally, when a new force profile is generated, it is drawn superimposed on top of the current force profile to emphasize any differences between the two profiles. The new profile must be confirmed by the user before it can be applied to the suit.

In at least some aspects, the GUI 1300 contains a commenting pane that allows the user (e.g., medical provider, patient, researcher, etc.) to enter comments that are time-synced to the changes in force profile. Such comments may detail, for example, reasons a particular change was made, what was working successfully, what was not working successfully, or what is needed to be implemented in the future.

In at least some aspects, the GUI 1300 is accessible on a computer or device remote from the soft exosuit 100 and the computer and the soft exosuit 100 are networked together (e.g., via a wireless connection) such that the changes entered into the GUI 1300 are automatically incorporated into the soft exosuit control system. Thus, a clinician treating a patient, or a supervisor monitoring a soldier, can both monitor the soft exosuit 100 data and effect real-time modifications to the control system to suit particular needs of the wearer of the soft exosuit (e.g. patient, soldier, etc.). In the clinical application, this interface enables the clinician to adjust the soft exosuit 100 as the patient progresses throughout their rehabilitation, to ensure that the suit is providing the appropriate amount and timing of assistance throughout the patient's full recovery process.

Further to the above, the human/machine interface and interaction between the wearer and the soft exosuit 100, together with the implications of such interaction on the control algorithms, are discussed below.

Broadly, control is the strategy by which active elements (e.g., tensile elements, actuation devices, etc.) in a soft exosuit are commanded to change their length during an activity. The soft exosuit 100 can have its length changed by active elements in the soft exosuit that provide changes either within a single step, or slowly-varying across many steps (e.g., useful for gradual change in terrain). Automated and/or manually-adjustable elements can also be used to change the length of the suit. The soft exosuit 100 disclosed herein is unique, inter alia, in that if it is made slack (by increasing the length) then it is fully transparent to the wearer, meaning that it does not restrict their motion.

The soft exosuit 100 can develop tension in it by two ways. The first is that active elements change its length to pull it tight over the body. The second is that the body can move, and the soft exosuit is extended due to the motion of the joints and the fact that the soft exosuit material extends over at least one joint at some radius from the joint. These two methods of developing tension in the soft exosuit are illustrated in FIGS. 31A-31B.

Figure 31A:
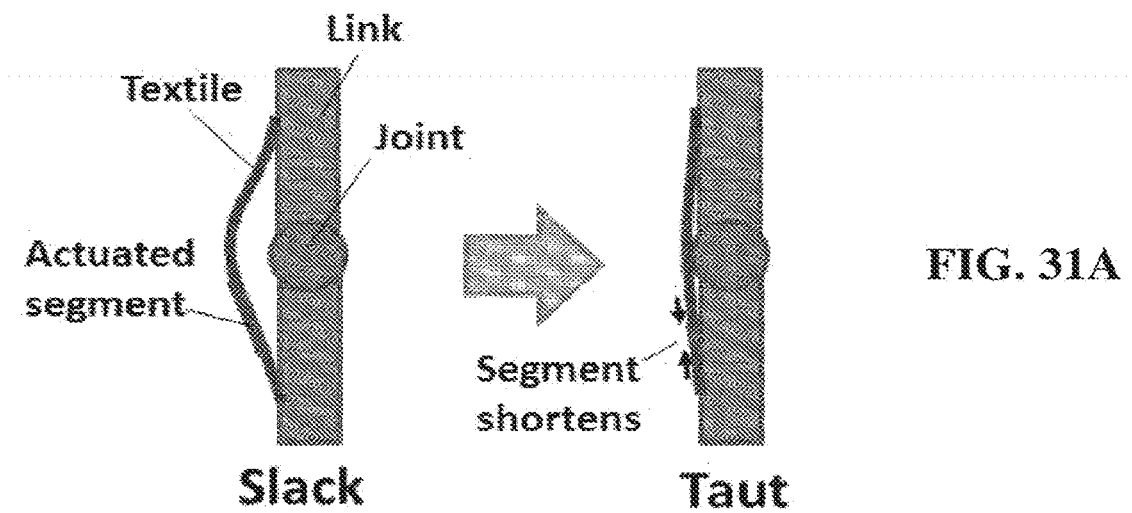
FIGS. 31A-31B show concepts of operation for a soft exosuit in accord with at least some aspects of the present concepts.
Figure 31B:
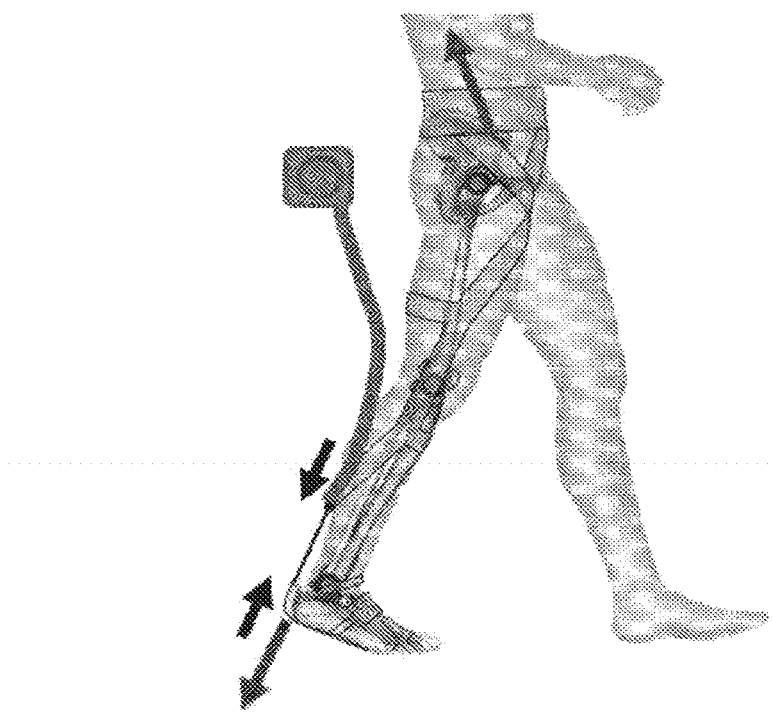

FIGS. 31A-31B show a method and system for developing tension in a soft exosuit 100 by using actuated segments to shorten the length of the suit. FIG. 31A illustrates the concept, and FIG. 31B shows how the concept can be used on a specific example of a soft exosuit. In FIG. 31B, the arrows at the back of the calf indicate that that segment of the soft exosuit is shortening; the arrows at the pelvis and heel indicate force is induced in the soft exosuit and the body must apply reaction forces at these locations to prevent the soft exosuit from displacing at these locations.

Figure 32A:
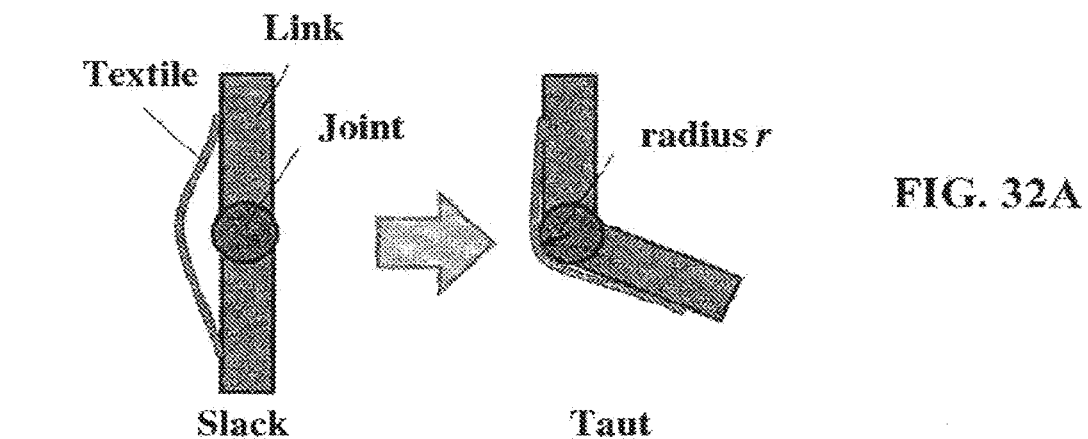
FIGS. 32A-32B show additional concepts of operation for a soft exosuit in accord with at least some aspects of the present concepts.
Figure 32B:
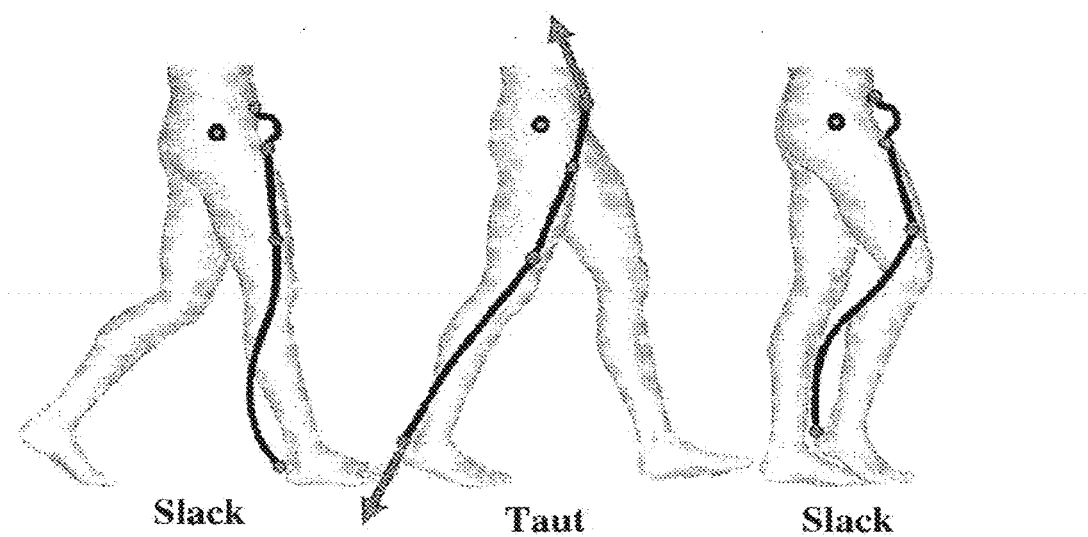

FIGS. 32A-32B show a method and system for developing tension in a soft exosuit due to the wearer's body changing configuration. FIG. 32A shows how, if a textile or other flexible tensile element is affixed to a body segment at either side of a joint, and then the joint bends, then tension is induced in the textile or other flexible tensile element if it is routed at a radius r>0 around the joint. FIG. 32B shows a possible path for a soft exosuit 100 which is anchored to the wearer at the front of the waist and the back of the heel. It passes through the knee joint, but is located at positive radii in front of the hip and behind the ankle. When the wearer moves into the position shown in the middle image of FIG. 32B, the soft exosuit becomes taut due to its stretching over the hip and ankle. The forces exerted on the soft exosuit by the body in order to keep it from moving are shown in the middle image of FIG. 32B by the arrows at the waist and heel. At other leg positions, the soft exosuit is slack.

With this understanding of how forces are created in a soft exosuit, there are many schemes that can be used to control the tension in the suit.

If the soft exosuit 100 is made slack (by choosing the initial length such that is longer than the body in a given pose, or by extending actuated segments) then the force in the soft exosuit is substantially zero (forces <2N, which is similar to wearing a pair of jeans). Having zero force, or substantially zero force, in the soft exosuit is useful because it does not restrict the wearer's motion, and is generally not noticeable to the wearer. This could be useful if the wearer only wants assistance during certain motions (e.g. climbing up stairs) and does not want to be encumbered or restricted by the soft exosuit during other motions (e.g. walking on level ground).

Another possibility is to have a small positive amount of force in the soft exosuit 100 (0.0001-10N) which is maintained even if the wearer moves to different poses. To achieve this, the soft exosuit must include actuated segments which extend and contract as needed to maintain that amount of tension in the soft exosuit as the wearer's poses, movements, and stances change. Maintaining a small positive amount of force in the soft exosuit is useful for several reasons. The position trajectory that the actuators move through while maintaining this small amount of tension can be used to determine the position of the body, which is useful for control. For example, the actuators may apply higher forces when the body reaches a certain pose, or the body's pose may be used to inform the control of actuators connected to a different load path on the body (which would actuate different joint(s) or the same joint(s) in the opposite direction). The position trajectory of the actuators while maintaining small forces in the soft exosuit may also be logged to determine how the wearer moved over time, for example to monitor their biomechanics. Also, maintaining a small force in the soft exosuit at all times permits the actuators to respond faster if it is desired that they apply higher forces, because they don't need to reel in large amounts of slack in the suit.

A final possibility is to have large amounts of force in the soft exosuit (>10N). This amount of force is useful for applying torques to the biological joints, for example to assist the wearer while walking. This amount of force will be utilized only at specific times if a wearer is in motion. For example, during walking the soft exosuit can assist push-off at the ankle which occurs primarily from 40-60% in the gait cycle. Or, if someone was receiving assistance as they performed a sit-to-stand maneuver, the soft exosuit could provide force during the entire motion, and then cease providing force once the motion was complete.

A second concept useful in understanding how an exosuit can be used is the concept of power transfer to or from the wearer. Consider an exosuit assisting a single joint in a single direction, for example an exosuit to assist hip extension. In this case, the soft exosuit applies tension pulling the hip further into extension. If the joint is moving in the same direction as the applied force, the soft exosuit transmits positive power to the joint. In aspects of the soft exosuit 100 employing hip extension (see, e.g., FIGS. 15A-15B), this corresponds to the hip extending while there is force in the soft exosuit. Conversely, if the joint is moving in the opposite direction from the applied force, then the soft exosuit is applying negative power to the joint, or in other words the soft exosuit is absorbing power from the joint. In aspects of the soft exosuit 100 employing hip extension (see, e.g., FIGS. 15A-15B), this corresponds to the hip flexing while there is force in the soft exosuit.

Figure 33:
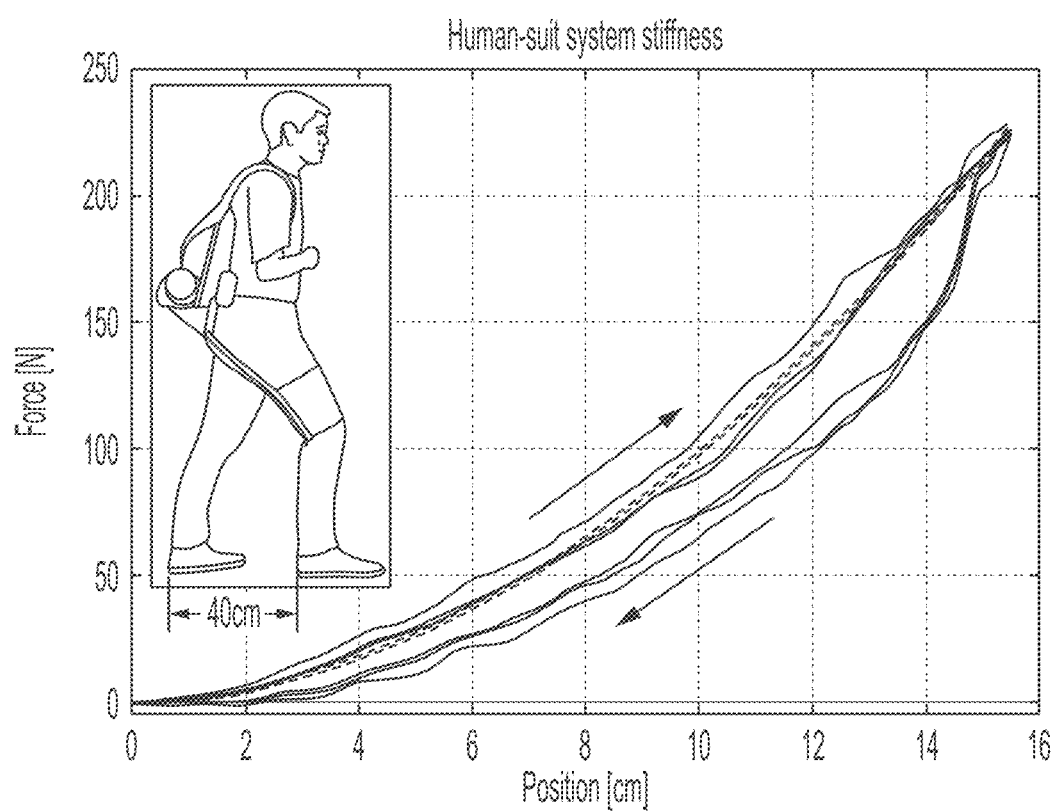
FIG. 33 shows a control scheme to determine human-soft exosuit stiffness in a fixed pose to provide a repeatable force-displacement characteristic in accord with at least some aspects of the present concepts.

As shown in FIGS. 33 and 34A-34B, forces created in the soft exosuit are dependent on the underlying joint motion. In other words, the active portions of the exosuit are controlled to only create significant forces in the soft exosuit during periods when the force would deliver positive power to the wearer. For an exosuit that crosses a single joint, the motion of the joint could be monitored by one or more sensors (e.g., sensors disposed on or about the joint or on a limb or interest) or inferred by one or more sensors (e.g., sensors disposed on or about another joint or another limb, the output of which can provide complementary information regarding a joint or limb of interest). When the joint is moving in the direction that the exosuit applies force, the actuators could create significant force in the soft exosuit. If the joint began moving in the opposite direction, the actuators could move to stop creating significant force in the soft exosuit. This strategy ensures that the soft exosuit only provides positive power to the wearer and does not absorb energy from the wearer.

During the periods when significant force is not being applied, the actuator(s) 200 could either move to create slack in the suit, move to track the wearer while applying small forces, or some combination thereof. If the actuator(s) 200 are tracking the wearer while applying small forces, the lengths of the actuators could be used to detect when the joint is moving in the same direction as the soft exosuit 100 is applying force: if the actuators are shortening an aspect of the soft exosuit, then the joint is moving in the same direction as the soft exosuit applies force. If the actuator(s) must move to lengthen the aspect of the soft exosuit, then the joint is moving in the opposite direction.

If there is slack in the suit, other sensors such as gyroscopes, soft strain sensors, etc. can be used to estimate the joint's motion. Gyroscopes can be used to estimate the joint's velocity directly, and so a positive or negative reading (measured in the sagittal plane, for example) will directly correspond to if the joint is flexing or extending. Tension can be created in the soft exosuit 100 when the joint is moving in the direction corresponding to positive power being transmitted from the soft exosuit to the body. For joint angle sensors, changes in the direction of motion must be detected.

If the actuator(s) 200 are applying significant amounts of force to the soft exosuit 100 and applying positive power to the body, then the time at which they should release tension in the soft exosuit can be detected in several ways. Sensors such as gyroscopes, soft strain sensors, etc. can be used to estimate the joint's motion. Alternatively, the actuator lengths can be used in conjunction with the measured force in the soft exosuit and a model of the force-displacement characteristics of the soft exosuit and wearer to estimate the joint's motion. An example of how a model of the suit-human force-displacement can be used with the force and motor position is shown in FIGS. 33 and 34A-34B.

FIG. 33 shows a measured human-suit system stiffness. The wearer stands in a certain pose corresponding to the shape their body would be in when the motor is actuated during the task (e.g. with their leg forward as if they were at 10% in the gait cycle). Then, the actuated portions of the soft exosuit 100 change length, and the resulting force in the soft exosuit is recorded. The graph of FIG. 33 shows the actuator displacement vs. the induced force. A model is created by fitting equations to the data: for example, a quadratic equation (Force=$a*x^2+b*x$, where x is the displacement, and a and b are constants) fits the rising slope of the curve, and an exponential (Force=$c*exp(-d*(x-xmax))$, where c, d, and xmax are constants) fits the falling slope of the curve. This gives a repeatable force-displacement characteristic. The arrows above and below the data plots indicate the direction around the hysteresis loop.

With this model, given the force in the suit, the time-history of the force (to determine if the force is rising or falling), and the actuator length, the position of the person can be determined. FIGS. 34A-34B show plots of the hip moment (which is a scaled version of the force in the suit) and the position of the actuator(s) 200 during the walking cycle. The force in the soft exosuit over one gait cycle is shown by the solid black line ("Approx") in FIG. 34A. Using the inverse model, the displacement of the suit-human system is computed from this force and the result is "$x_s$" 1400 in FIG. 34B. The length of the actuators is shown in FIG. 34B as plot "$x_m$" 1410. The position of the hip is shown by "$x_{hip}$" 1420 in FIG. 34B. This is unknown but can be computed using the suit-human system displacement $x_s$ and the actuator length $x_m$ via the relation $x_{hip}=x_m+x_s$.

For a soft exosuit 100 that crosses multiple joints, similar principles can be used. The displacement produced by the actuator(s) to track the body while maintaining low force in the soft exosuit is a function of the angles of the joints crossed and the radii the soft exosuit is offset at those joints. The angles of multiple joints crossed by the soft exosuit can be tracked, and tension can be created in the soft exosuit when all of the angles are moving in directions corresponding to their receiving positive power from the soft exosuit.

In general, it may not be maximally beneficial to only create tension in the soft exosuit 100 when it can transmit positive power to the body. It may be useful to duplicate the body's function (absorbing power when the biological joints absorb power, transmit power to the body when the biological joints produce power) in order to make the soft exosuit 100 feel more natural and synergistic with the body. Acting in this manner also may permit the body to move in more natural ways (e.g., maintain kinematics closer to nominal ways of walking), which can lead to better performance. To accomplish this with a soft exosuit 100 that crosses multiple joints, the tension in the soft exosuit can be a function of each of the joint angles.

As such, tension in the soft exosuit 100 can be created as a function of the joint angles. If the actuator(s) 200 are moving continually to maintain a small tension in the suit, the actuator length can be used instead of or in addition to the joint angle measurements.

A soft exosuit 100 that crosses multiple joints can be used to transfer power from one joint to another joint or joints, if one joint is producing positive power while the other joint(s) is (are) absorbing power, or if both joints ordinarily produce positive power but one is actuated by the body less than usual due to weakness or injury. For example, a soft exosuit 100 going across the back of the thigh, through the knee, and to the shin can transfer power from the hip to the ankle to raise the fore-foot during 60-100% in the gait cycle. This device would be useful for people with muscular dystrophy or stroke who have weakness in their tibialis anterior muscle which raises the foot in dorsiflexion. When the thigh moves into flexion, tension would be created in the soft exosuit 100 due to the hip's motion. This tension would pull up on the front of the foot, thereby helping the foot to clear the ground.

In accord with the present concepts, the soft exosuit 100 need not cross multiple joints (a multi-articular soft exosuit architecture) and may, instead, cross only one joint. By way of example, the concepts disclosed herein, inclusive of control schemes, apply equally to a soft exosuit interfaces with the calf and being connected to one or more footwear connection element(s) disposed at a back and/or of the user's footwear. It is to be emphasized that the anchor points for the soft exosuit may comprise anatomical features, including musculature, dimensioned to resist application of tensile forces.

The description above refers to various exemplary aspects of the present concepts. Each of these embodiments and obvious variations thereof are contemplated as falling within the spirit and scope of the disclosed invention, at least some aspects of which are set forth in the following claims. By way of illustration, but not limitation, the control systems disclosed herein in relation to examples of soft exosuits 100 are equally applicable to robots (i.e., stand-alone robots), wearable robotic systems and devices, such as traditional exoskeleton-based wearable robotic systems or prosthetic devices. Thus, rather than relying on mere preprogrammed movement patterns, all wearable robotic systems (both soft exosuits as disclosed herein, traditional exoskeleton-based wearable robotic systems, prosthetic devices, or combinations thereof) are able to be made more adaptive. Additionally, although a number of examples of soft exosuit force transmission are described in relation to a Bowden cable or other cable type, force transmission in accord with the present concepts may advantageously use any variety of flexible transmission elements such as, but not limited to, flexible webbing or ribbon material (e.g., fabrics, composite materials, etc.).

In yet further aspects, the control systems disclosed herein may advantageously use, as an input, a motor current, with the controller(s) utilizing the motor current as an indication of a motor torque applied to an actuation member and, correspondingly, a force applied through the actuation member to the attachment point of the actuation member.

It at least some aspects, the control systems may be configurable by a user (or an authorized third party, such as a medical care provider) to modify the profiles of forces applied by the soft exosuit actuator(s), such as to soften the ramp up in application of force (e.g., to facilitate adaptation by the user to the force) and/or ramp down of the application of force (e.g., to minimize the feeling by the user that they suddenly have "heavy legs").

It at least some aspects, the control system embodies a "fail safe" protocol in which, should any component of the system fail (e.g., a sensor failing high or failing low), the control system takes corrective actions to place the soft exosuit in a configuration in which the soft exosuit is minimally disruptive to the wearer.

What is claimed is:

1. A motion control system, comprising:
   at least one actuator comprising at least one actuation member, the at least one actuation member having a proximal end attached to the at least one actuator and configured to be disposed on a first side of a joint when worn and having a distal end attached to an anchor element attachment point and configured to be disposed on a second side of the joint when worn;
   a first sensor configured to output signals correlated with or correlatable to a timing of a gait cycle;
   a second sensor configured to output signals representing a tensile force in the at least one actuation member; and
   at least one controller configured to receive the signals output from the first sensor and the second sensor and, responsive thereto, automatically actuate the at least one actuator, during a first portion of the gait cycle, to apply a force greater than a predetermined threshold tensile force to the anchor element attachment point via the at least one actuation member to generate a beneficial moment about the joint to assist movement of the joint, and to automatically actuate the at least one actuator, during at least a second portion of the gait cycle, to reduce a tensile force at the anchor element attachment point to a level at or below the predetermined threshold tensile force to avoid generating a detrimental moment about the joint,
   wherein the at least one controller is configured to use the signals output from the first and second sensors from only a current step to determine a timing at which the tensile force crosses the predetermined threshold and to determine a timing at which a peak tensile force is achieved during a first phase of the gait cycle.

2. The motion control system according to claim 1, wherein the joint comprises an ankle joint, and
   wherein the anchor element attachment point comprises a footwear connection element, and wherein the first portion of the gait cycle comprises a range between 30-62.5% of the gait cycle, wherein the gait cycle extends from one heel-strike to a next heel-strike.

3. The motion control system according to claim 2, wherein the at least one controller is configured to actuate the at least one actuator, during the second portion of the gait cycle, from 62.5% of the gait cycle to subsequent heel strike, to reduce a tensile force at the anchor element attachment point to substantially zero.

4. The motion control system according to claim 2, wherein the first portion of the gait cycle corresponds to a range between midstance and toe off.

5. The motion control system according to claim 1, wherein the joint comprises a hip joint, and
   wherein the anchor element attachment point comprises a thigh brace connection element configured to be disposed on a hamstring region of a user when worn, and wherein the first portion of the gait cycle comprises a range between 0-62.5% of the gait cycle, wherein the gait cycle extends from one heel-strike to a next heel-strike.

6. The motion control system according to claim 5, wherein the at least one controller is configured to actuate the at least one actuator, during the second portion of the gait cycle, corresponding to a swing phase, to reduce a tensile force at the anchor element attachment point to substantially zero.

7. The motion control system according to claim 6, wherein the tensile force is between 0 Newtons-5 Newtons.

8. The motion control system according to claim 5, wherein the end of the first portion of the gait cycle corresponds to a stance phase.

9. The motion control system according to claim 1, wherein the automatic actuation of the at least one actuator by the at least one controller during a first portion of the gait cycle is triggered by a measured increase in tensile force in the at least one actuation member to a predefined threshold value between 20 Newtons-50 Newtons.

10. The motion control system according to claim 1, wherein the first sensor comprises at least one hyperelastic strain sensor.

11. The motion control system according to claim 1, further comprising:
    a third sensor,
    wherein the at least one actuator comprises a plurality of actuators, the plurality of actuators comprising a first actuator operatively associated with a first actuation member, the first actuation member having a proximal end attached to the first actuator and configured to be disposed on a first side of a first joint when worn and having a distal end attached to a first anchor element attachment point and configured to be disposed on a second side of the first joint when worn and comprising a second actuator operatively associated with a second actuation member, the second actuation member having a proximal end attached to the second actuator and configured to be disposed on a first side of a second joint when worn and having a distal end attached to a second anchor element attachment point and configured to be disposed on a second side of the second joint when worn, wherein the third sensor is configured to output signals representing a tensile force in the second actuation member, wherein the at least one controller is configured to receive the signals output from the first and second sensors and, responsive thereto, automatically actuate the first actuator, during the first portion of the gait cycle, to apply a force greater than a first predetermined threshold tensile force to the first anchor element attachment point via the first actuation member to generate a beneficial moment about the first joint to assist movement of the joint, and to automatically actuate the first actuator, during at least the second portion of the gait cycle, to reduce a tensile force at the first anchor element attachment point to a level at or below the first predetermined threshold tensile force, wherein the at least one controller is further configured to receive the signals output from the first and third sensors and, responsive thereto, automatically actuate the second actuator, during a third portion of the gait cycle, to apply a force greater than a second predetermined threshold tensile force to the second anchor element attachment point via the second actuation member to generate a beneficial moment about the second joint to assist movement of the joint, and to automatically actuate the second actuator, during at least a fourth portion of the gait cycle, to reduce a tensile force at the second anchor element attachment point to a level at or below the second predetermined threshold tensile force, and wherein each of the first portion of the gait cycle and the third portion of the gait cycle comprise at least a portion of a stance phase.

12. The motion control system according to claim 11, wherein the first joint is an ankle joint,
wherein the second joint is a hip joint, and
wherein the first joint and the second joint are both on a same leg.

13. The motion control system according to claim 12, wherein the first portion of the gait cycle comprises a region between mid-stance and pre-swing, and
wherein the third portion of the gait cycle comprise a region of gait between initial contact and pre-swing.

14. The motion control system according to claim 12, wherein the first portion of the gait cycle comprises a region between 30%-62.5% of the gait cycle, wherein the gait cycle extends from one heel-strike to the next, and
wherein the third portion of the gait cycle comprises a region between 0%-62.5% of the gait cycle.

15. The motion control system according to claim 1, further comprising:
a plurality of sensors,
wherein the at least one actuator comprises a plurality of actuators, the plurality of actuators comprising a plurality of actuation members, the plurality of actuation members configured to span a plurality of joints when worn,
wherein the plurality of sensors are configured to output signals representing tensile forces in the plurality of actuation members, and
wherein the at least one controller is configured to receive the signals output from the plurality of sensors and, responsive thereto, automatically actuate respective ones of the plurality of actuators, during a predetermined portion of the gait cycle for each respective one of the plurality of actuation members, to apply across a respective joint a predetermined force profile to generate a beneficial moment about said joint to assist movement of the joint.

16. A motion control system, comprising:
a first anchor configured to be disposed on a first side of a joint when worn by a user;
a second anchor configured to be disposed on a second side of the joint when worn by the user;
at least one actuator operatively connected to the first anchor and the second anchor, wherein the actuator is configured to apply a tensile force to generate a moment about the joint;
at least one sensor configured to sense information related to the gait cycle;
at least one processor configured to operate the actuator such that the tensile force is greater than a threshold tensile force during a first portion of a gait cycle and less than or equal to the threshold tensile force during a second portion of the gait cycle, wherein the processor is configured to receive the information from the at least one sensor, and wherein the processor is configured to determine a timing for the first and second portions of the gait cycle based on the received information only from a current gait cycle.

17. The motion control system of claim 16, wherein the at least one sensor includes a first sensor configured to output a signal correlated with or correlatable to a timing of a gait cycle.

18. The motion control system of claim 17, wherein the at least one sensor includes a second sensor configured to sense the tensile force.

19. The motion control system of claim 18, wherein the processor is configured to determine a timing for the first and second portions of the gait cycle based on a timing at which the sensed tensile force crosses the predetermined threshold and a timing at which a peak tensile force is achieved during a first phase of the gait cycle.

* * * * *